(12) United States Patent
Shapiro et al.

(10) Patent No.: US 10,517,890 B2
(45) Date of Patent: Dec. 31, 2019

(54) TRIGGERING RNA INTERFERENCE WITH RNA-DNA AND DNA-RNA NANOPARTICLES

(71) Applicant: The United States of America, as represented by the Secretary, Department of Health & Human Services, Rockville, MD (US)

(72) Inventors: Bruce A. Shapiro, Gaithersburg, MD (US); Kirill A. Afonin, Charlotte, NC (US); Mathias D. Viard, Frederick, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 224 days.

(21) Appl. No.: 15/309,157

(22) PCT Filed: May 6, 2015

(86) PCT No.: PCT/US2015/029553
§ 371 (c)(1),
(2) Date: Nov. 4, 2016

(87) PCT Pub. No.: WO2015/171827
PCT Pub. Date: Nov. 12, 2015

(65) Prior Publication Data
US 2017/0274000 A1  Sep. 28, 2017

Related U.S. Application Data

(60) Provisional application No. 61/990,094, filed on May 7, 2014, provisional application No. 61/989,520, filed on May 6, 2014.

(51) Int. Cl.
*A61K 31/713* (2006.01)
*C12N 15/11* (2006.01)
*C12N 15/113* (2010.01)
*C12N 15/79* (2006.01)
*A61K 47/50* (2017.01)

(52) U.S. Cl.
CPC ............ *A61K 31/713* (2013.01); *A61K 47/50* (2017.08); *C12N 15/11* (2013.01); *C12N 15/111* (2013.01); *C12N 15/113* (2013.01); *C12N 15/79* (2013.01); *C12N 2310/14* (2013.01); *C12N 2310/3519* (2013.01); *C12N 2310/51* (2013.01); *C12N 2320/11* (2013.01); *C12N 2320/51* (2013.01); *C12N 2320/53* (2013.01)

(58) Field of Classification Search
CPC ...... A61K 31/713; A61K 47/48; A61K 47/50; C12N 15/111; C12N 2310/51
USPC ...... 435/6.1, 6.11, 91.1, 91.31, 455; 514/44; 536/23.1, 24.5
See application file for complete search history.

(56) References Cited

U.S. PATENT DOCUMENTS

| | | | |
|---|---|---|---|
| 5,281,781 A | 1/1994 | Herchenröther et al. |
| 5,466,586 A | 11/1995 | Davey et al. |
| 5,580,737 A | 12/1996 | Polisky et al. |
| 6,261,783 B1 | 7/2001 | Jayasena et al. |
| 6,469,158 B1 | 10/2002 | Usman et al. |
| 6,787,305 B1 | 9/2004 | Li et al. |
| 6,916,653 B2 | 7/2005 | Eagles et al. |
| 8,084,599 B2 | 12/2011 | Rossi et al. |
| 9,732,337 B2 | 8/2017 | Shapiro et al. |
| 2003/0003469 A1 | 1/2003 | Stinchcomb et al. |
| 2004/0180360 A1 | 9/2004 | Wilson et al. |
| 2004/0197804 A1 | 10/2004 | Keefe et al. |
| 2004/0253679 A1 | 12/2004 | Epstein et al. |
| 2005/0037394 A1 | 2/2005 | Keefe et al. |
| 2005/0045620 A1 | 2/2005 | Hampel et al. |
| 2012/0263648 A1 | 10/2012 | Shapiro et al. |

FOREIGN PATENT DOCUMENTS

| | | | | |
|---|---|---|---|---|
| EP | 1479766 A1 * | 11/2004 | ........... | A61K 9/5115 |
| WO | WO-92/12164 A1 | 7/1992 | | |
| WO | WO-9212164 A1 * | 7/1992 | ............. | B82Y 10/00 |
| WO | WO-2010/148085 A1 | 12/2010 | | |
| WO | WO-2012125987 A2 | 9/2012 | | |
| WO | WO-2013/075140 A1 | 5/2013 | | |
| WO | WO-2013075140 A1 * | 5/2013 | ........... | C12N 15/111 |
| WO | WO-2014039809 A2 | 3/2014 | | |

OTHER PUBLICATIONS

Afonin et al (Methods, vol. 67, pp. 256-265 (Nov. 1, 2013)) (Year: 2013).*
Afonin et al (Nature Nanotechnology, vol. 5, pp. 676-682 (2010)) (Year: 2010).*
Afonin et al (Nucleic Acids Res., vol. 42, No. 3, pp. 2085-2097 (Nov. 4, 2013) (Year: 2013).*
Afonin et al (Nature Nanotechnology, vol. 8, pp. 296-304 (2013)) (Year: 2013).*
Afonin et al, Methods, vol. 67, pp. 256-265. (Year: 2014).*
Shu et al. "Bottom-up Assembly of RNA Arrays and Superstructures as Potential Parts in Nanotechnology," *Nano Letters*, 4(9): 1717-1723 (2004).
Adlakha-Hutcheon et al. "Controlled destabilization of a liposomal drug delivery system enhances mitoxantrone antitumor activity," *Nature Biotech.*, 17: 775-779 (1999).

(Continued)

*Primary Examiner* — Jane J Zara
(74) *Attorney, Agent, or Firm* — Leydig, Voit & Mayer Ltd.

(57) ABSTRACT

The instant invention provides RNA nanocubes, DNA nanocubes and R/DNA chimeric nanocubes comprising one or more functionalities. The multifunctional RNA nanocubes are suitable for therapeutic or diagnostic use in a number of diseases or disorders.

18 Claims, 29 Drawing Sheets
Specification includes a Sequence Listing.

(56) References Cited

OTHER PUBLICATIONS

Afonin et al. "Activation of different split functionalities on re-association of RNA-DNA hybrids," *Nat. Nanotechnol.*, 8: 296-304 (2013).
Afonin "Multifunctional RNA nanoparticles," *Nano Lett.*, 14(10): 5662-71 (2014).
Afonin & Leontis, "Generating new specific RNA interaction interfaces using C-loops," *Journal of the American Chemical Society*, 128(50): 16131-16137 (2006).
Afonin et al. "Co-transcriptional Assembly of Chemically Modified RNA Nanoparticles Functionalized with siRNAs," *Nano letters*, 12: 5192-5195 (2012).
Afonin et al. "Co-transcriptional production of RNA-DNA hybrids for simultaneous release of multiple split functionalities," *Nucleic acids research*, 42(3): 2085-2097 (2014).
Afonin et al. "Design and self-assembly of siRNA-functionalized RNA nanoparticles for use in automated nanomedicine," *Nat. Protoc.*, 6(12): 2022-2034 (2011).
Afonin et al. "In Silico Design and Enzymatic Synthesis of Functional RNA Nanoparticle," *Accounts of Chemical Research*, 47: 1731-1741 (2014).
Afonin et al. "In vitro assembly of cubic RNA-based scaffolds designed in silico," *Nat. Nanotechnol.*, 5(9): 676-682 (2010).
Afonin et al. "Specific RNA self-assembly with minimal paranemic motifs," *Journal of the American Chemical Society*, 130(1): 93-102 (2008).
Afonin et al. "Engineered RNA Nanodesigns for Applications in RNA Nanotechnology" *RNA Nanotechnology*, 1: 1-15 (2013).
Andersen et al. "Self-assembly of a Nanoscale DNA Box with a Controllable Lid," *Nature*, 459: 73-76 (2009).
Bates et al. "Construction and Characterization of a Gold Nanoparticle Wire Assembled Using Mg2+-dependent RNA-RNA Interactions," *Nano Lett.*, 6(3): 445-8 (2006).
Berkhout et al. "Molecular strategies to design an escape-proof antiviral therapy," *Antiviral Res.*, 92: 7-14 (2011).
Binzel et al. "Entropy-Driven One-Step Formation of Phi29 pRNA 3WJ from Three RNA Fragments," *Biochemistry*, 53: 2221-2231 (2014).
Bramsen et al. "Development of Therapeutic-Grade Small Interfering RNAs by Chemical Engineering" *Front Genet.*, 3(154): 1-22 (2012).
Brummelkamp et al. "A System for Stable Expression of Short Interfering RNAs in Mammalian Cells," *Science*, 296: 550-553 (2002).
Chelyapov et al. "DNA Triangles and Self-Assembled Hexagonal Tilings," *Journal of the American Chemical Society*, 126: 13924-5 (2004).
Chen et al. "Progress on RNAi-based molecular medicines," *International Journal of Nanomedicine*, 7: 3971-3980 (2012).
Chen et al. "Synthesis from DNA of a molecule with the connectivity of a cube," *Nature*, 350: 631-633 (1991).
Chworos et al. "Building programmable jigsaw puzzles with RNA," *Science*, 306: 2068-2072 (2004).
Dibrov et al. "Self-assembling RNA Square" *Proc. Natl. Acad. Sci. USA*, 108(16): 6405-6408 (2011).
Dittmer et al. "A DNA-Based Machine That Can Cyclically Bind and Release Thrombin," *Angew. Chem., Int. Ed.*, 43: 3550 (2004).
Douglas et al. "Self-assembly of DNA into nanoscale three-dimensional shapes," *Nature*, 459(7245): 414-418 (2009).
Elbashir et al. "RNA interference is mediated by 21- and 22-nucleotide RNAs," *Genes & Development*, 15: 188-200 (2001).
Elbashir et al., "Duplexes of 21-nucleotide RNAs mediate RNA interference in cultured mammalian cells," *Nature*, 411: 494-498 (2001).
Fire et al. "Potent and specific genetic interference by double-stranded RNA in Caenorhabditis elegans," *Nature*, 391: 806-811 (1998).
Goodman et al. "Reconfigurable, braced, three-dimensional DNA nanostructures," *Nat. Nanotechnol.*, 3: 93-96 (2008).

Grabow et al., "RNA Nanotechnology in Nanomedicine," Chapter 16, Nanomedicine and Drug Delivery New Jersey, Apple Academic Press, 1:208-220 (2013).
Grabow et al. "Self-assembling RNA nanorings based on RNAI/II Inverse Kissing Complexes" *Nano. Lett.*, 11(2): 878-87 (2011).
Grimm et al. "Combinatorial RNAi: a winning strategy for the race against evolving targets?" *Mol. Ther.*, 15: 878-888 (2007).
Guo, "The emerging field of RNA nanotechnology," *Nat. Nanotechnol.*, 5(12): 833-842 (2010).
Guo, "RNA Nanotechnology: Engineering, Assembly and Applications in Detection, Gene Delivery and Therapy," *J. Nanosci. Nanotechnol.*, 5(12): 1964-82 (2005).
Guo, "Construction of Folate-conjugated pRNA of Bacteriophage Phi29 DNA Packaging Motor for Delivery of Chimeric siRNA to Nasopharyngeal Carcinoma Cells" *Gene Ther.*, 13(10): 814-20 (2006).
Hampel et al. "RNA Catalytic Properties of the Minimum (-)sTRSV Sequence," *Biochemistry*, 28: 4929-4933 (1989).
Hampel et al. "'Hairpin' Catalytic RNA model: evidence for helices and sequence requirement for substrate RNA," *Nucleic Acids Research*, 18(2): 299-304 (1990).
Hannon, "RNA Interference," *Nature*, 418: 244-251 (2002).
Hansma et al. "TectoRNA and 'kissing-loop' RNA: Atomic Force Microscopy of Self Assembling RNA Structures" *J Microsc*, 212, (Pt 3), 273-9 (2003).
He, et al. "Hierarchical self-assembly of DNA into symmetric supramolecular polyhedra." *Nature*, 452: 198-201 (2008).
Horiya et al. "RNA Lego: Magnesium-dependent assembly of RNA Building Blocks through Loop-Loop Interactions," *Nucleic Acids Res. Suppl.*, 2: 41-2 (2002).
Horiya et al. "RNA Lego: Magnesium-Dependent Formation of Specific RNA Assemblies through Kissing Interactions," *Chemistry & Biology*, 10: 645-654 (2003).
Haseloff et al. "Simple RNA Enzymes with New and Highly Specific Endoribonuclease Activities," *Nature*, 334: 585-591 (1988).
Hutvagner et al. "RNAi: Nature Abhors a Double-Strand," *Curr. Opin. Genet. Devel.*, 12: 225-232 (2002).
Jaeger et al. "The architectonics of programmable RNA and DNA nanostructures," *Current Opinion in Structural Biology*, 16: 531-543 (2006).
Kasprzak et al. "Use of RNA Structure Flexibility Data in Nanostructure Modeling," *Methods*, 54(2): 239-250 (2011).
Kasprzak et al. "Role of Dynamics in RNA Nanostructure Design," RNA Technology and Therapeutics, Florida, CRC Press, 139-158 (2013).
Kaur et al. "Thermodynamic, Counterion, and Hydration Effects for the Incorporation of Locked Nucleic Acid Nucleotides into DNA Duplexes," *Biochemistry*, 45: 7347-55 (2006).
Khaled et al. "Controllable self-assembly of nanoparticles for specific delivery of multiple therapeutic molecules to cancer cells using RNA nanotechnology," *Nano. Letters*, 5: 1797-1808 (2005).
Khisamutdinov et al. "RNA as a Boiling-Resistant Anionic Polymer Material to Build Robust Structures with Defined Shape and Stoichiometry," *ACS Nano*, 8(5): 4771-4781 (2014).
Kim et al. "In Silico, In Vitro, and In Vivo Studies Indicate the Potential Use of Bolaamphiphiles for Therapeutic siRNAs Delivery," *Mol. Ther. Nucleic Acids*, 2(e80): 1-11 (2013).
Kim et al. "The Role of Salt Concentration and Magnesium Binding in HIV-1 Subtype-A and Subtype-B Kissing Loop Monomer Structures," *J. Biomol. Struct. Dyn.*, 31(5): 495-510 (2013).
Koshkin et al. "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron*, 54: 3607-3630 (1998).
Koyfman et al. "Controlled Spacing of Cationic Gold Nanoparticles by Nanocrown RNA," *Journal of the American Chemical Society*, 127: 11886-7 (2005).
Kuzyk et al. "DNA-based Self-assembly of Chiral Plasmonic Nanostructures with Tailored Optical Response," *Nature*, 483: 311-314 (2012).

(56) References Cited

OTHER PUBLICATIONS

Le et al. "Characterization of Structural Features for Small Regulatory RNAs in *Escherichia coli* Genomes," IEEE Conference on Bioinformatics and Biomedicine, 68-72 (2010).
Lee et al. "The Solution Structure of an RNA Loop-Loop Complex: the ColE1 inverted Loop Sequence," *Structure*, 6(8): 993-1005 (1998).
Lee, H. et al. "Molecularly self-assembled nucleic acid nanoparticles for targeted in vivo siRNA delivery," *Nat. Nanotechnol.*, 7(6): 389-393 (2012).
Lee et al. "Expression of small interfering RNAs targeted against HIV-1 rev transcripts in human cells," *Nat. Biotechnol.*, 19: 500-505 (2002).
Li et al. "An Efficient Thermally Induced RNA Conformational Switch as a Framework for the Functionalization of RNA Nanostructures," *Journal of the American Chemical Society*, 128(12): 4035-40 (2006).
Low et al. "SHAPE-directed discovery of potent shRNA inhibitors of HIV-1," *Mol. Ther.*, 20(44): 820-828 (2012).
Martinez et al. "RNA2D3D: a program for generating, viewing, and comparing 3-dimensional models of RNA," *Journal of Biomolecular Structure & Dynamics*, 25(6): 669-683 (2008).
Mathieu et al. "Six-Helix Bundles Designed from DNA," *Nano Lett.*, 5(4): 661-5 (2005).
McCaffrey et al. "RNA Interference in Adult Mice," *Nature*, 418: 38-39 (2002).
Meyer et al. "Cationic Liposomes Coated with Polyethylene Glycol as Carriers for Oligonucleotides," *Biol. Chem.*, 273(25): 15621-15627 (1998).
Miyagishi et al. "U6 promoter-driven siRNAs with four uridine 3'overhangs efficiently suppress targeted gene expression in mammalian cells," *Nat. Biotechnol.*, 20: 497-500 (2002).
Nasalean et al. "Controlling RNA self-assembly to form filaments," *Nucleic Acids Research*, 34(5): 1381-92 (2006).
Oh et al. "siRNA Delivery Systems for Cancer Treatment," *Adv. Drug Deliv. Rev.*, 61(10): 850-62 (2009).
Ohno et al. "Synthetic RNA-protein complex shaped like an equilateral triangle" *Nat. Nanotechnol*, 6: 116-120 (2011).
Paddison et al. "Short hairpin RNAs (shRNAs) induce sequence-specific silencing in mammalian cells," *Gene Dev.*, 16: 948-958 (2002).
Paliy et al. "Coarse-graining RNA nanostructures for molecular dynamics Simulations," *Phys Biol.*, 7(3):1-23 (2010).
Paliy et al. 8th Annual International Conference on Computational Systems Bioinformatics, vol. 8, Aug. 10-12,Stanford University, Palo Alto, CA. p. 71-79 (2009).
Parisien et al. "The MC-Fold and MC-Sym pipeline infers RNA structure from sequence data," *Nature*, 452: 51-55 (2008).
Papahadjopoulos et al. "Sterically stabilized liposomes: Improvements in Pharmacokinetics and Antitumor Therapeutic Efficacy," *Proc. Nat. Acad. Sci. USA*, 88: 11460-11464 (1991).
Paul et al. "Effective expression of small interfering RNA in human cells," *Nat. Biotechnol.*, 20: 505-508 (2002).
Pecot et al. "RNA interference in the clinic: challenges and future directions," *Nat. Rev. Cancer*, 11(1): 59-67 (2011).
Popenda et al. "Automated 3D structure composition for large RNAs," *Nucleic acids research*, 40(14): e112 (2012).
Qian et al. "A Simple DNA Gate Motif for Synthesizing Large-Scale Circuits," Proceedings of the 14th International Meeting on DNA Computing, pp. 70-89 (2009).
Rose et al. "Functional polarity is introduced by Dicer processing of short substrate RNAs," *Nucleic Acids Research*, 33(13): 4140-4156 (2005).
Rossi et al. "Ribozymes as anti-HIV-1 therapeutic agents: principles, applications, and problems, Aids Research and Human Retroviruses," 8(2): 183-189 (1992).
Rothemund, "Folding DNA to create nanoscale shapes and patterns," *Nature*, 440: 297-302 (Mar. 2006).
Seelig et al. "Enzyme-Free Nucleic Acid Logic Circuits," *Science*, 314: 1585-1588 (2006).
Seeman, "Nanomaterials based on DNA," *Annual Review of Biochemistry*, 79: 65-87 (2010).
Sharp, "RNA interference—2001," *Gene Dev.*, 15: 485-490 (2000).
Shu et al. "Programmable folding of fusion RNA in vivo and in vitro driven by pRNA 3WJ motif of phi29 DNA packaging motor," *Nucleic Acids Research*, 42(2): e10, 1-9 (2014).
Shu et al. "Stable RNA nanoparticles as potential new generation drugs for cancer therapy," *Advanced Drug Delivery Reviews*, 66C: 74-89 (2014).
Shlyahovsky et al. "Logic Gates and Antisense DNA Devices Operating on a Translator Nucleic AcidScaffold," *ACS Nano.*, 3(7): 1831 (2009).
Shukla et al. "A Boost for the Emerging Field of RNA Nanotechnology," *ACS Nano.*, 5: 3405-3418 (2011).
Stetson et al. "Recognition of Cytosolic DNA Activates an IRF3-dependent Innate Immune Response," *Immunity*, 24: 93-103 (2006).
Sui et al. "A DNA vector-based RNAi technology to suppress gene expression in mammalian cells," *Proc. Natl. Acad. Sci. USA*, 99(8): 5515-5520 (2002).
Summerton et al. "Morpholino Antisense Oligomers: Design, Preparation, and Properties," *Antisense & Nucleic Acid Drug Development*, 7: 187-195 (1997).
Sun et al. "Cyclic GMP-AMP Synthase is a Cytosolic DNA Sensor that Activates the Type-I Interferon Pathway," *Science*, 339(6121): 786-791 (2013).
Tuschl "RNA Interference and Small Interfering RNAs," *ChemBioChem*, 2: 239-245 (2001).
Wallace et al. "Hybridization of Synthetic Oligodeoxyribonucleotides to $\phi_x$ 174 DNA: the Effect of Single Base Pair Mismatch," *Nucleic Acids Res.*, 6(11): 3543-3557 (1979).
Whitehead et al. "Silencing or Stimulation? siRNA Delivery and the Immune System," *Annu. Rev. Chem. Biomol. Eng.*, 2: 77-96 (2011).
Yu et al. "RNA interference by expression of short-interfering RNAs and hairpin RNAs in mammalian cells," *Proc. Natl. Acad. Sci. USA*, 99(9): 6047-6052 (2002).
Yurke et al. "A DNA-Fueled Molecular Machine Made of DNA," *Nature*, 406: 605-608 (2002).
Yurke et al. "Using DNA to Power Nanostructures," *Genetic Programming and Evolvable Machines*, 4: 111-122 (2003).
Zamore et al. "RNAi: Double-Stranded RNA Directs the ATP-Dependent Cleavage of mRNA at 21 to 23 Nucleotide Intervals," *Cell*, 101: 25-33 (2000).
Zuker, "Mfold web server for nucleic acid folding and hybridization prediction," *Nucleic Acids Research*, 31(13): 3406-3415 (2003).
Kirill A. Afonin et al: "In vitro assembly of cubic RNA-based scaffolds designed in silico", Nature Nanotechnology, vol. 5, No. 9, Aug. 29, 2010 (Aug. 29, 2010), pp. 676-682—including "Supplementary Information for: In vitro assembly of cubic RNA-based scaffolds designed in silico", Nature Nanotechnology, vol. 5, No. 9, Aug. 29, 2010 (Aug. 29, 2010) pp. 676-682.
Kirill A. Afonin et al: "Computational and experimental characterization of RNA cubic nanoscaffolds", Methods, vol. 67, No. 2, Nov. 1, 2013 (Nov. 1, 2013), pp. 256-265.
Chen J et al: "Synthesis From DNA of a Molecule With the Connectivity of a Cube", Nature, Nature Publishing Group, United Kingdom, vol. 350, No. 6319, Apr. 18, 1991 (Apr. 18, 1991), pp. 631-633.
Microsugar Chang et al: "Aptamer-Conjugated DNA Icosahedral Nanoparticles as a Carrier of Doxorubicin for Cancer Therapy", ACS Nano, vol. 5, No. 8, Aug. 23, 2011 (Aug. 23, 2011), pp. 6156-6163.
Kirill A. Afonin et al: "Triggering of RNA Interference with RNA-RNA, RNA-DNA, and DNA-RNA Nanoparticles", ACS Nano, Dec. 18, 2014 (Dec. 18, 2014).

\* cited by examiner

FIG. 2C
Endosomal co-localization
Nanocube/sixAlexa546 with
EEA1
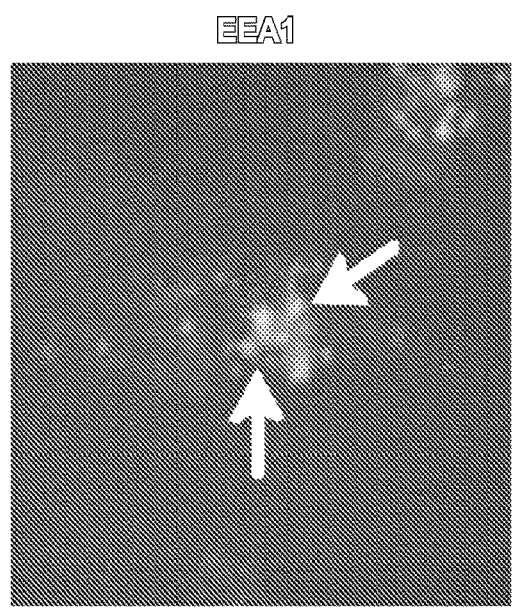
Rab 7
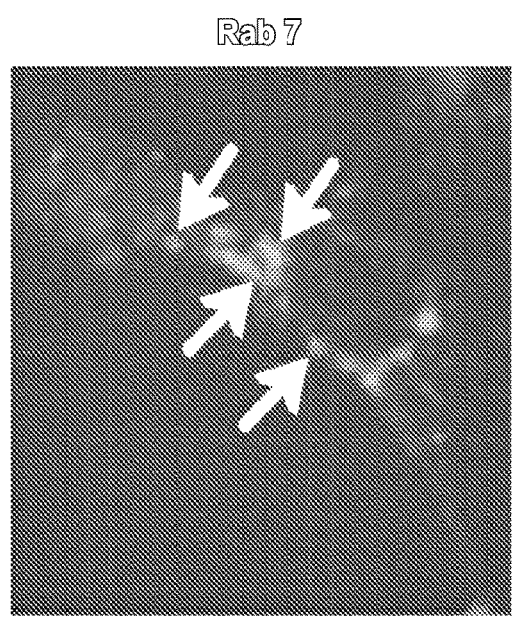

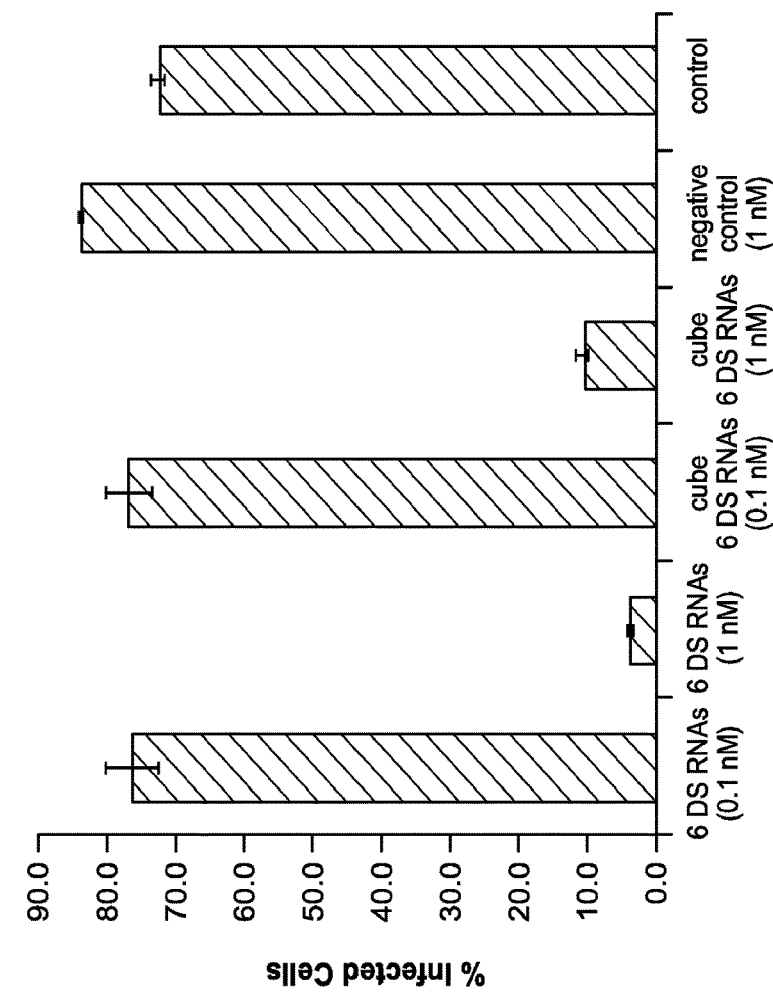
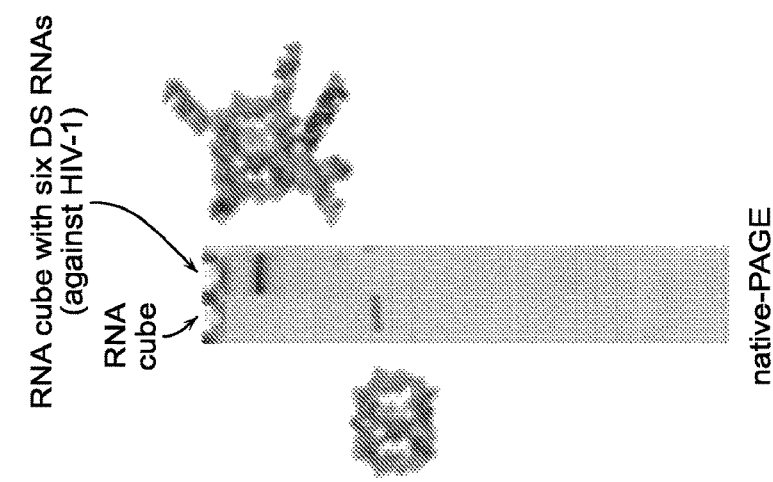
FIG. 3

FIG. 6

RNA cubes[22] 3'-end functionalized with antisense of Dicer substrate RNA (DS RNA) selected against multiple sites of eGFP[23]

Letter sequences below the RNA strands indicate the desired interactions between different strands. Dots indicate the parts of the strands that are per design single-stranded. Sequence characters in upper case represent the cube scaffold. Dicer substrate (DS) RNAs are denoted in lower case.

DS_A
GGCAACUUUGAUCCCUCGGUUUAGCGCCGGCCUUUUCUCCCACACUUUCACGuucggugguca
gaugaacuucaggguca
MMMMMM...KKKKKKLLLL...FFFFFFGGGG...BBBBBBCCCC...NNNN..ZZZZZZZZZZ
ZZZZZZZZZZZZZZZ..
DS_B
GGGAAAUUUCGUGGUAGGUUUUGUUGCCCGUGUUUCUACGAUUACUUUGGUCuucgguggugca
gaugaacuucaggguca
QQQQQQ...PPPPPPPPPP...MMMMMMNNNN...EEEEEEEEEE...RRRR..ZZZZZZZZZZ
ZZZZZZZZZZZZZZZ..
DS_C
GGACAUUUUCGAGACAGCAUUUUUUCCCGACCUUUGCGGAUUGUAUUUUAGGuucgguggugca
gaugaacuucaggguca
IIIIII...OOOOOOOOOO...QQQQQQRRRR...DDDDDDDDDD...JJJJ..ZZZZZZZZZZ
ZZZZZZZZZZZZZZZ..
DS_D
GGCGCUUUUGACCUUCUGCUUUAUGUCCCCUAUUUCUUAAUGACUUUUGGCCuucgguggugca
gaugaacuucaggguca
FFFFFF...HHHHHHHHHH...IIIIIIJJJJ...AAAAAAAAAA...GGGG..ZZZZZZZZZZ
ZZZZZZZZZZZZZZZ..
DS_E
GGGAGAUUUAGUCAUUAAGUUUUACAAUCCGCUUUGUAAUCGUAGUUUGUGUuucgguggugca
gaugaacuucaggguca
BBBBBB...AAAAAAAAAA...DDDDDDDDDD...EEEEEEEEEE...CCCC..ZZZZZZZZZZ
ZZZZZZZZZZZZZZZ..
DS_F
GGGAUCUUUACCUACCACGUUUUGCUGUCUCGUUUGCAGAAGGUCUUUCCGAuucgguggugca
gaugaacuucaggguca
KKKKKK...PPPPPPPPPP...OOOOOOOOOO...HHHHHHHHHH...LLLL..ZZZZZZZZZZ
ZZZZZZZZZZZZZZZ..

DS RNA sense
pACCCUGAAGUUCAUCUGCACCACCG
ZZZZZZZZZZZZZZZZZZZZZZZZZ
DS RNA antisense
CGGUGGUGCAGAUGAACUUCAGGGUCA

FIG. 7

RNA cubes 3'-end functionalized with antisense of dicer substrate RNA (DS RNA) selected against multiple sites of HIV-1[24]

DS_A_ldr
GGCAACUUUGAUCCCUCGGUUUAGCGCCGGCCUUUUCUCCCACACUUUCACGuugacggacucg
cacccaucucucuccuu
MMMMM...KKKKKKLLLL...FFFFFFGGGG...BBBBBBCCCC...NNNN..SSSSSSSSSS
SSSSSSSSSSSSSSS..
DS_B_nef
GGGAAAUUUCGUGGUAGGUUUUGUUGCCCGUGUUUCUACGAUUACUUUGGUCuuggaggaaauu
agcccuuccagucccuu
QQQQQQ...PPPPPPPPPP...MMMMMNNNN...EEEEEEEEEE...RRRR..TTTTTTTTTT
TTTTTTTTTTTTTTT..
DS_C_pro
GGACAUUUUCGAGACAGCAUUUUUUCCCGACCUUUGCGGAUUGUAUUUUAGGuuucuucuaaua
cuguaucaucugcuccu
IIIIII...OOOOOOOOOO...QQQQQQRRRR...DDDDDDDDDD...JJJJ..XXXXXXXXXX
XXXXXXXXXXXXXXX..
DS_D_env
GGCGCUUUUGACCUUCUGCUUUAUGUCCCCUAUUUCUUAAUGACUUUUGGCCuuggacaauugg
agaagugaauuauauu
FFFFFF...HHHHHHHHHH...IIIIIIJJJJ...AAAAAAAAAA...GGGG..ZZZZZZZZZZ
ZZZZZZZZZZZZZZ..
DS_E_gag
GGGAGAUUUAGUCAUUAAGUUUUACAAUCCGCUUUGUAAUCGUAGUUUGUGUuuccuggaaugc
ugucaucauuucuucuu
BBBBBB...AAAAAAAAAA...DDDDDDDDDD...EEEEEEEEEE...CCCC..WWWWWWWWWW
WWWWWWWWWWWWWWW..
DS_F_rt
GGGAUCUUUACCUACCACGUUUUGCUGUCUCGUUUGCAGAAGGUCUUUCCGAuuauuuaucuac
uuguucauuuccucca
KKKKK...PPPPPPPPPP...OOOOOOOOOO...HHHHHHHHHH...LLLL..CCCCCCCCCC
CCCCCCCCCCCCCC..

FIG. 8

Corresponding sense strands
DS ldr
5'-pGGAGAGAGAUGGGUGCGAGUUCGUC
    SSSSSSSSSSSSSSSSSSSSSSSSSS
DS nef
5'-pGGGACUGGAAGGGCUAAUUUUCUCC
    TTTTTTTTTTTTTTTTTTTTTTTTTT
DS pro
5'-pGAGCAGAUGAUACAGUAUUAGAAGA
    XXXXXXXXXXXXXXXXXXXXXXXXXX
DS env
5'-pUAUAAUUCACUUCUCCAAUUGUCC
    ZZZZZZZZZZZZZZZZZZZZZZZZZ
DS gag
5'-pGAAGAAAUGAUGACAGCAUUUCAGG
    WWWWWWWWWWWWWWWWWWWWWWWWWW
DS rt
5'-pGAGGAAAUGAACAAGUAGAUAAAU
    CCCCCCCCCCCCCCCCCCCCCCCCC

FIG. 9

DNA sequences designed for auto-recognizing RNA-DNA hybrids against eGFP[19]

Auto-recognizing toeholds are underlined.

DNA for antisense of eGFP DS RNA (hybrids for assembly with 3`-end functionalized RNA cubes)
Alexa546-<u>GTCACGGTCTCCT</u>GACCCTGAAGTTCATCTGCACCACCG
DNA for sense of eGFP DS RNA (cognate hybrids for 3`-end functionalized RNA cubes)
CGGTGGTGCAGATGAACTTCAGGGTCAGGAGACCGTGAC-Alexa488

DNA cube with three Ts at each corner

A
GGCAACTTTGATCCCTCGGTTTAGCGCCGGCCTTTTCTCCCACACTTTCACG
MMMMMM...KKKKKKLLLL...FFFFFFGGGG...BBBBBBCCCC...NNNN

B
GGGAAATTTCGTGGTAGGTTTTGTTGCCCGTGTTTCTACGATTACTTTGGTC
QQQQQQ...PPPPPPPPPP...MMMMMMNNNN...EEEEEEEEEE...RRRR

C
GGACATTTTCGAGACAGCATTTTTTCCCGACCTTTGCGGATTGTATTTTAGG
IIIIII...OOOOOOOOOO...QQQQQRRRR...DDDDDDDDD...JJJJ

D
GGCGCTTTTGACCTTCTGCTTTATGTCCCCTATTTCTTAATGACTTTTGGCC
FFFFFF...HHHHHHHHHH...IIIIIIJJJJ...AAAAAAAAAA...GGGG

E
GGGAGATTTAGTCATTAAGTTTTACAATCCGCTTTGTAATCGTAGTTTGTGT
BBBBBB...AAAAAAAAAA...DDDDDDDDDD...EEEEEEEEEE...CCCC

F
GGGATCTTTACCTACCACGTTTTGCTGTCTCGTTTGCAGAAGGTCTTTCCGA
KKKKKK...PPPPPPPPPP...OOOOOOOOO...HHHHHHHHHH...LLLL

FIG. 10

DNA cube 5'-end functionalized with auto-recognizing RNA-DNA hybrids carrying sense strand of DS RNA selected against eGFP

Auto-recognizing toeholds are underlined.

A
<u>GGAGACCGTGACCGGTGGT</u>GCAGATGAACTTCAGGGTCAttGGCAACTTTGATCCCTCGGTTTA
GCGCCGGCCTTTTCTCCCACACTTTCACG

B
<u>GGAGACCGTGACCGGTGGT</u>GCAGATGAACTTCAGGGTCAttGGGAAATTTCGTGGTAGGTTTTG
TTGCCCGTGTTTCTACGATTACTTTGGTC

C
<u>GGAGACCGTGACCGGTGGT</u>GCAGATGAACTTCAGGGTCAttGGACATTTTCGAGACAGCATTTT
TTCCCGACCTTTGCGGATTGTATTTTAGG

D
<u>GGAGACCGTGACCGGTGGT</u>GCAGATGAACTTCAGGGTCAttGGCGCTTTTGACCTTCTGCTTTA
TGTCCCCTATTTCTTAATGACTTTTGGCC

E
<u>GGAGACCGTGACCGGTGGT</u>GCAGATGAACTTCAGGGTCAttGGGAGATTTAGTCATTAAGTTTT
ACAATCCGCTTTGTAATCGTAGTTTGTGT

F
<u>GGAGACCGTGACCGGTGGT</u>GCAGATGAACTTCAGGGTCAttGGGATCTTTACCTACCACGTTTT
GCTGTCTCGTTTGCAGAAGGTCTTTCCGA

```
DNA for antisense of eGFP DS RNA (cognate hybrids for 5`-end
functionalized DNA cubes)
TGACCCTGAAGTTCATCTGCACCACCGGTCACGGTCTCC
```

FIG. 11

DNA cube 3'-end functionalized with auto-recognizing RNA-DNA hybrids carrying antisense strand of DS RNA selected against eGFP

A
GGCAACTTTGATCCCTCGGTTTAGCGCCGGCCTTTTCTCCCACACTTTCACGttTGACCCTGAA
GTTCATCTGCACCACCGGTCACGGTCTCC

B
GGGAAATTTCGTGGTAGGTTTTGTTGCCCGTGTTTCTACGATTACTTTGGTCttTGACCCTGAA
GTTCATCTGCACCACCGGTCACGGTCTCC

C
GGACATTTTCGAGACAGCATTTTTTCCCGACCTTTGCGGATTGTATTTTAGGttTGACCCTGAA
GTTCATCTGCACCACCGGTCACGGTCTCC

D
GGCGCTTTTGACCTTCTGCTTTATGTCCCCTATTTCTTAATGACTTTTGGCCttTGACCCTGAA
GTTCATCTGCACCACCGGTCACGGTCTCC

E
GGGAGATTTAGTCATTAAGTTTTACAATCCGCTTTGTAATCGTAGTTTGTGTttTGACCCTGAA
GTTCATCTGCACCACCGGTCACGGTCTCC

F
GGGATCTTTACCTACCACGTTTTGCTGTCTCGTTTGCAGAAGGTCTTTCCGAttTGACCCTGAA
GTTCATCTGCACCACCGGTCACGGTCTCC

DNA for sense of eGFP DS RNA (cognate hybrids for 3`-end
functionalized DNA cubes)
GGAGACCGTGACCGGTGGTGCAGATGAACTTCAGGGTCA

Fluorescently labeled molecules

DS RNA sense 3`-end labeled with Alexa488
pACCCUGAAGUUCAUCUGCACCACCG-Alexa488
ZZZZZZZZZZZZZZZZZZZZZZZZZ
DS RNA antisense 5`-end labeled with Alexa546
Alexa546-CGGUGGUGCAGAUGAACUUCAGGGUCA DNA for antisense of eGFP DS RNA (hybrids for assembly with 3`-
end functionalized RNA cubes) 5`-end labeled with Alexa546
Alexa546-GTCACGGTCTCCTGACCCTGAAGTTCATCTGCACCACCG
DNA for sense of eGFP DS RNA (cognate hybrids for 3`-end
functionalized RNA cubes) 3`-end labeled with Alexa488
CGGTGGTGCAGATGAACTTCAGGGTCAGGAGACCGTGAC-Alexa488

RNA cube functionalized with six DS RNAs

RNA cube functionalized with six RNA-DNA hybrids

DNA cube functionalized with six RNA-DNA hybrids

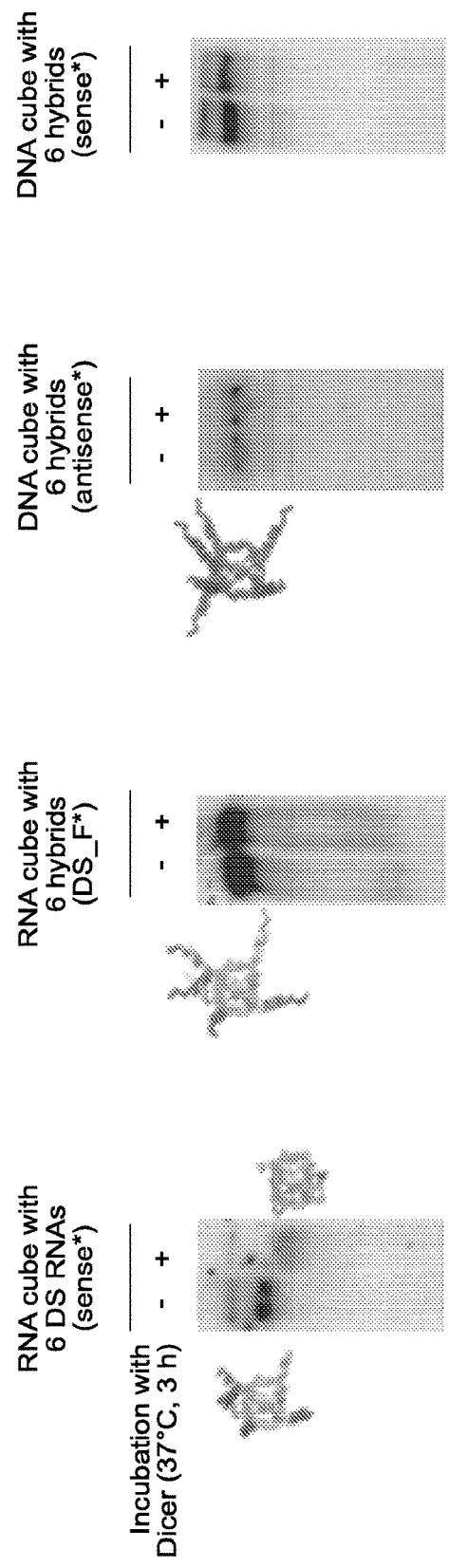
FIG. 13A  *In vitro* dicing of functionalized RNA, RNA-DNA, and DNA-RNA nanoparticles

FIG. 18

| Functional nanoparticle | Cut by Dicer | Stable in blood | Activates IFNs | Activates RNAi |
|---|---|---|---|---|
| RNA nanocube | YES | NO | YES | YES |
| RNA-DNA nanocube | NO | NO | YES | NO* |
| DNA-RNA nanocube | NO | YES | NO | NO* |

\* -- cognate RNA-DNA hybrids are required for activation of RNAi during intracellular re-association.

SEQUENCE LISTING

<160> NUMBER OF SEQ ID NOS: 48

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other
<220> FEATURE:
<221> NAME/KEY: modified_base
<222> LOCATION: (10)..(19)
<223> OTHER INFORMATION: a, c, t, g, unknown or other
<220> FEATURE:
<221> NAME/KEY: modified_base
<222> LOCATION: (23)..(32)
<223> OTHER INFORMATION: a, c, t, g, unknown or other
<220> FEATURE:
<221> NAME/KEY: modified_base
<222> LOCATION: (36)..(45)
<223> OTHER INFORMATION: a, c, t, g, unknown or other
<220> FEATURE:
<221> NAME/KEY: modified_base
<222> LOCATION: (49)..(52)
<223> OTHER INFORMATION: a, c, t, g, unknown or other

<400> SEQUENCE: 1
nnnnnntttn nnnnnnnnnt tnnnnnnnnn nntttnnnnn nnnnntttnn nn            52

<210> SEQ ID NO 2
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: modified_base
<222> LOCATION: (10)..(19)
<223> OTHER INFORMATION: a, c, u, g, unknown or other
<220> FEATURE:
<221> NAME/KEY: modified_base
<222> LOCATION: (23)..(32)
<223> OTHER INFORMATION: a, c, u, g, unknown or other
<220> FEATURE:
<221> NAME/KEY: modified_base
<222> LOCATION: (36)..(45)
<223> OTHER INFORMATION: a, c, u, g, unknown or other
<220> FEATURE:
<221> NAME/KEY: modified_base
<222> LOCATION: (49)..(52)
<223> OTHER INFORMATION: a, c, u, g, unknown or other

<400> SEQUENCE: 2
nnnnnnuuun nnnnnnnnnu uunnnnnnnn nnuunnnnnn nnnnnuuunn nn            52

<210> SEQ ID NO 3
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

```
ggcaacuuug aucccucggu uuagcgccgg ccuuucucc cacacuuuca cguucggugg      60
ugcagaugaa cuucaggguc a                                              81
```

<210> SEQ ID NO 4
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4

```
gggaaauuuc gugguagguu uuguugcccg uguuucuacg auuacuuugg ucuucggugg    60
ugcagaugaa cuucaggguc a                                              81
```

<210> SEQ ID NO 5
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5

```
ggacauuuuc gagacagcau uuuuucccga ccuuugcgga uuguauuuua gguucggugg    60
ugcagaugaa cuucaggguc a                                              81
```

<210> SEQ ID NO 6
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

```
ggcgcuuuug accuucugcu uuauguccc uauuucuuaa ugacuuugg ccuucggugg      60 ugcagaugaa cuucaggguc a                                              81
```

<210> SEQ ID NO 7
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7

```
gggagauuua gucauuaagu uuuacaaucc gcuuuguaau cguaguuugu guuucggugg    60
ugcagaugaa cuucaggguc a                                              81
```

<210> SEQ ID NO 8
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8

```
gggaucuuua ccuaccacgu uuugcugucu cguuugcaga aggucuuucc gauucggugg    60
ugcagaugaa cuucaggguc a                                              81
```

```
<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
acccugaagu ucaucugcac caccg                                              25

<210> SEQ ID NO 10
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
cgguggugca gaugaacuuc aggguca                                            27

<210> SEQ ID NO 11
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ggcaacuuug aucccucggu uuagcgccgg ccuuuucucc cacacuuuca cguugacgga        60
cucgcaccca ucucucuccu u                                                  81

<210> SEQ ID NO 12
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gggaaauuuc gugguagguu uuguugcccg uguuucuacg auuacuuugg ucuuggagga        60
aauuagcccu uccagucccu u                                                  81

<210> SEQ ID NO 13
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ggacauuuuc gagacagcau uuuuucccga ccuuugcgga uuguauuuua gguuucuucu        60
aauacuguau caucugcucc u                                                  81

<210> SEQ ID NO 14
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14
ggcgcuuuug accuucugcu uuaugucccc uauuucuuaa ugacuuuugg ccuuggacaa      60
uuggagaagu gaauuauauu                                                  80

<210> SEQ ID NO 15
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gggagauuua gucauuaagu uuuacaaucc gcuuuguaau cguaguuugu guuccugga      60 augcugucau cauuucuucu u                                                81

<210> SEQ ID NO 16
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gggaucuuua ccuaccacgu uuugcugucu cguuugcaga aggucuuucc gauuauuau      60 cuacuuguuc auuccucca                                                   80

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ggagagagau gggugcgagu ucguc                                            25

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gggacuggaa gggcuaauuu ucucc                                            25

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gagcagauga uacaguauua gaaga                                            25

<210> SEQ ID NO 20
<211> LENGTH: 24
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uauaauucac uucuccaauu gucc                                              24

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gaagaaauga ugacagcauu ucagg                                             25

<210> SEQ ID NO 22
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gaggaaauga acaaguagau aaau                                              24

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtcacggtct cctgaccctg aagttcatct gcaccaccg                              39

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cggtggtgca gatgaacttc agggtcagga gaccgtgac                              39

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggcaactttg atccctcggt ttagcgccgg ccttttctcc cacactttca cg               52

<210> SEQ ID NO 26
<211> LENGTH: 52
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 26
gggaaatttc gtggtaggtt ttgttgcccg tgtttctacg attactttgg tc        52

<210> SEQ ID NO 27
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
ggacattttc gagacagcat tttttcccga cctttgcgga ttgtatttta gg        52

<210> SEQ ID NO 28
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
ggcgcttttg accttctgct ttatgtcccc tatttcttaa tgactttgg cc         52

<210> SEQ ID NO 29
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
gggagattta gtcattaagt tttacaatcc gctttgtaat cgtagtttgt gt        52

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
gggatcttta cctaccacgt tttgctgtct cgtttgcaga aggtctttcc ga        52

<210> SEQ ID NO 31
<211> LENGTH: 93
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
ggagaccgtg accggtggtg cagatgaact tcagggtcat tggcaacttt gatccctcgg        60
tttagcgccg gccttttctc ccacactttc acg                                   93

<210> SEQ ID NO 32
<211> LENGTH: 93

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggagaccgtg accggtggtg cagatgaact tcagggtcat tgggaaattt cgtggtaggt      60
tttgttgccc gtgtttctac gattactttg gtc                                   93

<210> SEQ ID NO 33
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggagaccgtg accggtggtg cagatgaact tcagggtcat tggacatttt cgagacagca      60 tttttttcccg acctttgcgg attgtatttt agg                                  93

<210> SEQ ID NO 34
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggagaccgtg accggtggtg cagatgaact tcagggtcat tggcgctttt gaccttctgc      60
tttatgtccc ctatttctta atgacttttg gcc                                   93

<210> SEQ ID NO 35
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggagaccgtg accggtggtg cagatgaact tcagggtcat tgggagattt agtcattaag      60
ttttacaatc cgctttgtaa tcgtagtttg tgt                                   93

<210> SEQ ID NO 36
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggagaccgtg accggtggtg cagatgaact tcagggtcat tggatctttt acctaccacg      60
ttttgctgtc tcgtttgcag aaggtctttc cga                                   93

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 37
tgaccctgaa gttcatctgc accaccggtc acggtctcc                39

<210> SEQ ID NO 38
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggcaactttg atccctcggt ttagcgccgg cctttctcc cacactttca cgtttgaccc        60
tgaagttcat ctgcaccacc ggtcacggtc tcc                                   93

<210> SEQ ID NO 39
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gggaaatttc gtggtaggtt ttgttgcccg tgtttctacg attactttgg tctttgaccc       60
tgaagttcat ctgcaccacc ggtcacggtc tcc                                   93

<210> SEQ ID NO 40
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggacattttc gagacagcat tttttcccga cctttgcgga ttgtatttta ggtttgaccc      60
tgaagttcat ctgcaccacc ggtcacggtc tcc                                   93

<210> SEQ ID NO 41
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcgcttttg accttctgct ttatgtcccc tatttcttaa tgacttttgg cctttgaccc      60
tgaagttcat ctgcaccacc ggtcacggtc tcc                                   93

<210> SEQ ID NO 42
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gggagattta gtcattaagt tttacaatcc gctttgtaat cgtagtttgt gttttgaccc      60
tgaagttcat ctgcaccacc ggtcacggtc tcc                                    93

<210> SEQ ID NO 43
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gggatcttta cctaccacgt tttgctgtct cgtttgcaga aggtctttcc gatttgaccc       60
tgaagttcat ctgcaccacc ggtcacggtc tcc                                    93

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggagaccgtg accggtggtg cagatgaact tcagggtca                              39

<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
acccugaagu ucaucugcac caccg                                             25

<210> SEQ ID NO 46
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cgguggugca gaugaacuuc aggguca                                           27

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtcacggtct cctgaccctg aagttcatct gcaccaccg                              39

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 48
cggtggtgca gatgaacttc agggtcagga gaccgtgac                              39
```

TRIGGERING RNA INTERFERENCE WITH RNA-DNA AND DNA-RNA NANOPARTICLES

RELATED APPLICATIONS AND INCORPORATION BY REFERENCE

The present application is the U.S. National Phase Entry, pursuant to 35 U.S.C. § 371, of PCT International Application No. PCT/US2015/029553, filed on May 6, 2015. PCT International Application No. PCT/US2015/029553 claims priority to U.S. Provisional Application Ser. No. 61/989,520, filed May 6, 2014, and to U.S. Provisional Application Ser. No. 61/990,094, filed May 7, 2014, the entire contents each of which are incorporated herein by reference in their entireties.

STATEMENT REGARDING FEDERALLY SPONSORED RESEARCH AND DEVELOPMENT

This invention was made with Government support under project numbers ZIA BC00838234 and ZIA BC01106110 by the National Institutes of Health, National Cancer Institute. The Government has certain rights in the invention.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

SEQUENCE LISTING

The instant application contains a Sequence Listing which has been submitted electronically in ASCII format and is hereby incorporated by reference in its entirety. Said ASCII copy, created on Jan. 12, 2017, is named 1420378_426US9_SL.txt and is 14,459 bytes in size.

BACKGROUND OF THE INVENTION

While RNA interference (RNAi) continues to hold incredible potential, numerous challenges associated with the application of RNAi technology must be addressed before it can be made into a viable therapy. The most prominent include transporting, targeting, and stabilizing short interfering RNAs (siRNAs) into tumor cells after injection into a patient's bloodstream. One of the most promising set of solutions to date includes the use of various types of nanoparticles (NPs) (Whitehead et al. 2009; Oh and Park 2009).

The rapidly expanding field of nanobiology opens up the possibilities for the development of new methods and compositions that can be used for the diagnosis, prognosis, and treatment of a multitude of diseases and conditions. However, while an increasing number of novel drugs and therapeutic agents are being discovered, the problem of delivering them specifically to the desired site or cell has not been solved. RNA nanoparticles have been shown to be able to carry multiple components, including molecules for specific cell recognition, image detection, and therapeutic treatment. The use of such protein-free nanoparticles holds the promise for the repeated long-term treatment of chronic diseases with low immune response and should avoid the problems of short retention time of small molecules and the difficulty of delivery of particles larger than 100 nanometers.

For example, NPs can provide several distinct advantages toward the advancement of RNAi therapeutics. For instance, they have been shown to produce a nanoparticle effect that improves cellular uptake. Moreover, NPs offer an increased degree of protection against ribonuclease degradation while also accommodating additional functional groups like aptamers to aid cellular targeting.

While a broad range of materials have been used in RNAi nanotechnology, including some exotic synthetic materials, unmodified RNA nucleotides that serve as both the therapeutic and the structural core of NPs are thought to provide unique advantages. For example, the use of natural RNA nucleotides—in addition to RNA's biocompatibility—takes advantage of RNA's inherent ability to self-assemble and spatially arrange multiple siRNAs, RNA or DNA aptamers, flourescent dyes, small molecules, RNA-DNA hybrids with split functionalities, and proteins. Furthermore, NPs made of unmodified nucleotides can be synthesized directly via run-off transcription, making their ease of synthesis and cost of production attractive for scaled-up production.

Formation of functional RNA NPs has been previously described and can take place either with one-pot assembly or directly with T7 RNA polymerase transcription reactions when equimolar amounts of DNA templates encoding specifically designed RNAs that are part of the composition of the functional RNA NPs (see, e.g. PCT/US2013/058492, incorporated by reference in its entirety herein).

Accordingly, there remains a need in the art for the development of siRNA nanoscaffolds to address several present challenges associated with NP-based siRNA delivery including cell-targeting, ease of synthesis, and triggered activation of therapeutic functionalities, and to provide a safe and efficient nanoparticle needs for the delivery of effective therapeutic and diagnostic siRNAs.

SUMMARY OF THE INVENTION

The present invention is based, at least in part, upon the discovery that RNA-DNA and DNA-RNA hybrid nanocubes consisting of either RNA or DNA cores (composed of a plurality of strands, e.g., 6 strands of RNA or DNA oligonucleotides) with attached RNA-DNA hybrid duplexes may be used to conditionally activate different functionalities whereby the functional entity or molecule, e.g., Dicer Substrate RNAs, or DS RNAs, RNA aptamers, FRET pair of dyes) is split into two RNA-DNA hybrids, i.e., where a first hybrid is associated with the RNA or DNA nanocube, and a second cognate hybrid is a free RNA-DNA hybrid molecule, both of which are inactive in the hybrid state. In preferred embodiments, the DNA component of the DNA-RNA hybrids further comprise single strand DNA "toeholds" which are complimentary as between the nanocube hybrids and the freely existing cognate hybrids and which may interact and trigger the reassociation process when both of the cognate hybrids are present in close proximity. The reassociation process results in strand swapping to form DNA-DNA and RNA-RNA hybrids, thereby releasing the split functionalities and restoring and/or triggering their function (e.g., Dicer processing to trigger RNA interference).

Thus, in one aspect, the present invention relates to using RNA oligonucleotides which self-assemble to form a RNA nanoparticle scaffold, which further comprises RNA oligonucleotide "arms" which are further annealed to cognate DNA oligonucleotides, thereby forming a nanocube structure comprised of an RNA "core" scaffold comprising RNA-DNA hybrid arms. Such RNA nanocubes having RNA-DNA hybrid arms can then be mixed (i.e., allowed to associate) with cognate free DNA-RNA hybrid molecules (where each DNA oligonucleotide strand of the free DNA-RNA hybrid molecule is antisense to the sequence of the DNA sequence of the RNA-DNA sequences of the hybrid arms of the nanocube, and vice versa), with such mixing occurring, for example, in solution, in cell culture, following delivery, etc. Such mixing of RNA nanocubes possessing DNA-RNA hybrid arms with free RNA-DNA molecules can promote dissociation and subsequent annealing of arm structures, resulting in RNA nanocubes having RNA-RNA (dsRNA) arms and free dsDNA molecules, thereby activating the innate functionalities of the ds molecules. For example, in certain embodiments, the reassembled dsRNA arms of the RNA nanocubes can be cleaved by Dicer and serve as active RNAi agents (e.g., siRNAs, including, e.g., DsiRNAs), or otherwise serve to activate the RNA interference pathway. In preferred embodiments, the DNA component of the DNA-RNA hybrids further comprise single strand DNA "toeholds" which are complimentary as between the nanocube hybrids and the freely existing cognate hybrids and which may interact and trigger the reassociation process when both of the cognate hybrids are present in close proximity.

In another aspect, the present invention relates to using DNA oligonucleotides which self-assemble to form a DNA nanoparticle scaffold, which further comprises DNA oligonucleotide "arms" which are further annealed to cognate RNA oligonucleotides, thereby forming a nanocube structure comprised of a DNA "core" scaffold comprising RNA-DNA hybrid arms. Such RNA nanocubes having RNA-DNA hybrid arms can then be mixed (i.e., allowed to associate) with cognate free DNA-RNA hybrid molecules (where each DNA oligonucleotide strand of the free DNA-RNA hybrid molecule is antisense to the sequence of the DNA sequence of the RNA-DNA sequences of the hybrid arms of the nanocube, and vice versa), with such mixing occurring, for example, in solution, in cell culture, following delivery, etc. Such mixing of DNA nanocubes possessing DNA-RNA hybrid arms with free RNA-DNA molecules can promote dissociation and subsequent annealing of arm structures, resulting in DNA nanocubes having DNA-DNA (dsDNA) arms and free dsRNA molecules, thereby activating the innate functionalities of the ds molecules. For example, in certain embodiments, the reassembled free dsRNA molecules can be cleaved by Dicer and serve as active RNAi agents (e.g., siRNAs, including, e.g., DsiRNAs), or otherwise serve to activate the RNA interference pathway. In preferred embodiments, the DNA component of the DNA-RNA hybrids further comprise single strand DNA "toeholds" which are complimentary as between the nanocube hybrids and the freely existing cognate hybrids and which may interact and trigger the reassociation process when both of the cognate hybrids are present in close proximity.

Advantages associated with the inclusion of hybrid arms in an RNA nanocube structure, as compared to entirely RNA nanocubes possessing dsRNA arms, include: reduced immunogenicity, enhanced stability and the functionality of the structures provides the ability to form an initially inactive particle (the RNA scaffold nanocube with hybrid arms) that is then activated for RNAi activity only upon association with a DNA-RNA hybrid molecule that presents strands capable of annealing to corresponding DNA and RNA oligonucleotides of the hybrid arms (where each DNA oligonucleotide strand of the free DNA-RNA hybrid molecule is antisense to the sequence of the DNA sequence of the RNA-DNA sequences of the hybrid arms of the nanocube, and vice versa, therefore driving respective formation of dsDNA and dsRNA duplexes).

Further advantages associated with DNA nanocube scaffolds possessing hybrid arms include: reduced immunogenicity, enhanced stability, a scaffold that can be even more readily labeled (e.g., fluorescently labeled) than an RNA scaffold structure, the functionality of the structures provides the ability to form an initially inactive particle (the DNA scaffold nanocube with hybrid arms) that then releases activated RNAi agents only upon association with a DNA-RNA hybrid molecule that presents strands capable of annealing to corresponding DNA and RNA oligonucleotides of the hybrid arms (where each DNA oligonucleotide strand of the free DNA-RNA hybrid molecule is antisense to the sequence of the DNA sequence of the RNA-DNA sequences of the hybrid arms of the nanocube, and vice versa, therefore driving respective formation of dsDNA and dsRNA duplexes), the fact that such structures release a free dsRNA (e.g., an RNAi agent, e.g., siRNA or DsiRNA).

Accordingly, in a first aspect, the present invention provides a DNA nanocube or RNA nanocube comprising one or more functionalities.

The DNA nanocubes may include at least one single-stranded DNA arm, or at least two single-stranded DNA arms, or at least three single-stranded DNA arms, or at least four single-stranded DNA arms, or at least five single-stranded DNA arms, each of which have the capacity to anneal to a cognate or complimentary RNA oligonucleotide. In preferred embodiments, the DNA component of the DNA-RNA hybrids further comprise single strand DNA "toeholds" which are complimentary as between the nanocube hybrids and the freely existing cognate hybrids and which may interact and trigger the reassociation process when both of the cognate hybrids are present in close proximity.

In other embodiments, the DNA nanocubes may include at least one single-stranded RNA arm, or at least two single-stranded RNA arms, or at least three single-stranded RNA arms, or at least four single-stranded RNA arms, or at least five single-stranded RNA arms, each of which have the capacity to anneal to a cognate or complimentary DNA oligonucleotide. In preferred embodiments, the DNA component of the DNA-RNA hybrids further comprise single strand DNA "toeholds" which are complimentary as between the nanocube hybrids and the freely existing cognate hybrids and which may interact and trigger the reassociation process when both of the cognate hybrids are present in close proximity.

The RNA nanocubes may include at least one single-stranded RNA arm, or at least two single-stranded RNA arms, or at least three single-stranded RNA arms, or at least four single-stranded RNA arms, or at least five single-stranded RNA arms, each of which have the capacity to anneal to a cognate or complimentary DNA oligonucleotide. In preferred embodiments, the DNA component of the DNA-RNA hybrids further comprise single strand DNA "toeholds" which are complimentary as between the nanocube hybrids and the freely existing cognate hybrids and which may interact and trigger the reassociation process when both of the cognate hybrids are present in close proximity.

In other embodiments, the RNA nanocubes may include at least one single-stranded DNA arm, or at least two single-stranded DNA arms, or at least three single-stranded DNA arms, or at least four single-stranded DNA arms, or at least five single-stranded DNA arms, each of which have the capacity to anneal to a cognate or complimentary RNA oligonucleotide. In preferred embodiments, the DNA component of the DNA-RNA hybrids further comprise single strand DNA "toeholds" which are complimentary as between the nanocube hybrids and the freely existing cognate hybrids and which may interact and trigger the reassociation process when both of the cognate hybrids are present in close proximity.

In one embodiment, the functionalities include one or more sense or antisense strands of at least one RNAi agent.

In another embodiment, the nanocube includes six single-stranded DNA arms. Optionally, the nanocube includes six oligonucleotide strands.

In one embodiment, the six oligonucleotide strands are capable of self-assembly into a nanocube when combined in an appropriate solution.

In another embodiment, each of the six oligonucleotide strands includes the following sequence structure: 5'-N6-TTT-N10-TTT-N10-TTT-N10-TTT-N4-3' (SEQ ID NO: 1). Optionally, the 3' end of the sequence structure of at least one of the six oligonucleotide strands is extended with an arm sequence.

In one embodiment, the arm sequence of the extended 3' end of the sequence structure is capable of annealing to a sense or antisense strand of a split RNAi agent. Optionally, the split RNAi agent is a siRNA or DsiRNA.

In one embodiment, all six oligonucleotide strands are extended with arm sequences. Optionally, the arm sequences are capable of annealing to a sense or an antisense strand of a split RNAi agent.

In one embodiment, a split RNAi agent of each arm of the DNA nanocube targets a different target gene sequence.

In one embodiment, the different target gene sequences are viral sequences. Optionally, the different target gene sequences are six different target gene sequences of HIV-1. In a related embodiment, the six different target gene sequences of HIV-1 are target gene sequences of ldr, nef, pro, env, gag and/or rt.

Another aspect of the invention provides an RNA nanocube having RNA oligonucleotide arms, where the RNA oligonucleotide arms are capable of annealing to DNA oligonucleotides.

In one embodiment, the RNA oligonucleotide arms are 25 to 35 or more nucleotides in length.

In another embodiment, the RNA nanocube is annealed to DNA oligonucleotides. Optionally, the DNA oligonucleotides are displaced upon contact with free DNA-RNA hybrid molecules. In a related embodiment, the displacement forms dsRNAs on the RNA oligonucleotide arms of the RNA nanocube.

In one embodiment, the dsRNAs are Dicer substrates.

In another embodiment, the dsRNAs are active RNAi agents.

In one embodiment, the nanocube includes six oligonucleotide strands. Optionally, the six oligonucleotide strands are capable of self-assembly into a nanocube when combined in an appropriate solution. In a related embodiment, each of the six oligonucleotide strands includes the following sequence structure: 5'-N6-UUU-N10-UUU-N10-UUU-N10-UUU-N4-3' (SEQ ID NO:2).

In another embodiment, the 5' or 3' end of the sequence structure of at least one of the six oligonucleotide strands is extended with an arm sequence. Optionally, the arm sequence of the extended 3' end of the sequence structure is a sense or antisense strand of a split RNAi agent.

In one embodiment, the split RNAi agent is a siRNA or DsiRNA.

In another embodiment, all six oligonucleotide strands are extended with arm sequences.

In one embodiment, the arm sequences are a sense or an antisense strand of a split RNAi agent.

In another embodiment, a split RNAi agent of each arm of the RNA nanocube targets a different target gene sequence.

In one embodiment, the arms of the DNA nanocube are annealed to RNA oligonucleotides. Optionally, the DNA-RNA hybrid arms are contacted with RNA-DNA hybrid molecules, resulting in release of dsRNAs.

In one embodiment, the released dsRNAs are active RNAi agents.

In another embodiment, the nanocube of the invention (whether RNA nanocube, DNA-RNA hybrid nanocube or RNA-DNA hybrid nanocube) possesses reduced immunogenicity, enhanced RNAi activity, enhanced stoichiometry or is improved for visualization, as compared to an appropriate control nanoparticle.

Another aspect of the invention provides a method for treating a subject having a disease or disorder treatable with one or more RNAi agents, involving administering a nanoparticle (nanocube) composition of the invention to the subject.

A further aspect of the invention provides a cell including a composition of the invention.

Another aspect of the invention provides a pharmaceutical composition including a composition of the invention.

An additional aspect of the invention provides a kit including a composition of the invention, and directions for its use.

In another aspect, the invention features an R/DNA chimeric arm nanocube comprising one or more functionalities.

In one embodiment, the functionalities comprise one or more agents. In another embodiments, the agents are selected from one or more of the group consisting of: inhibitory nucleic acids, fluorescent dyes, small molecules, RNA-DNA hybrids with split functionalities, split lipase, split GFP, proteins, therapeutic agents and imaging agents. In a related embodiment, the inhibitory nucleic acids are selected from the group consisiting of: siRNAs, RNA or DNA aptamers and ribozymes.

In one embodiment, the one or more agents are the same. In another embodiment, the one or more agents are different.

In another embodiment, a first RNA is complementary to a second RNA and when duplexed forms an siRNA.

In another embodiment, the siRNA inhibits a target RNA. In a further embodiment, the target RNA is one which produces a therapeutically beneficial result when inhibited. In another further embodiment, the target RNA comprises an RNA that encodes a protein involved in a disease process or a portion thereof. In a further related embodiment of any one of the above aspects, the target RNA encodes an apoptosis inhibitor protein. In another further related embodiment of any one of the above aspects, the target RNA is a pathogenic RNA genome, an RNA transcript derived from the genome of the pathogenic agent, or a portion thereof. In one embodiment, the pathogenic agent is a virus, a bacteria, a fungus, or a parasite. In another embodiment, the target RNA is a viral RNA genome or a portion thereof.

The invention also features a composition comprising an RNA NP or R/DNA and/or D/RNA nanocube of any one of the above aspects.

The invention also features a pharmaceutical composition comprising a DNA nanocube, a R/DNA and/or D/RNA nanocube of any one of the aspects of the invention.

In one embodiment, the pharmaceutical composition further comprises a pharmaceutically acceptable excipient, carrier, or diluent.

In another embodiment, the pharmaceutical composition is formulated for the treatment of a disease. In still another embodiment, the pharmaceutical composition is formulated for the treatment of an infection by a pathogenic agent. In another related embodiment, the pathogenic agent is a virus, a bacteria, a fungus, or a parasite.

In another embodiment of any of the above aspects or embodiments, the pharmaceutical composition further comprises a second agent that treats or reduces the symptoms associated with infection by the pathogenic agent.

In one embodiment, the second agent is an anti-viral agent.

In another embodiment, the pharmaceutical composition is formulated for the treatment of a neoplasia.

In another further embodiment, the second agent is an anti-cancer agent.

The invention also features a method of inhibiting or reducing the expression of a target gene in a cell comprising contacting the cell with a therapeutically effective amount of the RNA NP or R/DNA NP of any of the above aspects or embodiments, or the composition of any one of the above aspects or embodiments.

The invention also features a method of killing a pathogen infected cell comprising contacting the cell with a therapeutically effective amount of the RNA nanoparticle (NP) or R/DNA nanoparticle of any one of the above aspects or embodiments or the composition of any one of the above aspects or embodiments.

The invention also features a method of inhibiting replication of a pathogen in a cell comprising contacting the cell with a therapeutically effective amount of the RNA nanoparticle or R/DNA nanoparticle of any one of the above aspects or embodiments or the composition of any one of the above aspects or embodiments.

In one embodiment, the cell is in a subject.

The invention also features a method of reducing pathogenic burden in a subject comprising administering a therapeutically effective amount of the RNA nanoparticle or R/DNA nanoparticle of any one of the above aspects or embodiments or the composition of any one of the above aspects or embodiments In one embodiment, the subject is at risk of developing a pathogenic infection.

In another embodiment, the subject is diagnosed with having a pathogenic infection.

The invention also features a method of treating or preventing a pathogenic infection in a subject comprising administering a therapeutically effective amount of the RNA nanoparticle or R/DNA nanoparticle of any one of the above aspects or embodiments or the composition of any one of the above aspects or embodiments.

In one embodiment, the method reduces the pathogenic burden, thereby treating or preventing the pathogenic infection. In another embodiment, the method induces death in infected cell, thereby treating or preventing the pathogenic infection.

In one embodiment, the subject is a mammal. In another embodiment, the subject is a human.

In one embodiment, the pathogen is a virus, bacteria, fungus, or parasite.

In another embodiment of any one of the above aspects or embodiments, the method further comprises contacting the cell with a therapeutically effective amount of a second therapeutic agent or administering a therapeutically effective amount of the second therapeutic agent to the subject.

In one embodiment, the second therapeutic agent treats the pathogenic infection or the symptoms associated with the pathogenic infection.

The invention also features a method of killing a neoplastic cell comprising contacting the cancer cell with a therapeutically effective amount of the of the RNA nanoparticle or R/DNA nanoparticle of any one of the above aspects or embodiments or the composition of any one of the above aspects or embodiments, thereby killing the neoplastic cell.

The invention also features a method of treating a subject having a neoplasia, the method comprising administering to a subject a therapeutically effective amount of the RNA nanoparticle or R/DNA nanoparticle of any one of the above aspects or embodiments or the composition of any one of the above aspects or embodiments, thereby treating the subject.

In one embodiment, the neoplastic cell is a cancer cell which is present in a solid tumor.

In another embodiment, the method further comprises contacting the cell with a therapeutically effective amount of a second therapeutic agent or administering a therapeutically effective amount of the second therapeutic agent to the subject.

In one embodiment, the second therapeutic agent is an anti-cancer agent.

The invention also features a kit comprising the RNA nanoparticle or R/DNA nanoparticle of any one of the above aspects or embodiments or the composition of any one of the above aspects or embodiments.

In one aspect, the kit further comprises a second therapeutic agent.

In still another aspect, the invention relates to a DNA nanoparticle that is capable of becoming activated for RNAi activity, comprising:

a DNA nanoparticle scaffold comprising two or more DNA oligonucleotides that are capable of self-assembling to form the DNA nanoparticle scaffold, wherein at least one DNA oligonucleotide of the DNA nanoparticle scaffold further comprises an R/DNA single strand arm covalently attached thereto;

a cognate single strand R/DNA molecule that is capable of annealing to the R/DNA single strand arm to form a R/DNA hybrid arm;

wherein the DNA nanoparticle scaffold becomes activated for RNAi activity upon association with free R/DNA hybrid molecules that present strands capable of annealing to corresponding DNA and RNA strands of the R/DNA hybrid arms to form RNA/RNA or DNA/DNA hybrid arms and free RNA/RNA or DNA/DNA hybrid molecules. In preferred embodiments, the DNA component of the R/DNA (i.e., RNA-DNA) hybrids further comprise single strand DNA "toeholds" which are complimentary as between the nanocube hybrids and the freely existing cognate hybrids and which may interact and trigger the reassociation process when both of the cognate hybrids are present in close proximity.

The DNA nanoparticle scaffold in certain embodiments comprises six DNA oligonucleotides that are capable of self-assembling to form the DNA nanoparticle scaffold.

The DNA nanoparticle in certain other embodiments comprises DNA oligonucleotides which are each covalently attached to single strand R/DNA arm.

In other embodiments, the DNA nanoparticles are formed of six self-assembling DNA oligonucleotides comprising the following sequence structure: 5'-N$_6$-TTT-N$_{10}$-TTT-N$_{10}$-TTT-N$_{10}$-TTT-N$_4$-3' (SEQ ID NO: 1).

In yet other embodiments, the single strand R/DNA arms of the DNA nanoparticles are covalently attached at the 3' ends of the DNA oligonucleotides of the DNA nanoparticle scaffold.

In still further embodiments, the DNA nanoparticles have single strand R/DNA arms that are capable of annealing to a sense or antisense strand of a split RNAi agent. The split RNAi agent can be a siRNA or DsiRNA.

In another aspect, the invention provides an RNA nanoparticle that is capable of becoming activated for RNAi activity, comprising:

a RNA nanoparticle scaffold comprising two or more single strand RNA molecules that are capable of self-assembling to form the RNA nanoparticle scaffold, wherein at least one single strand RNA molecule of the RNA nanoparticle scaffold further comprises an R/DNA single strand arm covalently attached thereto;

a cognate single strand R/DNA molecule that is capable of annealing to the R/DNA single strand arm to form a R/DNA hybrid arm;

wherein the RNA nanoparticle scaffold becomes activated for RNAi activity upon association with free R/DNA hybrid molecules that present strands capable of annealing to corresponding DNA and RNA strands of the R/DNA hybrid arms to form RNA/RNA or DNA/DNA hybrid arms and free RNA/RNA or DNA/DNA hybrid molecules. In preferred embodiments, the DNA component of the R/DNA (i.e., RNA-DNA) hybrids further comprise single strand DNA "toeholds" which are complimentary as between the nanocube hybrids and the freely existing cognate hybrids and which may interact and trigger the reassociation process when both of the cognate hybrids are present in close proximity.

The RNA nanoparticle scaffold in certain embodiments comprises six single strand RNA molecules that are capable of self-assembling to form the RNA nanoparticle scaffold.

The RNA nanoparticle in certain other embodiments comprises single strand RNA molecules which are each covalently attached to single strand R/DNA arm.

In other embodiments, the RNA nanoparticles are formed of six self-assembling single strand RNA molecules comprising the following sequence structure: 5'-N$_6$-UUU-N$_{10}$-UUU-N$_{10}$-UUU-N$_{10}$-UUU-N$_4$-3' (SEQ ID NO: 2).

In yet other embodiments, the single strand R/DNA arms of the RNA nanoparticles are covalently attached at the 3' ends of the single strand RNA molecules of the RNA nanoparticle scaffold.

In yet another aspect, the invention relates to a pharmaceutical composition for triggering RNA interference comprising a DNA nanoparticle (comprising R/DNA hybrid arms) described herein and a pharmaceutical excipient, wherein the DNA nanoparticle is in an inactive state until combined with a cognate free R/DNA hybrid molecule that presents strands capable of annealing to corresponding DNA and RNA strands of the R/DNA hybrid arms to form RNA/RNA or DNA/DNA hybrid arms and free RNA/RNA or DNA/DNA hybrid molecules.

In another aspect, the invention relates to a pharmaceutical composition for triggering RNA interference comprising a RNA nanoparticle (comprising R/DNA hybrid arms) described herein and a pharmaceutical excipient, wherein the RNA nanoparticle is in an inactive state until combined with a free R/DNA hybrid molecule that presents strands capable of annealing to corresponding DNA and RNA strands of the R/DNA hybrid arms to form RNA/RNA or DNA/DNA hybrid arms and free RNA/RNA or DNA/DNA hybrid molecules.

In a further aspect, the invention relates to a method for treating a subject having a disease or disorder treatable with one or more RNAi agents, comprising administering a composition comprising a DNA or RNA nanostructure described herein.

Other aspects of the invention are described in, or are obvious from, the following disclosure, and are within the ambit of the invention.

BRIEF DESCRIPTION OF THE DRAWINGS

FIGS. 2A to 2D depict activation of RNAi with RNA nanocubes 3'-side functionalized with six DsiRNAs. (a) Schematics of nanocube formation and release of siRNAs. (b) Cellular uptake of fluorescently labeled cubes was assessed with confocal microscopy and statistically analyzed with flow cytometry experiments. (c) Localization of fluorescently labeled functional nanocubes with commonly used markers for endosomal compartments EEA1 and Rab7. (d) GFP knockdown assays for human breast cancer cells (MDA-MB-231/GFP) which stably expressed enhanced GFP (eGFP). Three days after the transfection of cells with nanocubes (assembly was confirmed by native PAGE), eGFP expression was analyzed with fluorescent microscopy and flow cytometry experiments. As a control, siRNA duplexes against eGFP were assayed.

FIG. 3 depicts assembly of RNA nanocubes functionalized with six different dsRNAs against HIV-1 and infectivity assays. Notably robust knockdown efficacies were observed for nanocube structures.

FIG. 6 shows RNA cube sequences 3'-end functionalized with antisense of Dicer substrate RNA (DsiRNA) targeting eGFP (SEQ ID NOS 3-10, respectively, in order of appearance).

FIG. 7 shows RNA cube sequences 3'-end functionalized with antisense of Dicer substrate RNA (DsiRNA) targeting multiple sites of HIV-1 (SEQ ID NOS 11-16, respectively, in order of appearance).

FIG. 8 shows corresponding sense strand sequences (SEQ ID NOS 17-22, respectively, in order of appearance) for the sequences of FIG. 7.

FIG. 9 shows DNA sequences designed for auto-recognizing RNA-DNA hybrids against eGFP (SEQ ID NOS 23-30, respectively, in order of appearance).

FIG. 10 shows DNA cube sequences 5'-end functionalized with auto-recognizing RNA-DNA hybrids carrying sense strand of DsiRNA selected against eGFP (auto-recognizing toeholds are underlined) (SEQ ID NOS 31-37, respectively, in order of appearance).

FIG. 11 shows DNA cube sequences 3'-end functionalized with auto-recognizing RNA-DNA hybrids carrying anti-sense strand of DsiRNA selected against eGFP (auto-recognizing toeholds are underlined). Fluorescently labeled molecules are also shown (SEQ ID NOS 38-48, respectively, in order of appearance).

In FIG. 12B, DNA oligonucleotide sequences associated with the RNA arms of the RNA nanocube are replaced with RNA oligonucleotide sequences of free DNA-RNA hybrid sequences, resulting in dsRNA arms (now active for RNAi via Dicer cleavage) and release of dsDNAs. In FIG. 12C, RNA oligonucleotide sequences associated with the DNA arms of the DNA nanocube are replaced with DNA oligonucleotide sequences of free DNA-RNA hybrid sequences, resulting in dsDNA nanocube arms and release of dsRNAs (now active for RNAi).

FIGS. 13A and 13B show dicing (a) and blood serum degradation assays (b). Sense or antisense strands were radiolabeled with $[^{32}P]\alpha$-GTP at 3'-sides and "*" indicate radiolabeled strands. Native-PAGE gels were used to identify the dicing products after incubation with Dicer (indicated with "+") for 3 hours at 37° C. and degradation products after incubation with 5% human blood serum at different time points. The dicing of RNA cubes with six DsiRNAs was also demonstrated in Afonin et al.[13]

FIG. 15B shows eGFP knockdown assays for human breast cancer cells (MDA-MB-231/GFP) which stably expressed enhanced GFP (eGFP). Three and six days after the transfection of cells, eGFP expression was statistically analyzed with flow cytometry experiments.

In FIG. 16A, the formation of cubes was confirmed by total SYBR Gold staining native PAGE and DLS experiments. FIG. 16B shows FRET time traces during re-association of fluorescently labeled cubes and hybrids labeled with Alexa488 and Alexa546. In FIG. 16C, fluorescently labeled cubes and hybrids individually associated with L2K prior to mixing were followed by fluorescent time tracing. Please note that L2K forms complexes with cubes and hybrids thus, preventing their re-association. FIG. 16D shows GFP knockdown assays for human breast cancer cells expressing enhanced GFP (MDA-MB-231/GFP). Three and six days after the transfection of cells, eGFP expression was analyzed with flow cytometry experiments. As a control, siRNA duplexes against eGFP were also assayed. Notably, individual hybrids and DNA cubes decorated with hybrids caused no decrease in eGFP production when administered in the respective absence of the other.

in FIG. 17A, THP-1 IFN reporter cells were depleted of cGAS or MAVS by siRNA and differentiated with PMA prior to experiments. Cells were transfected with indicated nucleic acids individually or in combination and secreted alkaline phosphatase activity was measured in culture supernatants 24 hours post-transfection. In FIG. 17B, cell viability was assessed via MTT assay.

FIG. 18 shows the relative differences identified for RNA-, RNA-DNA- and DNA-RNA-based nanoparticles described herein.

DETAILED DESCRIPTION OF THE INVENTION

Figure 1:
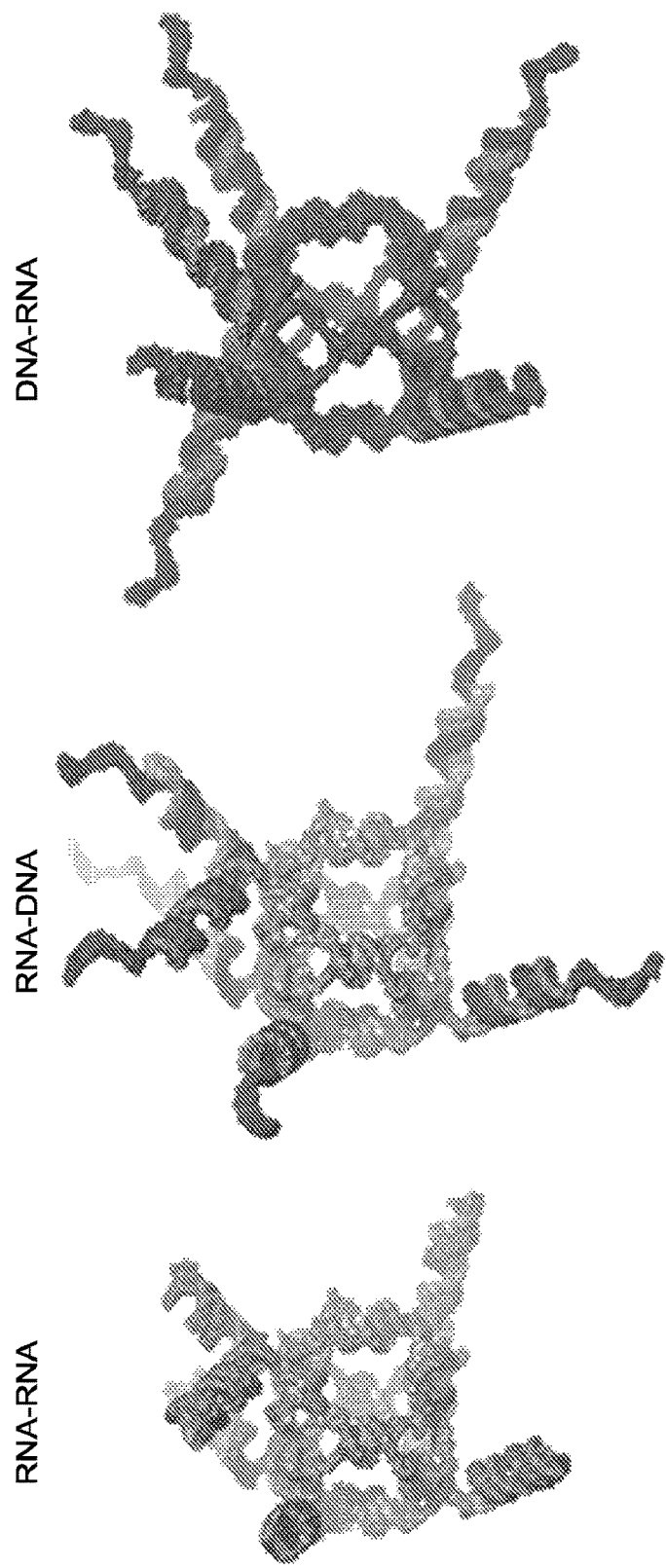
FIG. 1 shows schematics of assemblies of RNA nanocubes and a DNA nanocube, respectively. The RNA nanocube of the left panel is functionalized with six different dsRNA arms, while the RNA nanocube of the middle panel is functionalized with six different RNA-DNA hybrid arms. The DNA nanocube of the right panel is functionalized with six different RNA-DNA hybrid arms. The nanocubes of the middle and right panels are inactive for RNAi in the absence of interaction with free DNA-RNA hybrids that result in strand separation of arms and annealing to antisense DNA and RNA strands, respectively, for DNA and RNA sequences associated with the nanocube structure. In the middle panel, DNA oligonucleotide sequences associated with the RNA arms of the RNA nanocube are replaced with RNA oligonucleotide sequences of free DNA-RNA hybrid sequences, resulting in dsRNA arms (now active for RNAi via Dicer cleavage) and release of dsDNAs. In the right panel, RNA oligonucleotide sequences associated with the DNA arms of the DNA nanocube are replaced with DNA oligonucleotide sequences of free DNA-RNA hybrid sequences, resulting in dsDNA nanocube arms and release of dsRNAs (now active for RNAi).

The present invention is directed, at least in part, to the continued development of RNA and DNA nanoscaffolds in the form of cube structures (e.g., wherein a series of three uracil or three thymine residues form a preferred turn at the corner of a cube structure), which have been designed to address several challenges associated with NP-based siRNA delivery including serum stability, reduced immunogenicity, ease of synthesis, delivery of defined stoichiometries of RNAi agents, and triggered activation of therapeutic functionalities. The instant invention provides RNA and DNA nanocubes comprising one or more functionalities. These functionalized polyvalent RNA and DNA nanocubes are suitable for therapeutic or diagnostic use in a number of diseases or disorders.

The RNA and DNA nanoparticles described herein have the ability to assemble, e.g., self-assemble, into higher order structures, e.g., a nanocube structure. Methods and compositions of RNA nanoparticles that have the ability to assemble are decribed in US Publication US2012 0263648. Specific preparation and assembly of nanocube structures as described herein were recently disclosed in Afonin et al. ("Computational and Experimental Characterization of RNA Cubic Nanoscaffolds" Methods (2014)).

Advantageously, the nanocubes of the instant invention provide a number of improvements over other nanoparticles currently available. For example, the RNA nanocubes of the invention may induce reduced immune responses, as compared to protein nanoparticles currently used, and even in contrast to certain previously described RNA nanoparticles possessing non-cube structures. Indeed, without wishing to be bound by theory, it is initially hypothesized herein that RNA or DNA nanoparticle structure plays a significant role in determining whether an RNA or DNA nanoparticle is immunostimulatory/initiates and interferon and/or PKR response upon admininstration. Thus, the nanocube structures described herein have been observed to be particularly non-immunostimulatory. This is especially true for DNA nanocubes of the invention, which have been found to exhibit significantly reduced levels of immunostimulation, even as compared to RNA nanocubes, and especially as compared to protein nanoparticles and/or RNA nanoparticles previously described.

Moreover, the nanocubes of the invention are small enough to allow for increased efficiency of administration, while also maintaining a fixed stoichiometry of RNAi payloads across the six arms that result in either dsRNA arms active for RNAi in RNA nanocube formats as described herein, or free dsRNAs active for RNAi that are released from DNA nanocube formats described herein. The nanocubes described herein comprise multiple RNA or DNA subunits each of which has the ability to bind an agent. Moreover, multiple different agents can be present within a single nanoparticle. Previous studies have shown that RNA nanostructures are effective drug delivery vehicles (see, for example, Khaled et al. (2005) Nano Letters 5:1797-1808).

The scaffold regions of the nanocubes of the invention also provide surfaces that can be modified with label, e.g., fluorescent labels, for visualization of nanocube localization (e.g., populations of nanocubes were visualized to localize to endosomal structures of mammalian cells in certain experiments described herein).

In addition, both RNA nanocubes possessing RNA-DNA hybrid arms and DNA nanocubes possessing RNA-DNA hybrid arms can be constructed and admistered/delivered in a condition that is inactive for RNAi, yet upon contact with a co-admistered or differentially administered DNA-RNA hybrid molecule (e.g., free DNA-RNA hybrid molecules containing strands that are respectively antisense to corresponding DNA and RNA "sense" arm sequences, respectively), RNAi activity is either imparted to dsRNA arm structures (for RNA nanocube scaffolds) or to dsRNAs released from the arms of DNA nanocube scaffold structures. Thus, RNAi may be both spatially and temporally triggered, depending upon when and where free DNA-RNA hybrids are administered to contact corresponding nanocube structures.

The enhancements to the RNA nanocube system described herein are meant to address several of the challenges remaining in using this technology for a clinical application.

Definitions

The instant invention provides polyvalent RNA nanocubes comprising RNA motifs or DNA motifs, or, in preferred embodiments, both RNA and DNA, as building blocks. The polyvalent RNA nanocubes and polyvalent DNA nanocubes described herein can further comprise therapeutic, diagnostic and/or delivery agents. Further, the polyvalent RNA nanocubes and polyvalent DNA nanocubes described herein can be used as drug delivery compositions to treat various diseases or conditions.

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "administering" is meant to refer to a means of providing the composition to the subject in a manner that results in the composition being inside the subject's body. Such an administration can be by any route including, without limitation, subcutaneous, intradermal, intravenous, intra-arterial, intraperitoneal, and intramuscular.

As used herein, the term "functionalities" refers to substances which are capable of being contained in, or attached, to the nanoparticle. In exemplary embodiments, a functionality is an agent. Exemplary agents include, for example, prodrugs, diagnostic agents, imaging agents, therapeutic agents, chemotherapeutic agents, pharmaceutical agents, drugs, synthetic organic molecules, proteins, peptides, vitamins, and steroids, siRNAs, RNA or DNA aptamers, fluorescent dyes, small molecules, RNA-DNA hybrids with split functionalities, split lipase, split GFP and proteins.

As used herein, an "aptamer" is an oligonucleotide that is able to specifically bind an analyte of interest other than by base pair hybridization. Aptamers typically comprise DNA or RNA or a mixture of DNA and RNA. Aptamers may be naturally occurring or made by synthetic or recombinant means. The aptamers are typically single stranded, but may also be double stranded or triple stranded. They may comprise naturally occurring nucleotides, nucleotides that have been modified in some way, such as by chemical modification, and unnatural bases, for example 2-aminopurine. See, for example, U.S. Pat. No. 5,840,867. The aptamers may be chemically modified, for example, by the addition of a label, such as a fluorophore, or a by the addition of a molecule that allows the aptamer to be crosslinked to a molecule to which it is bound. Aptamers are of the same "type" if they have the same sequence or are capable of specific binding to the same molecule. The length of the aptamer will vary, but is typically less than about 100 nucleotides.

As used herein, the term "therapeutic agent" is meant to refer to an agent that is capable of exerting an effect on a target, in vitro or in vivo.

As used herein, the term "chemotherapeutic agent" is meant to include a compound or molecule that can be used to treat or prevent a cancer. A "chemotherapeutic agent" is meant to include acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-nl; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlomaphazine, novembichin, phenesterine, trofosfamide, estermustine, chlorozotocin, gemzar, nimustine, ranimustine, dacarbazine, mannomustine, mitobronitol,aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara- CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixiimab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

As used herein, the term "effective amount" refers to that amount of a therapeutic agent alone that produces the desired effect (such as treatment of a medical condition such as a disease or the like, or alleviation of a symptom such as pain) in a patient. In some aspects, the phrase refers to an amount of therapeutic agent that, when incorporated into a composition of the invention, provides a preventative effect sufficient to prevent or protect an individual from future medical risk associated with a particular disease or disorder. A physician or veterinarian of ordinary skill can readily determine and prescribe the effective amount of the bioactive agent required to treat and/or prevent the progress of the condition.

As used herein, the term "cancer" is used to mean a condition in which a cell in a subject's body undergoes abnormal, uncontrolled proliferation. Thus, "cancer" is a cell-proliferative disorder. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

The terms "cancer," "neoplasm," and "tumor," are used interchangeably and in either the singular or plural form, refer to cells that have undergone a malignant transformation that makes them pathological to the host organism. By "neoplastic cell" is meant a cell that is a component of a neoplasia.

As used herein, a "composition" refers to the combination of an active agent (e.g., a polyvalent RNA nanoparticle). The composition additionally can comprise a pharmaceutically acceptable carrier or excipient and/or one or more therapeutic agents for use in vitro or in vivo.

As used herein, the term "conjugated" is understood as attached, linked, or otherwise present on a nanoparticle.

As used herein, "disease" is meant to refer to any condition or disorder that damages or interferes with the normal function of a cell, tissue, or organ.

As used herein, "effective amount" is meant to refer to the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects.

In addition, the methods of the invention provide a route for analyzing virtually any number of compounds for effects on a disease described herein with high-volume throughput, high sensitivity, and low complexity.

As used herein, "inhibits neoplasia" is meant decreases the propensity of a cell to develop into neoplasia or slows, decreases, or stabilizes the growth or proliferation of a neoplasia.

As used herein, "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

As used herein, "kits" are understood to contain at least the non-standard laboratory reagents of the invention and one or more non-standard laboratory reagents for use in the methods of the invention.

As used herein, the term "nanoparticle" is meant to refer to a particle between 10 nm and 200 nm in size. A nanoparticle according to the invention comprises a ribonucleic acid (RNA). The RNA can be obtained from any source, for example bacteriophages phi 29, HIV, Drosophila, the ribosome, or be a synthetic RNA.

As used herein, the term "nanocube" is meant to refer to a form of oligonucleotide-based nanoparticle that forms a cube-like structure when the strands comprising the nanocube associate/assemble via annealing. In certain embodiments, a nanocube of the invention is formed by at least six independent oligonucleotide strands that can be either DNA or RNA, and which associate to form the "scaffold" or "core" portion of the nanocube. Optionally, a nanocube of the invention also possesses oligonucleotide "arms" that comprise one strand that is covalently attached to the scaffold region of the cube (and therefore can be considered a component of the nanocube scaffold, even if not forming a part of the cube structure), that scaffold-attached arm being capable of annealing to a complementary single-stranded RNA or DNA oligonucleotide that is not so tethered to the nanocube scaffold structure.

While specific sequences used in the creation of either RNA nanocube scaffolds or DNA nanocube scaffolds are set forth herein, e.g., in FIGS. 6, 7 and 9-11, it is contemplated, as will be recognized by the skilled artisan, that the spacing of nucleotides within oligonucleotide strands that form cube structures, as well as the use of, e.g., three "U" or "T" residues at "corners" of the nanocube structure, are more important to the construction and functionality of an individual nanocube than the precise sequences of the oligonucleotide strands that make up a nanocube of the invention. Indeed, the skilled artisan will recognize that provided that annealing between cognate strands occurs at defined locations of the nanocube, substitution of one nucleotide for another at a given position can be performed without fear of disrupting the nanocube structure. Thus, a broad range of sequences beyond those specifically exemplified herein are contemplated for inclusion within the structure of a nanocube, as ultimately, three dimensional structure is more important to the functionality of the nanocubes described herein than precise sequence.

The term "obtaining" is understood herein as manufacturing, purchasing, or otherwise coming into possession of.

The term "oligonucleotide" as used herein includes linear oligomers of nucleotides or analogs thereof, including deoxyribonucleosides, ribonucleosides, and the like. Typically, oligonucleotides range in size from a few monomeric units, e.g., 3-4, to several hundreds of monomeric units. Olgionucleotides can have inhibitory activity or stimulatory activity.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.,* 15th Ed. (Mack Publ. Co., Easton (1975)).

The term "subject" is intended to include organisms needing treatment. Examples of subjects include mammals, e.g., humans, dogs, cows, horses, pigs, sheep, goats, cats, mice, rabbits, rats, and transgenic non-human animals. In certain embodiments, the subject is a human.

The term "toehold" refers to nucleation site of a domain comprising a nucleic acid sequence designed to initiate hybridization of the domain with a complementary nucleic acid sequence.

As used herein, the term "therapeutic agent" includes a drug and means a molecule, group of molecules, complex or substance administered to an organism for diagnostic, therapeutic, preventative medical, or veterinary purposes. This term includes externally and internally administered topical, localized and systemic human and animal pharmaceuticals, treatments, remedies, nutraceuticals, cosmeceuticals, biologicals, devices, diagnostics and contraceptives, including preparations useful in clinical screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA), ribonucleic acid (RNA), or mixtures or combinations thereof, including, for example, DNA nanoplexes. Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a growth factor, e.g., NGF or GNDF, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

As used herein, the term "treated," "treating" or "treatment" includes the diminishment or alleviation of at least one symptom associated or caused by the state, disorder or disease being treated. A subject that has been treated can exhibit a partial or total alleviation of symptoms (for example, tumor load), or sympotoms can remain static following treatment according to the invention. The term "treatment" is intended to encompass prophylaxis, therapy and cure.

As used here, the phrase "5' or 3' sticky ends" is meant to refer to the 3' and/or 5' protruding ends of DNA or RNA that will bond with complementary sequences of bases. In certain embodiments, the RNA motifs have 5' or 3' sticky ends. In certain embodiments, the 5' or 3' sticky ends are located in the middle of a helix. According to the invention, the 5' and 3' sticky ends can be engineered to be used for self-assembly of nanocube structures.

Other definitions appear in context throughout the disclosure.

RNA and Nanostructure Design

RNA and DNA have a number of advantages for nanostructure design. Nanocube structures provide a size range that is large enough to avoid the problem of expulsion from the cell, but are small enough to avoid the problems of cell delivery often encountered with larger particles. RNA is the only biopolymer that can carry genetic information and has catalytic properties. RNA can naturally fold into complex motifs, and RNA motifs are capable of self-assembly. RNA has a natural functionality, for instance RNA can function as ribozymes or riboswitches. Further, RNA is advantageous in eliciting a very low immune response. Moreover, the construction of RNA into ordered, patterned superstuctures has a number of desirable characteristics, including the ability to self-assemble in precisely defined ways, the ability to undergo editing and replication, the ability to undergo controlled disassembly. RNA has versatility in function and structure. Functionally, RNA is the only biopolymer that can carry genetic information and that possesses catalytic properties. Structurally, RNA has predictable intra and intermolecular interactions with well-known structural geometry. The RNA strands that consist of adenine (A), guanine (G), cytosine (C), and uridine (U) can naturally, or can be programmed, to self-assemble via complementary base pairing. The helical region of RNA has a well-known nanometer scale structural geometry of 2.86 nm per helical turn with 11 base pairs and a 2.3 nm diameter. The self-assembly of RNA into complex structures can be facilitated via complementary base pairing or inter- and intra- molecular interactions of the different single stranded regions in the RNA, including internal bulges and loop motifs, and single-stranded overhangs or "sticky-ends". In addition to Watson-Crick base pairing, A, G, C and T can also pair with other, unconventional bases (i.e. non-canonical base-pairing). For purpose of building nanocube structures, DNA has been identified to possess many of the above-described attributes of RNA.

The methods of the invention can be used to assemble RNA and/or DNA nanocubes composed of six or more strands. E.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122, 123, 124, 125 or more distinct RNA and/or DNA strands.

RNA and DNA Synthesis

RNA molecules and DNA molecules used to make the nanocubes of the invention can be produced recombinantly or synthetically by methods that are routine for one of skill in the art. For example, synthetic RNA molecules can be made as described in US Patent Application Publication No.: 20020161219, or U.S. Pat. Nos. 6,469,158, 5,466,586, 5,281,781, or 6,787,305.

RNA Self-Assembly

Small RNA structural motifs can code the precise topology of large molecular architectures. It has been shown that RNA structural motifs participate in a predictable manner to stabilize, position and pack RNA helices without the need of proteins (Chworos A et al., Science 306:2068-2072.2004). RNAI and RNAII are loop structures that interact in what is called a 'kiss' or 'kissing' complex (Lee et al., Structure 6:993-1005.1998). This contact facilitates the pairing of the RNAI and RNAII loops, until the two RNAs form a duplex. As such, the "kissing" interaction between RNAI and RNAII is one means of self-assembly between the RNA building blocks. The interaction between the RNAIi/RNAIIi complex involves all the bases in the base pairing, and dissociates nearly 7000 times more slowly than the wild-type complex.

The self-assembly of nanoparticles from RNA involves cooperative interaction of individual RNA molecules that spontaneously assemble in a predefined manner to form a larger two- or three-dimensional structure. Within the realm of self-assembly two main categories have been described: template and non-template (Lee et al. J Nanosci Nanotechnol. 2005 December; 5(12):1964-82). Template assembly involves interaction of RNA molecules under the influence of specific external sequence, forces, or spatial constraints such as RNA transcription, hybridization, replication, annealing, molding, or replicas. In contrast, non-template assembly involves formation of a larger structure by individual components without the influence of external forces. Examples of non-template assembly are ligation, chemical conjugation, covalent linkage, and loop/loop interaction of RNA, especially the formation of RNA multimeric complexes (Lee et al. 2005, as above).

Previously, RNA has been demonstrated to assemble into nanoparticles of various shapes and sizes. The first RNA nanoparticles were generated using loop-receptor interfaces to form dimeric nanoparticles. The assembly of this H-shaped nanoparticle was mediated by GAAA/Hnt receptor interaction, which is a highly recurrent motif found in group I and group II introns and other ribozymes and riboswitches. This interaction was further used to generate oriented filaments by combining multiple loop-receptor interactions with a four-way junction motif. One of the first examples of RNA nanoparticles that incorporate multiple RNA motifs within its context is the tectosquare, which is composed of four artificial RNA building blocks called tectoRNAs that self-assemble through specific, non-covalent loop-loop interactions called kissing loops (KL) found at the end of each stem. These tectoRNAs were further programmed to self-assemble into complex arrays via 3' sticky tails with controllable topology, directionality and geometry. The first example of a therapeutic RNA nanoparticle was designed from phi-29-encoded packaging motor (pRNA), a natural RNA motif found in bacteriophages. The pRNA dimers were reengineered for targeted delivery of ribozymes to attack the hepatitis B virus by specifically cleaving the virus's poly-A signal. In a subsequent study, the pRNA trimers were functionalized with cell receptor-binding RNA aptamers and were used to deliver siRNAs that target a specific gene for silencing and thus enabling apoptosis in cancer cells.

In certain embodiments, the RNA and/or DNA building blocks of the invention can self-assemble in buffer conditions suitable for RNA and/or DNA, and that can be determined by one of skill in the art.

In other certain embodiments, the nanocubes of the invention can be formed in a cell. In certain examples, the RNA and/or DNA sequence will be expressed in the cell and formation of the nanocube will be observed via electron microscope tomography (EMT). To satisfy the EMT resolution requirements the minimal size of the nanocube will be between 15 nm, 20 nm, 25 nm, 30, nm, 35 nm, 40 nm, 45 nm or more. In certain embodiments, the minimal size of the nanocube will be 25 nm.

RNA Nanoparticles

RNA has been demonstrated to be an efficient nanoparticle (Afonin et al. RNA Nanotechnology. 1: 1-15, 2013; Kasprzak et al. In: RNA Nanotechnology and Therapeutics. Florida: CRC Press; 2013. p. 139-158; Grabow et al., Recent Advances in Nanoscience and Nanotechnology). Volume 1. New Jersey: Apple Academic Press; 2012. p. 208-220; Shukla et al. ACS Nano. 5: 3405-3418, 2011; Afonin et al. Nat Nanotechnol. 5: 676-82, 2010). A bacteriophage phi29-encoded RNA (pRNA) has been reengineered to form dimmers, trimers, rods, hexamers, and 3D arrays several microns in size through interactions of interlocking loops (Shu, D.; Moll, W.-D.; Deng, Z.; Mao, C.; Guo, P. Nano Letters 2004, 4, (9), 1717-1723; Guo, P. J Nanosci Nanotechnol 2005, 5, (12), 1964-82). A nanoparticle, containing a pRNA trimer as a delivery vehicle was used to deliver siRNAs and receptor-binding aptamers, and has been demonstrated to block cancer development both in vitro in cell culture, and in vivo in mice (Khaled, A.; Guo, S.; Li, F.; Guo, P. Nano Lett 2005, 5, (9), 1797-808; Guo, S.; Huang, F.; Guo, P. Gene Ther 2006, 13, (10), 814-20). An H-shaped RNA molecular unit built from a portion of group I intron domain has been shown to form oriented filaments (Hansma, H. G.; Oroudjev, E.; Baudrey, S.; Jaeger, L. J Microsc 2003, 212, (Pt 3), 273-9; Nasalean, L.; Baudrey, S.; Leontis, N. B.; Jaeger, L. Nucleic Acids Res 2006, 34, (5), 1381-92). Further, specific RNA nano-arrangements based on HIV dimerization initiation site stem-loops were shown to be capable of thermal isomerization to alternative structures (Horiya, S.; Li, X.; Kawai, G.; Saito, R.; Katoh, A.; Kobayashi, K.; Harada, K. Nucleic Acids Res Suppl 2002, (2), 41-2; Horiya, S.; Li, X.; Kawai, G.; Saito, R.; Katoh, A.; Kobayashi, K.; Harada, K. Chem Biol 2003, 10, (7), 645-54.; Li, X.; Horiya, S.; Harada, K. J Am Chem Soc 2006, 128, (12), 4035-40). Small structural fragments found in the ribosome and HIV have been used in the design of artificial RNA building blocks, called tectoRNAs (Chworos, A.; Severcan, I.; Koyfman, A. Y.; Weinkam, P.; Oroudjev, E.; Hansma, H. G.; Jaeger, L. Science 2004, 306, (5704), 2068-72). Each tectoRNA contains a right angle motif that forms a 90-degree angle between adjacent helices, two interacting hairpin loops at the end of each stem, and a 3' "sticky stem". The hairpin loops direct the formation of the tetramer via formation of specific noncovalent loop-loop interactions, called "kissing loops", and the "sticky stems" further assemble tetramers into complex nanoarrays. In bionanotechnology, RNA-RNA interactions can guide precise deposition of gold nanoparticles (Bates, A. D.; Callen, B. P.; Cooper, J. M.; Cosstick, R.; Geary, C.; Glidle, A.; Jaeger, L.; Pearson, J. L.; Proupin-Perez, M.; Xu, C.; Cumming, D. R. Nano Lett 2006, 6, (3), 445-8). Design and self-assembly of siRNA-functionalized RNA nanoparticles for use in automated nanomedicine has been described (Afonin et al. Nat Protoc. 6: 2022-34, 2011). Self-assembling tectoRNA-ladders have been shown to induce a precise linear arrangement of cationic gold nanoparticles, demonstrating that RNA can control regular spacing of gold nanoparticles and can act as a nanocrown scaffold (Koyfman, A. Y.; Braun, G.; Magonov, S.; Chworos, A.; Reich, N. 0.; Jaeger, L. J Am Chem Soc 2005, 127, (34), 11886-7). Activation of different split functionalities on re-association of RNA-DNA hybrids has been described (Afonin et al. Nat Nanotechnol. 8: 296-304, 2013). In Silico, In Vitro, and In Vivo studies have indicatde the potential use of bolaamphiphiles for therapeutic siRNAs Delivery (Kim et al. Mol Ther Nucleic Acids. 2: e80, 2013). A generalized methodology for the one-pot production of chemically modified functional RNA nanoparticles during in vitro transcription with T7 RNA polymerase has been described (Afonin et al. Nano Lett. 12: 5192-5195, 2012). The role of salt concentration and magnesium binding in HIV-1 subtype-A and subtype-B kissing loop monomer structures has been described (Kim et al. J Biomol Struct Dyn. 2013;31(5):495-510).

It is notably contemplated herein that Manganese may be added to T7 reactions to promote use of modified bases within the nanocubes disclosed herein.

Self-assembling RNA nanorings based on RNAI/II inverse kissing complexes have been described (Grabow et al. Nano Lett. 11: 878-87, 2011). RNA structure flexibility data has been used in nanostructure modeling (Kasprzak et al. Methods. 54: 239-250, 2011). Coarse-graining RNA nanostructures have been used for molecular dynamics simulations (Paliy et al. Phys Biol. 7(3): 036001, 2010). Characterization of structural features for small regulatory RNAs in *Escherichia coli* genomes have been reported (Le et al. IEEE Conference on Bioinformatics and Biomedicine, BIBM 2010). Computational and experimental RNA nanoparticle design has been reported (Severcan et al. In: Automation in Genomics and Proteomics: An Engineering Case-Based Approach), and a mesoscopic model for molecular dynamics studies of RNA nanostructures has been described (Paliy et al. 8th Annual International Conference on Computational Systems Bioinformatics Volume 8. Aug. 10-12, 2009; Stanford University, Palo Alto, Calif. p. 71-79).

Design

The general approach used to create RNA, or now DNA and/or RNA-DNA hybrid, nano-particles and nano-materials is to take known RNA and/or DNA structures, cut them into the building blocks, and reengineer single-stranded loops and regions to facilitate the desired self-assembly. The self-assembly of all the above discussed RNA and/or DNA building blocks into nanostructures is mediated by the complementarity of oligonucleotide regions such as hairpin loops and loop receptors that form non-covalent RNA-RNA, RNA-DNA and/or DNA-DNA interactions, as well as by certain sections that simply are capable of annealing (e.g., the hybridized sequences that form a given side of a core structure and the single-stranded region that forms the "corner" of a cube structure—such corners generally comprise a series of three uracil or three thymine residues in the nanocubes set forth herein. For precise assembly of the RNA and/or DNA building blocks, each of the corresponding complementary interactions (e.g., loop-loop interactions) are uniquely reengineered.

Two main experimental approaches are used for programmable self-assembly of nucleic acids nanostructures (Jaeger, L.; Chworos, A. Curr Opin Struct Biol 2006, 16, (4), 531-43). The first is a single-step assembly, which is commonly used for DNA nanostructures (Chelyapov, N.; Brun, Y.; Gopalkrishnan, M.; Reishus, D.; Shaw, B.; Adleman, L. J Am Chem Soc 2004, 126, (43), 13924-5; Mathieu, F.; Liao, S.; Kopatsch, J.; Wang, T.; Mao, C.; Seeman, N. C. Nano Lett 2005, 5, (4), 661-5.). The second is a stepwise assembly, which has been commonly described for RNA nanostructures (Chworos, A.; Severcan, I.; Koyfman, A. Y.; Weinkam, P.; Oroudjev, E.; Hansma, H. G.; Jaeger, L. Science 2004, 306, (5704), 2068-72). In the single-step assembly approach, all molecules are mixed together followed by the slow cool annealing procedure. This is only possible if the target building block structure is the one that has the highest number of Watson-Crick base pairs and is therefore the most stable. However, it is understood that thermodynamic stability of different shapes of nanoparticles is also an important consideration, at times more so than Watson base pairing. This approach is, thus, based on the preferential folding of the building blocks at higher temperatures followed by the self-assembly of these building blocks through weaker interactions into final nanostructures at lower temperatures. However, usually there are many other possible structures that are only slightly less stable. In this case, the stepwise approach can be used where the building blocks are separately formed in the first step are then mixed together in the presence of high magnesium (Mg++) concentration to form a final nanostructure. This approach is more time consuming and the melting temperatures of the building blocks and the final nanostructure should be well separated.

A number of RNA motifs are available as building blocks, including but not limited to RNA I and/or RNA II motifs, kissing loops, RNA I inverse (RNA Ii) and/or RNA II inverse (RNA Hi) motifs. As used herein, the term "motif" in reference to a nanoparticle is meant to refer to a double-stranded or single-stranded ribonucleic acid or analog thereof. Individual motifs are joined together into larger particles by attachment to each other. Attachment can occur by non-covalent linking. Numerous high-resolution RNA structures determined by NMR or X-ray crystallography can be separated into building blocks for design of new RNA nanoparticles and nanomaterials. U.S. application Ser. No. 13/378,985, incorporated by reference in its entirety herein, describes methods of making RNA nanoparticles.

Preferred RNA and/or RNA-DNA and/or DNA nanoparticles comprising one or more functionalities according to the invention are in the shape of a cube; however it is to be understood that other geometries are possible. In certain embodiments, there is a positive relationship between the stability of RNA and/or DNA assemblies and the complexity of the tertiary structures that define the assembly. In certain additional embodiements, there is a positive relationship between assemblies of oligonucleotide strands that form a nanocube structure and correspondingly reduced levels of induction of an immune response, likely due to the geometric structure possessing reduced ability to induce an immune response in a subject.

R/DNA hybrids

In certain embodiments, the present invention splits the functionality of Dicer substrates siRNA duplexes into two R/DNA hybrids (one in the form of a nanocube arm and the other optionally as a free R/DNA hybrid molecule in solution), which upon simultaneous presence inside the same cell (optionally a diseased cell) will recognize each other—optionally through toehold interaction—and re-associate, releasing active siRNAs. This approach can overcome several challenges associated with the clinical delivery of RNAi, such as intravascular degradation (will be reduced for RNA-DNA hybrid nanocubes and particularly DNA-RNA hybrid nanocubes), tissue specificity (DNA chemistry is more parsimonious than RNA and amenable to chemical modifications with different features for targeting or delivery), pharmacodynamics (fluorescent tags can be activated upon R/DNA hybrid re-association (e.g., association of a labeled DNA nanocube scaffold arm with a cognate DNA oligonucleotide, thereby releasing an antisense RNA oligonucleotide in the process, that might then anneal with a cognate RNA oligonucleotide also free in solution, to produce an active dsRNA), assisting in Föorster resonance energy transfer (FRET) imaging of delivery and response). Moreover, all these additional functionalities can be introduced through chemical modifications of the DNA strands in the DNA scaffold structures or in the R/DNA hybrids, thereby not interfering with the processivity of the released siRNAs. Additionally, the number of these functionalities can be at least as large as twice the number of DNA strands entering into the composition of the duplex hybrids or more complex hybrid nanostructures. R/DNA hybrids are described in PCT/US2012/065945, filed Nov. 19, 2012, and incorporated by reference in its entirety herein.

Using RNA interference (RNAi) as a therapeutic agent, it is routinely possible to knock down the expression of target genes in diseased cells. One of the ways to initiate the RNAi machinery is through the direct exogenous introduction to the cells of small interfering RNA (siRNA) duplexes. In certain embodiments, the invention provides for a strategy based on therapeutic RNA-DNA hybrid nanocubes and/or DNA-RNA hybrid nanocubes, which can be generally used for triggering the RNAi pathway as well as other functionalities inside the diseased cells. Individually, each of the hybrid nanocubes is functionally inactive and the therapeutic siRNA representation can only be activated by the re-association of at least two cognate hybrids simultaneously present in the same environment, e.g., in the same cell. The invention features a method for siRNA release where cognate hybrids are co-delivered to an environment or cell either on the same or on two different days. The invention provides for nucleic acids based "smart" nanoparticles for biomedical applications.

In certain embodiments, the design rationale of R/DNA hybrid arms of the nanocubes described herein is the following: functional siRNAs (optionally DsiRNAs, which are indeed preferred for nanocubes possessing an RNA scaffold structure) are split between two R/DNA hybrids preventing them from being diced and thus, making them non-functional. Additionally, it has been shown that substitution of one or both siRNA strands with DNA completely eradicates RNAi. Next, each of the hybrid DNA strands is decorated with a complementary toehold required for hybrid re-association, resulting in Dicer substrate siRNA release from the nanocube arms.

Toehold Interaction

The rates of strand exchange reactions can be increased 106-fold by using toehold-mediated strand displacement (Yurke, et al. Nature 2000, 406, 605; Yurke et al. Genet. Program. Evol. Mach. 2003, 4, 111). Hybridization of the invading strand is initiated at a short singlestranded "toehold" domain attached to one end of the substrate, leading to a branch migration reaction that displaces the target strand from the substrate. In the implementation demonstrated by Yurke and co-workers (Yurke et al. 2000; Yurke et al. 2003) and now widely adopted (Dittmeret al. Angew. Chem., Int. Ed. 2004, 43, 3550; Seelig, G.et al. Science 2006, 314, 1585; Qian et al Proceedings of the 14th International Meeting on DNA Computing; Goel et al. Eds.; Springer: Berlin, 2009; Vol. 5347, pp 70-89; Shlyahovsky et al. ACS Nano 2009, 3, 1831), the toehold and displacement domains are adjacent to each other with no intervening spacer: this simple architecture is referred to as "proximal". A proximal toehold functions both as an address tag and as a means to control the strand-displacement rate and equilibrium.

The term "toehold" refers to nucleation site of a domain comprising a nucleic acid sequence designed to initiate hybridization of the domain with a complementary nucleic acid sequence. The secondary structure of a nanoparticle may be such that the toehold is exposed or sequestered. For example, in some embodiments, the secondary structure of the toehold is such that the toehold is available to hybridize to a complementary nucleic acid (the toehold is "exposed," or "accessible"), and in other embodiments, the secondary structure of the toehold is such that the toehold is not available to hybridize to a complementary nucleic acid (the toehold is "sequestered," or "inaccessible"). If the toehold is sequestered or otherwise unavailable, the toehold can be made available by some event such as, for example, the opening of the hairpin of which it is a part of. When exposed, a toehold is configured such that a complementary nucleic acid sequence can nucleate at the toehold.

A scheme of re-association for the hybrids is described in PCT/US2012/065945, Filed Nov. 19, 2012, and incorporated by reference in its entirety herein. The complementary single-stranded unzipped toeholds in R/DNA hybrids are designed using Mfold (Zuker, M, Nucleic Acids Res 31, 3406-3415 (2003)) to avoid any stable secondary structures. In order to exceed a melting temperature (Tm) of 37° C., the minimal length of the unzipped toeholds with GC content ≥60% should be at least 12 nucleotides (nts). The Tm for designed single stranded toeholds is estimated to be ~40° C. using the Wallace rule (Wallace, R. B. et al., Nucleic Acids Res 6, 3543-3557 (1979)).

Conjugation to Nanocubes

Polyvalent RNA and/or DNA nanocubes comprising one of more functionalities can be used to deliver agents. For example, polyvalent RNA nanocubes, RNA-DNA hybrid nanocubes or DNA-RNA hybrid nanocubes comprising one or more functionalities can be used to deliver one or more agents that are selected from one or more of the group consisting of: siRNAs, RNA or DNA aptamers, fluorescent dyes, small molecules, RNA-DNA hybrids with split functionalities, split lipase, split GFP, proteins, therapeutic agents and imaging agents.

The compositions of the present invention have therapeutic uses. Any number of diseases or disorders can be treated by the compositions of the present invention and may be limited, in fact, only by the agent or agents that can be loaded in the inside of the nanoparticle or conjugated to the outside.

For example, RNA or DNA NPs (e.g., DNA hybrid nanocubes and RNA nanocubes, including RNA-DNA hybrid nanocubes) can be engineered to carry multiple siRNAs against different disease targets. In one exemplary embodiment, six different siRNAs against different parts of the HIV-1 genome can be used for combinatorial RNAi therapy (see, e.g., FIG. 3 herein, where functional efficacy of a nanocube possessing six different siRNAs targeting HIV-1 was shown to be effective at knockdown). The invention is not limited HIV, or to any disease or group of diseases, but is rather defined by the siRNAs that can be used to treat particular diseases. This concept of targeting a specific pathway upon the presence of a particular RNA in the cytoplasm can be applied to cancer (including cancer stem cells) or RNA viruses in general (e.g. Flaviviruses, Alphaviruses). HAART therapy as it currently exists, can successfully suppress virus replication within the human host. With this approach, however, it is currently not possible to eradicate the HIV virus from an infected patient because approved HIV drugs act as virus suppressors and do not kill human cells that are infected by the virus. The present invention can also lead to a novel anti-viral drug that has the unique feature of selectively killing HIV infected cells using appropriate aptamers, for cell targeting, that are associated with RNA NPs containing specific siRNAs or RNA/DNA siRNA hybrids. The guide strands are designed to be an antisense to human apoptosis inhibitor genes (BCL-2, FLIP, STAT3, XIAP, SURVIVIN, etc). Thus, the activation of RNAi (RNA interference pathway) will result in apoptosis of the HIV-infected cell. In addition, in a more general sense, the siRNA targets may include cancer related genes, for example, but not limited to, the hypoxia pathway: Hif1alpha, VEGF; DNA repair pathway: PARP; microRNAS: miR21, miR7, mIR128a, mIR210; cancer stem cells: genes in NOTCH, HEDGEHOG, PTEN, WNT, TGFbeta pathways; immune modulation: Interleukin (IL-6, IL-10) and genes in the JAK/STAT, SMAD, TNFalpha. In principle the concept can be expanded to include any genetically related diseases.

Exemplary potential applications of multi-functional nanoparticles of the invention in which 2, 3, 4, 5, 6 or more independent agents are coupled to a nanoparticle include using one or more agents to target a macromolecular structure or a cell and using the second one to alter the function/properties of the macromolecule or cell, e.g., using a protein to target a cell and using a toxin or cell death protein to kill the targeted cell, using an siRNA to silence genes, or using a fluorescent particle for visualization, or using a chemical or protein to target a protein within a complex and another one to alter the function of a different component of the complex.

In certain embodiments, the nanoparticle comprises one or more agents. In further preferred embodiments, the agent can be conjugated to the nanoparticle. Conjugated can be understood as attached, linked, mixed, or otherwise present on or in a magnetoliposome. For example, an agent can be conjugated by covalent or ionic linkage, by use of a chelate or other linker moiety. As used herein, conjugation of an agent to a nanoparticle does not disrupt the desired activity of the agent.

The agent can comprise any material or compound or composition or agent for in vivo or in vitro use for imaging, diagnostic or therapeutic treatment that can be enclosed in the inside the nanoparticle or can be conjugated with the nanoparticle without appreciably disturbing the physical integrity of the nanoparticle. A nanoparticle can comprise one or more agents of one or more types. For example, a nanoparticle can comprise a therapeutic agent, and the targeting of the agent can be followed by further conjugation with an imaging agent. Similarly, cocktails of therapeutic agents are typically used in the treatment of cancer. A nanoparticle can comprise more than one type of therapeutic agent.

Examples of agents include inhibitory nucleic acids, including but not limited to siRNAs, RNA or DNA aptamers, fluorescent dyes, small molecules, RNA-DNA hybrids with split functionalities, split lipase, split GFP, proteins, therapeutic agents and imaging agents (for example gadolinium, manganese, chromium, or iron).

In certain embodiments, the NP molecules described herein operate by forming inhibitory nucleic acid molecules once in target cells. Such inhibitory nucleic acids include single and double stranded nucleic acid molecules (e.g., DNA, RNA, and analogs thereof) that bind a nucleic acid molecule that encodes target RNA (e.g., antisense oligonucleotide molecules, siRNA, shRNA) as well as nucleic acid molecules that bind directly to a target polypeptide to modulate its biological activity (e.g., aptamers).

Catalytic RNA molecules or ribozymes that include an antisense target RNA sequence of the present disclosure can be used to inhibit expression of target RNAs in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference The disclosure also features a catalytic RNA molecule that includes, in the binding arm, an antisense RNA having between eight and nineteen consecutive nucleobases. In preferred embodiments of this disclosure, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the disclosure and those skilled in the art will recognize that all that is important in an enzymatic nucleic acid molecule of this disclosure is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above. siRNA By "siRNA" is meant a double stranded RNA. Optimally, an siRNA is 18, 19, 20, 21, 22, 23, 24, 25, 26, 27, 28, 29, 30, 31, 32, 33, 34, 35 or more nucleotides in length and has a 2 base overhang at its 3' end. It is understood that the term "siRNA" includes both diceable and non-diceable siRNAs. These dsRNAs can be introduced to an individual cell or to a whole animal; for example, they may be introduced systemically via the bloodstream. Such siRNAs are used to downregulate mRNA levels or promoter activity. Functional siRNAs can be released by Dicer nuclease. Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference), as are twenty-five to thirty nucleotide Dicer substrate dsRNAs (DsiRNAs; Rossi et al. U.S. Pat. No. 8,084,599). The therapeutic effectiveness of an siRNA approach in mammals was demonstrated in vivo by McCaffrey et al. (Nature 418: 38-39, 2002).

Given the sequence of a target gene, siRNAs may be designed to inactivate that gene. Such siRNAs, for example, could be administered directly to an affected tissue, or administered systemically. The nucleic acid sequence of an Parl gene can be used to design small interfering RNAs (siRNAs). The 21 to 25 nucleotide siRNAs (or, optionally 25 to 30 nucleotide or longer DsiRNAs) may be used, for example, as therapeutics to inhibit disease related genes.

The inhibitory nucleic acid molecules of the present disclosure may be employed as double-stranded RNAs for RNA interference (RNAi)-mediated knock-down of target RNA expression. In therapeutic embodiments, the target RNA is a disease related gene. For example, in a non-limiting embodiment, the target RNA is a gene that is involved in HIV. IN another embodiment, the target RNA gene is a gene that is involved in cancer development or progression. In another embodiment, target RNA expression is reduced in a virus infected cell. In another embodiment, the target RNA encodes apoptosis inhibitor proteins and the cells are infected with HIV. RNAi is a method for decreasing the cellular expression of specific proteins of interest (reviewed in Tuschl, Chem Bio Chem 2:239-245, 2001; Sharp, Gene Dev 15:485-490, 2000; Hutvagner and Zamore, Curr Opin Genet Devel 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the disclosure, a double-stranded RNA (dsRNA) molecule is made that includes between eight and nineteen consecutive nucleobases of a nucleobase oligomer of the disclosure. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to 30 or more nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Gene Dev 16:948-958, 2002. Paul et al. Nat Biotechnol 20:505-508, 2002; Sui et al. Proc Natl Acad Sci USA 99:5515-5520, 2002; Yu et al. Proc Natl Acad Sci USA 99:6047-6052, 2002; Miyagishi et al. Nat Biotechnol 20:497-500, 2002; and Lee et al. Nat Biotechnol 20:500-505, 2002, each of which is hereby incorporated by reference. In certain embodiments, the sense strand of the double stranded siRNA is split into two smaller oligonucleotides, also referred to as three stranded siRNA.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above. The invention encompasses stabilized R/DNA NPs having modifications that protect against 3' and 5' exonucleases as well as endonucleases. Such modifications desirably maintain target affinity while increasing stability in vivo. In various embodiments, R/DNA NPs of the invention include chemical substitutions at the ribose and/or phosphate and/or base positions of a given nucleobase sequence. For example, R/DNA NPs of the invention include chemical modifications at the 2' position of the ribose moiety, circularization of the aptamer, 3' capping and 'spiegelmer' technology. R/DNA NPs having A and G nucleotides sequentially replaced with their 2'-OCH3 modified counterparts are particularly useful in the methods of the invention. Such modifications are typically well tolerated in terms of retaining affinity and specificity. In various embodiments, R/DNA NPs include at least 10%, 25%, 50%, or 75% modified nucleotides. In other embodiments, as many as 80-90% of the R/DNA NPs' nucleotides contain stabilizing substitutions. In other embodiments, 2'-OMe containing R/DNA NPs are synthesized. Such R/DNA NPs are desirable because they are inexpensive to synthesize and natural polymerases do not accept 2'-OMe nucleotide triphosphates as substrates so that 2'-OMe nucleotides cannot be recycled into host DNA. Using methods described herein, R/DNA NPs will be selected for increased in vivo stability. In one embodiment, R/DNA NPs having 2'-F and 2'-OCH3 modifications are used to generate nuclease resistant aptamers. In other embodiments, the nucleic acids of the invention have one or more locked nucleic acids (LNA). LNA refers to a modified RNA nucleotide. The ribose of the LNA is modified with an extra bridge connecting the 2' oxygen and the 4' carbon which locks the ribose into the North or 3'-endo conformation. See e.g., Kaur, H. et al., Biochemistry, vol. 45, pages 7347-55; and Koshkin, A. A., et al., Tetrahedron, vol. 54, pages 3607-3630. In other embodiments, one or more nucleic acids of the invention incorporate a morpolino structure where the nucleic acid bases are bound to morpholine rings instead of deoxyribose rings and are linked through phosphorodiamidate groups instead of phosphates. See eg., Summerton, J. and Weller, D., Antisense & Nucleic Acid Drug Development, vol. 7, pages 187-195. Yet other modifications, include (PS)-phosphate sulfur modifications wherein the phosphate backbone of the nucleic acid is modified by the substitution of one or more sulfur groups for oxygen groups in the phosphate backbone. Other modifications that stabilize nucleic acids are known in the art and are described, for example, in U.S. Pat. No. 5,580,737; and in U.S. Patent Application Publication Nos. 20050037394, 20040253679, 20040197804, and 20040180360.

The agent may be a RNA or DNA aptamer. An aptamer is a stable DNA, RNA, or peptide that binds with high affinity and specificity to targets such as small organics, peptides, proteins, cells, and tissues. Unlike antibodies, some aptamers exhibit stereoselectivity. The present invention can employ aptamers (e.g., it is contemplated that one or more "arms" of a nanocube may comprise an apatmer), with the invention not limited to any particular aptamer, but rather allowing for any aptamer known in the art to be useful in treating a disease or condition. For example, the Aptamer Database is a comprehensive, annotated repository for information about aptamers and in vitro selection. This resource is provided to collect, organize and distribute all the known information regarding aptamer selection, and is publicly available.

The agent may be RNA-DNA hybrids with split functionalities, as described infra.

The agent may also be a targeting agent that directs the nanoparticle to a delivery site. For example, the targeting agent may be a ligand, e.g. a peptide ligand that has specific cell surface binding partners, e.g., ligand receptors, that are preferentially exhibited on the surface of a target cell. As used herein, "receptor" and "ligand" refer to two members of a specific binding pair that are binding partners. A receptor is that member of the pair that is found localized on the surface of the target; the ligand is the member of the pair that is found on the surface of the nanoparticle. Accordingly, the in certain embodiments, the invention features a nanoparticle comprising a member of a binding pair, or a fragment thereof that retains the capacity to specifically bind the other member of the binding pair, on its surface and the other member of that binding pair, or a fragment thereof that retains the capacity to specifically bind its partner, is present on the surface of a target. In certain embodiments, the targeting agent may be an antibody, for example a single-chain antibody, for which a binding partner would include an antigen thereof, or a fragment, derivative or variant thereof that retains the capacity to bind to the single-chain antibody.

A therapeutic agent may be a molecule, atom, ion, receptor and/or other entity which is capable of detecting, identifying, inhibiting, treating, catalyzing, controlling, killing, enhancing or modifying a target such as a protein, glyco protein, lipoprotein, lipid, a targeted cell, a targeted organ, or a targeted tissue.

In certain cases, the therapeutic agent is a radiotherapeutic agent, and can be selected from, but is not limited to radioactive gadolinium, radioactive boron, and radioactive iodine.

In certain examples, the agent can be, but is not limited to: drugs, such as antibiotics, analgesics, hypertensives, cardiotonics, and the like, such as acetaminaphen, acyclovir, alkeran, amikacin, ampicillin, aspirin, bisantrene, bleomycin, neocardiostatin, carboplatin, chloroambucil, chloramphenicol, cytarabine, daunomycin, doxorubicin, fluorouracil, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, temozolamide, trimethoprim, cisplatin, oxaliplatin, mechlorethamine, cyclophosphamide, chlorambucil, azathioprine, mercaptopurine, vinca alkaloids, taxanes, vincristine, vinblastine vinorelbine, vindesine, etoposide, teniposide, paclitaxel, irinotecan, topotecan, amsacrine, etoposide, etoposide phosphate, teniposide, and dactinomycinand valban; diphtheria toxin, gelonin, exotoxin A, abrin, modeccin, ricin, radioactive gadolinium, radioactive boron, and radioactive iodine; or toxic fragments thereof; metal ions, such as the alkali and alkaline-earth metals;

radionuclides, such as those generated from actinides or lanthanides or other similar transition elements or from other elements, such as 51Cr, 47 Sc, 67 Cu, 67 Ga, 82 Rb, 89 Sr, 88 Y, 90 Y, 99m Tc, 105 Rh, 109 Pd, 111 In, 115m In, 125 I, 131 I, 140 Ba, 140 La, 149 Pm, 153 Sm, 159 Gd, 166 Ho, 175 Yb, 177 Lu, 186 Re, 188 Re, 194 Ir, and 199 Au; signal generators, which includes anything that results in a detectable and measurable perturbation of the system due to its presence, such as fluorescing entities, phosphorescence entities and radiation; signal reflectors, such as paramagnetic entities, for example, Fe, Gd, Cr, or Mn; chelated metal, such as any of the metals given above, whether or not they are radioactive, when associated with a chelant; signal absorbers, such as contrast agents and electron beam opacifiers, for example, Fe, Gd, Cr, or Mn; antibodies, including monoclonal antibodies and anti-idiotype antibodies; antibody fragments; hormones; biological response modifiers such as interleukins, interferons, viruses and viral fragments; diagnostic opacifiers; and fluorescent moieties. Other pharmaceutical materials include scavenging agents such as chelants, antigens, antibodies or any moieties capable of selectively scavenging therapeutic or diagnostic agents.

Other examples of therapeutic agents include antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathominetics, anticonvuls ants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic moieties include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Nanoparticles may be directed to target sites. Preferred target sites comprise cancer cells, solid tumors, sites of inflammation and damaged bone or tissue.

For example, nanoparticle may further comprise an antibody or a peptide that acts as a targeting moiety to enable specific binding to a target cell bearing a target molecule, e.g., a cell surface marker to which the antibody or peptide is directed or a disease-specific marker to which the antibody or peptide is directed. The nanoparticle may further comprise a nucleotide, e.g. an oligonucleotide, that acts as a targeting moiety to enable specic binding to a target cell bearing a target molecule. For example, the oligonucleotide may be an aptamer that binds a specific target molecule.

Further exemplary potential applications of the multifunctional nanoparticles of the invention include use of the nanoparticles as riboswitch aptamers, ribozymes, or beacons.

Riboswitches are a type of control element that use untranslated sequence in an mRNA to form a binding pocket for a metabolite that regulates expression of that gene. Riboswitches are dual function molecules that undergo conformational changes and that communicate metabolite binding typically as either increased transcription termination or reduced translation efficiency via an expression platform.

Ribozymes catalyze fundamental biological processes, such as RNA cleavage by transesterification. The polyvalent RNA nanoparticles of the invention can be incorporated in to ribozymes using methods described in, for example, U.S. Pat. No. 6,916,653, incorporated by reference in its entirety herein.

A number of "molecular beacons" (often fluorescence compounds) can be attached to RNA nanoparticles of the invention to provide a means for signaling the presence of, and quantifying, a target analyte. Molecular beacons, for example, employ fluorescence resonance energy transfer-based methods to provide fluorescence signals in the presence of a particular analyte/biomarker of interest. In preferred embodiments, the term "molecular beacon" refers to a molecule or group of molecules (i.e., a nucleic acid molecule hybridized to an energy transfer complex or chromophore(s)) that can become detectable and can be attached to a nanoparticle under preselected conditions. Similarly, amplifying fluorescent polymers (AFPs) can be utilized in the present invention. An AFP is a polymer containing several chromophores that are linked together. As opposed to isolated chromophores that require 1:1 interaction with an analyte in conventional fluorescence detection, the fluorescence of many chromophores in an AFP can be influenced by a single molecule. For example, a single binding event to an AFP can quench the fluorescence of many polymer repeat units, resulting in an amplification of the quenching. Quenching is a process which decreases the intensity of the fluorescence emission. Molecular beacons and AFPs, including their methods for preparation, that can be used in the present invention are described in numerous patents and publications, including U.S. Pat. No. 6,261,783.

Any protein can be coupled to nanoparticles. For instance, glycoproteins are most easily coupled, as they can be oxidized to generate an active aldehyde group. Other proteins can be coupled via their —COOH group(s) but with lower efficiency. However, other means known in the art, such as di-imide reagents, e.g. carbodiimide can be used to couple proteins lacking sugars to the nanoparticles.

Polyethylene Glyocol (PEG) chains can be conjugated to the nanoparticles. PEG chains render the nanotubes highly water-soluble. PEG-phospholipids (PEG-PL) have been used in the formation of micelles and liposomes for drug delivery (Adlakha-Hutcheon, G.; Bally, M. B.; Shew, C. R.; Madden, T. D. Nature Biotech. 1999, 17, 775-779; Meyer, O.; Kirpotin, D.; Hong, K.; Sternberg, B.; Park, J. W.; Woodle, M. C.; Papahadjopoulos, D. J. Biol. Chem. 1998, 273, 15621-15627; Papahadjopoulos, D.; Allen, T. M.; Gabizon, A.; Mayhew, E.; Matthay, K.; Huang, S. K.; Lee, K. D.; Woodle, M. C.; Lasic, D. D.; Redemann, C.; Martin, F. J. Proc. Nat. Acad. Sci. USA. 1991, 88, 11460-11464).

Functional groups can be coupled to the nanoparticle, for instance the functional group can be a reactive functional group. Suitable functional groups include, but are not limited to, a haloacetyl group, an amine, a thiol, a phosphate, a carboxylate, a hydrazine, a hydrazide an aldehyde or a combination thereof. Other functional groups include groups such as a reactive functionality or a complementary group. In addition, RNA functional groups can be attached, as for example ribozymes or riboswitch aptamers. The nanoparticle can be used for attachment of small molecules for specific interactions with nucleic acids, carbohydrates, lipids, proteins, antibodies, or other ligands.

The nanoparticle can have dyes attached. The dye is can be a fluorescent dye, or a plurality of fluorescent dyes. Suitable dyes include, but are not limited to, YOYO-1, JOJO-1, LOLO-1, YOYO-3, TOTO, BOBO-3, SYBR, SYTO, SYTOX, PicoGreen, OliGreen, and combinations thereof. Other dyes include, thiazole orange, oxazole yellow, or non-intercalating dyes such as fluorescein, rhodamine, cyanine or coumarin based dyes, and combinations thereof. Other suitable dyes include, but are not limited to, 4-acetamido-4'-isothiocyanatostilobene-2,2'disulfonic acid; acridine and derivatives: acridine, acridine isothiocyanate; 5-(2'-aminoethyl)aminonap-hthalene-1-sulfonic acid (EDANS); 4-amino-N-[3-vinylsulfonyl)phenyl]naphth-alimide-3,5disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,-2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron.TM. Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalocyanine; and naphthalo cyanine. Suitable dyes for use in the nanoparticles of the present invention include, without limitation, a family of homodimeric cyanine DNA intercalating dyes from Molecular Probes that cover the visible spectrum, such as YOYO-1 (488/509), JOJO-1 (532/545), LOLO-1 (565/579), and YOYO-3 (612/631), SYBR-101 (488/505) and SYTO-62 (652/676). Given sufficient detection SN, dyes are mixed in various ratios in a single particle such that, for example, different fluorescence spectra are obtained from mixtures of just 2 dyes. According to the invention, one or more therapeutic, diagnostic, or delivery agents are directly included in the building block sequences. In certain embodiments, the delivery agent can be a targeting agent. Targeting agents are used to direct the nanoparticle to a tissue or cell target. An exemplary embodiment of a targeting agent is an antibody. For example, antibodies suitable for use as targeting agents in the present invention include antibodies directed to cell surface antigens which cause the antibody-nanoparticle complex to be internalized, either directly or indirectly. For example, in the treatment of cancer, suitable antibodies include antibodies to CD33 and CD22. CD33 and CD22 that are over-expressed and dimerized on lymphomas.

In certain preferred embodiments of the invention biotin is conjugated to the nanoparticle. For example, the nanoparticles of the invention can be further functionalized using biotin-streptavidin interactions to immobilize molecules inside or outside the polyhedra, e.g. polyhedral cages. For example, streptavidin can be conjugated to guanosine monophosphothioate (GMPS)-modified tectoRNAs by means of a biotin linker. In certain preferred embodiments, the biotin linker is incorporated to a mono-phosphothioate at the 5' position of tectoRNAs.

A wide variety of particle sizes are suitable for the present invention. In certain aspects, the particle has a diameter of about 10 nanometers to about 10 microns. Preferably the particle diameter is about 10 to 700 nanometers, and more preferably, the diameter of about 10 nanometers to about 100 nanometers.

A polyvalent RNA nanocube, RNA-DNA nanocube or RNA-DNA nanocube as described herein has a number of uses. For example, the polyvalent RNA nanocube, RNA-DNA nanocube or RNA-DNA nanocube can be used in drug delivery, imaging, nanocircuits, cell growth surfaces, medical implants, medical testing, or gene therapy.

In one particular embodiment, the RNA nanocube, RNA-DNA nanocube or RNA-DNA nanocube as described can be used in biological meshes. In one exemplary embodiment, the invention as described herein may find use as a biosensor in, for example, pathogen detection. In one particular embodiment, self-assembling nano-meshes are used to attach biosensors for pathogen detection or for x-ray crystallography by placing multiple copies of a protein or functional RNAs, for example, on the mesh. Biosensors for pathogen detection are advantageously employed in bioterrorism capacities.

In another exemplary embodiment, the polyvalent RNA nanocube, RNA-DNA nanocube or RNA-DNA nanocube of the invention, as described herein, are employed as skeletons or scaffolds for tissue growth.

These uses are exemplary, and not considered to be limiting.

RNA-DNA and DNA-RNA Hybrid Nanocubes

Control over the coincident delivery of different functionalities and their synchronized intracellular activation can significantly contribute to the biomedical applications of RNA and DNA nanoparticles. Described herein are several different, yet intrinsically related methodologies based on activation of RNA interference (RNAi) in human cells. It is newly described herein how RNA and DNA nanoscaffolds can be functionalized with multiple short interfering RNAs (siRNAs) (e.g. siRNAs targeting six different parts of HIV-1) as well as RNA-DNA hybrids. The RNA-DNA hybrids cannot be diced and thus are not active. Cognate hybrids re-associated through ssDNA toeholds interactions and released either the functional RNA nanoparticles or siRNAs. Several cell culture experiments demonstrated FRET and RNAi activation by conditional triggering of split functionalities in cells. Importantly, interferon activation assays revealed the significantly lower levels of interferons produced in response to transfections with DNA nanocubes, as compared to the RNA counterparts, indicating that these DNA nanocube molecules (particularly DNA-RNA hybrid nanocubes as detailed herein) likely possess greater potential for therapeutic use.

RNA nanotechnology offers an advantage of precise control over the composition and stoichiometry of the delivered cargo[5, 7-10]. RNA molecules can be programmed[11, 12] to form a wide variety of compact and stable artificial three-dimensional nanostructures (called RNA nanoparticles) suitable for the broad range of clinical and nanotechnological applications[5, 8, 10, 13-18]. A strategy based on RNA-DNA hybrids was recently developed that could be generally used for triggering activation of different functionalities in vitro and in vivo[19, 20]. The key idea was to split the functional entity (e.g. Dicer Substrate RNAs, referred to herein as DS RNAs or DsiRNAs, RNA aptamers, FRET pair of dyes) into two RNA-DNA hybrids. The resulting inactive hybrids were decorated with complementary ssDNA toeholds which would interact and trigger the re-association process when both of the cognate hybrids were present in close proximity. The re-association released the split functionalities and restored their original function. Utilizing this novel approach involving RNA-DNA hybrids[19, 20] in combination with RNA nanotechnology[21, 22] expertise, RNA-DNA and DNA-RNA hybrid nanocubes were developed as described herein consisting of either RNA or DNA cores (composed of six strands) respectively with six attached RNA-DNA hybrid duplexes. After addition of six cognate hybrids to the hybrid nanoparticles, the complementary toeholds in each duplex initiated re-association of the DNA strands, displacing the RNA strands. This induced the re-association of the RNA duplexes, which were further processed by the human Dicer enzyme, thereby activating RNAi.

Figure 12A:
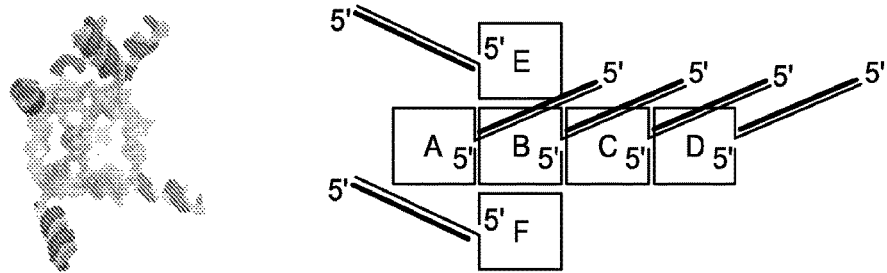
FIGS. 12A to 12C show 3D models and corresponding 2D diagrams of RNA and DNA cubes functionalized through the 3'-side extensions of scaffold strands with six Dicer substrate siRNAs (DsiRNAs) or RNA-DNA hybrids for conditional split function (RNAi) activation. RNA strands are colored in grey and red; DNA strands are in blue. Assemblies of RNA nanocubes (12A and 12B) and a DNA nanocube (12C), respectively, are shown. The RNA nanocube of FIG. 12A is functionalized with six different dsRNA arms, while the RNA nanocube of FIG. 12B is functionalized with six different RNA-DNA hybrid arms. The DNA nanocube of FIG. 12C is functionalized with six different RNA-DNA hybrid arms. The nanocubes of FIGS. 12B and 12C are inactive for RNAi in the absence of interaction with free DNA-RNA hybrids that result in strand separation of arms and annealing to antisense DNA and RNA strands, respectively, for DNA and RNA sequences associated with the nanocube structure.
Figure 12B:
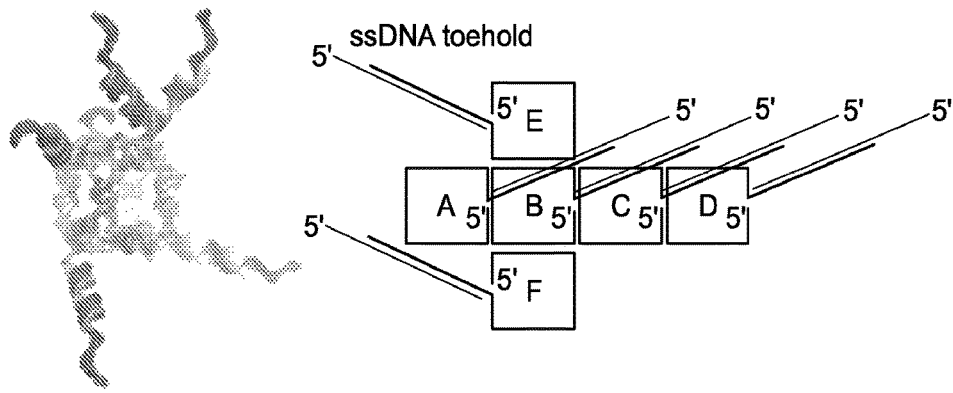
Figure 12C:
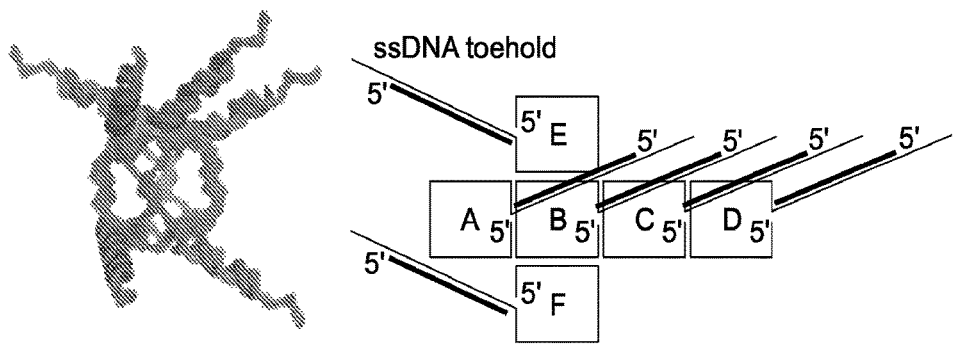

Overall, three different types of RNA, RNA-DNA and DNA-RNA functional nanoparticles (schematically shown in FIG. 12) were designed and tested herein. All three-dimensional models of the functional nanoparticles presented herein were generated as detailed in below Example 1. Experimental results are presented and discussed in Examples 2-6 below.

Compositions

The invention, in part, pertains to a drug delivery composition comprising the NP (nanocube) as described herein. The drug delivery composition of the invention can gain entry into a cell or tissue.

Advantageously, the drug delivery composition of the invention provides for a more controlled delivery of an active agent, especially a therapeutic agent, to a site of action at an optimum rate and therapeutic dose. Thus, improvements in therapeutic index may be obtained by modulating the distribution of the active ingredient in the body. Association of the active ingredient with a delivery system enables, in particular, its specific delivery to the site of action or its controlled release after targeting the action site. By reducing the amount of active ingredient in the compartments in which its presence is not desired, it is possible to increase the efficacy of the active ingredient, to reduce its toxic side effects and even modify or restore its activity.

It is understood by one of skill in the art that changing the base composition of RNA changes the half-life of RNA and thus the release of RNA from the composition. For instance, the composition can be modified to consist of fast release, slow release or a staged release of polyvalent RNA nanoparticle.

In certain preferred embodiments, the drug delivery composition can comprise a second therapeutic agent. In some embodiments, the composition comprising nanoparticles and the second therapeutic agent are administered simultaneously, either in the same composition or in separate compositions. In some embodiments, the nanoparticle composition and the second therapeutic agent are administered sequentially, i.e., the nanoparticle composition is administered either prior to or after the administration of the second therapeutic agent. The term "sequential administration" as used herein means that the drug in the nanoparticle composition and the second agent are administered with a time separation of more than about 15 minutes, such as more than about any of 20, 30, 40, 50, 60 or more minutes. Either the nanoparticle composition or the chemotherapeutic agent may be administered first. The nanoparticle composition and the chemotherapeutic agent are contained in separate compositions, which may be contained in the same or different packages. In some embodiments, the administration of the nanoparticle composition and the second therapeutic agent are concurrent, i.e., the administration period of the nanoparticle composition and that of the second therapeutic agent overlap with each other. In some embodiments, the administration of the nanoparticle composition and the second therapeutic agent are non-concurrent. For example, in some embodiments, the administration of the nanoparticle composition is terminated before the second therapeutic agent is administered. In some embodiments, the administration of the second therapeutic agent is terminated before the nanoparticle composition is administered. Administration may also be controlled by designing the RNA nanoparticle or nano-tube to have different half lives. Thus, particle dissolution would be controlled by a timed release based upon variations in designed RNA stability.

The second therapeutic agent is selected from, but not limited to chemotherapeutic agents, cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodilators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

When the second therapeutic agent is a chemotherapeutic agent, the chemotherapeutic agent is selected from, but not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-nl; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlomaphazine, novembichin, phenesterine, trofosfamide, estermustine, chlorozotocin, gemzar, nimustine, ranimustine, dacarbazine, mannomustine, mitobronitol,aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. Additional cancer therapeutics include monoclonal antibodies such as rituximab, trastuzumab and cetuximab.

Reference to a chemotherapeutic agent herein applies to the chemotherapeutic agent or its derivatives and accordingly the invention contemplates and includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

The invention also relates to pharmaceutical or diagnostic compositions comprising the nanoparticles of the invention and a pharmaceutically acceptable carrier. The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in Remington's Pharmaceutical Sciences, Mack Publishing Company, a standard reference text in this field.

Methods of Treatment

The methods of the invention encompass method of treating or preventing diseases or disorders by administering to subjects in need thereof an effective amount of a polyvalent RNA nanoparticle comprising one or more functionalities as described herein. Accordingly, a number of diseases or disorders are suitable for treatment according to the methods of the invention. Examples include, but are not limited to, Adenoma, Ageing, AIDS/HIV, Alopecia, Alzheimer's disease, Anemia, Arthritis, Asthma, Atherosclerosis, Cancer, Cardiac conditions or disease, Diabetes mellitus, Foodborne illness, Hemophilia A-E, Herpes, Huntington's disease, Hypertension, Headache, Influenza, Multiple Sclerosis, Myasthenia gravis, Neoplasm, Obesity, Osteoarthritis, Pancreatitis, Parkinson's disease, Pelvic inflammatory disease, Peritonitis, Periodontal disease, Rheumatoid arthritis, Sepsis, Sickle-cell disease, Teratoma, Ulcerative colitis, and Uveitis.

The methods of the invention further encompass diagnostics.

The methods may be practiced in an adjuvant setting. "Adjuvant setting" refers to a clinical setting in which, for example, an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk"

or "low risk") depends upon several factors, most usually the extent of disease when first treated. The methods provided herein may also be practiced in a neoadjuvant setting, i.e., the method may be carried out before the primary/definitive therapy. Thus, in some embodiments, the individual has previously been treated. In other embodiments, the individual has not previously been treated. In some embodiments, the treatment is a first line therapy.

Dosage

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Methods of Delivery

The nanoparticle compositions described herein can be administered to an individual (such as human) via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the nanoparticle composition can be administered by inhalation to treat conditions of the respiratory tract. The composition can be used to treat respiratory conditions such as pulmonary fibrosis, bronchceolitis obliterans, lung cancer, bronchoalveolar carcinoma, and the like. In some embodiments, the nanoparticle composition is administrated intravenously. In some embodiments, the nanoparticle composition is administered orally.

The dosing frequency of the administration of the nanoparticle composition depends on the nature of the therapy and the particular disease being treated. For example, dosing frequency may include, but is not limited to, once daily, twice daily, weekly without break; weekly, three out of four weeks; once every three weeks; once every two weeks; weekly, two out of three weeks.

The administration of nanoparticles may be carried out at a single dose or at a dose repeated once or several times after a certain time interval. The appropriate dosage varies according to various parameters, for example the individual treated or the mode of administration.

The dosing frequency of the nanoparticle composition or the nanoparticle composition and the second therapeutic agent may be adjusted over the course of the treatment, based on the judgment of the administering physician.

When administered separately, the nanoparticle composition and the second therapeutic agent can be administered at different dosing frequency or intervals. For example, the nanoparticle composition can be administered weekly, while a second agent can be administered more or less frequently. In some embodiments, sustained continuous release formulation of the nanoparticle and/or second agent may be used. Various formulations and devices for achieving sustained release are known in the art. The doses required for the nanoparticle composition and/or the second agent may (but not necessarily) be lower than what is normally required when each agent is administered alone. Thus, in some embodiments, a subtherapeutic amount of the drug in the nanoparticle composition and/or the second agent are administered. "Subtherapeutic amount" or "subtherapeutic level" refer to an amount that is less than the therapeutic amount, that is, less than the amount normally used when the drug in the nanoparticle composition and/or the second agent are administered alone. The reduction may be reflected in terms of the amount administered at a given administration and/or the amount administered over a given period of time (reduced frequency).

A combination of the administration configurations described herein can be used. The combination therapy methods described herein may be performed alone or in conjunction with another therapy, such as surgery, radiation, chemotherapy, immunotherapy, gene therapy, and the like. Additionally, a person having a greater risk of developing the disease to be treated may receive treatments to inhibit and/or delay the development of the disease. The dose of nanoparticle composition will vary with the nature of the therapy and the particular disease being treated. The dose should be sufficient to effect a desirable response, such as a therapeutic or prophylactic response against a particular disease. Appropriate doses will be established by persons skilled in the art of pharmaceutical dosing such as physicians.

In certain embodiments, the siRNAs can be administered as bolaamphiphiles. Bolaamphiphiles have relatively low toxicities, long persistence in the blood stream, and most importantly, in aqueous conditions can form poly-cationic micelles thus, becoming amenable to association with siRNAs. Depending on the application, the extent of siRNA chemical protection, delivery efficiency, and further intracellular release can be varied by simply changing the type of bolaamphiphile used (see, e.g. Kim et al. Mol Ther Nucleic Acids. 2: e80, 2013, incorporated by reference in its entirety herein).

Kits

The disclosure provides kits for the treatment or prevention of disease. In one embodiment, the kit includes a therapeutic or prophylactic composition containing an effective amount of an agent of the invention (e.g., NPs) in unit dosage form. In some embodiments, the kit comprises a sterile container which contains a therapeutic or prophylactic compound; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the disclosure is provided together with instructions for administering it to a subject having or at risk of developing a disease. The instructions will generally include information about the use of the composition for the treatment or prevention of the disease (e.g., neoplasia or viral infection). In other embodiments, the instructions include at least one of the following: description of the compound; dosage schedule and administration for treatment or prevention of the disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.
Recombinant Polypeptide Expression The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The promise of RNA interference based therapeutics is made evident by the recent surge of biotechnological drug companies that pursue such therapies and their progression into human clinical trials. Recent achievements in RNA nanotechnology introduced nanoscaffolds (nanorings) with the potential for a broad use in biomedical applications (PCT/US10/38818, incorporated by reference in its entirety herein). As presented herein, besides functionalization with multiple short interfering RNAs for combinatorial RNA interference, these nanoscaffolds also allow simultaneous embedment of assorted RNA aptamers, fluorescent dyes, proteins, as well as recently developed auto-recognizing RNA-DNA hybrids used to conditionally activate multiple split functionalities. These new constructs were extensively characterized and visualized in vitro and in cell culture by various experimental techniques. The results revealed silencing efficiencies of targeted genes comparable to those observed for conventional siRNAs, yet with the attributes imparted by the nanocube configuration (serum stability, stoichiometric delivery of RNAi payloads, etc.), with the functionality of DNA cube structures and RNA cube-hybrid arm structures being particularly noteworthy for allowing activation of RNAi payloads to be triggered via administration of cognate hybrid DNA-RNA molecules. DNA cube structures were also identified as especially serum stable and non-immunogenic (as assessed by IFN activation assays). Due to the combinatorial nature and relative engineering simplicity of such nanocubes, they can be used in various nanotechnological applications.

Example 1

Methods 3D modeling of functional RNA and DNA cube assemblies. All three-dimensional models of the functional nanoparticles presented herein were generated using custom-written PyMOL scripts. In case of the RNA cube scaffolds, the previously generated and tested RNA cube model[22] was mated with separately generated multiple alternative models of a helix and siRNA arm junction generated with the aid of RNA2D3D, MC-Sym, and RNAComposer[38-40]. Overlapping fragments were best fit together (minimum RMSD), then any structural duplicates were removed, and the final models were converted into PDB files and imaged in PyMOL. The DNA cube models were built using RNA cube helices as guides to lay out separately generated B-form DNA helices bridged in the corners with single-stranded (B-form) DNA fragments. Overlapping backbones were best fit and ultimately fused into individual chains (with duplicate fragments removed). The junction models were best-mated to the cubic DNA scaffold and separately generated A-form RNA-DNA (hybrid), and B-form DNA-DNA helical arms were best-fit, depending on the modeled cube.

Functional RNA and DNA cube assemblies and native PAGE. The designing principles and production of RNA strands entering the composition of nanocubes functionalized with six siRNAs has been comprehensively described elsewhere[13]. The full list of RNA and DNA sequences used is presented in FIGS. 6-11. RNA molecules were purchased from Integrated DNA Technologies, Inc. or prepared by transcription of PCR amplified DNA templates; synthetic DNA molecules coding for the sequence of the designed RNA were purchased and amplified by PCR using primers containing the T7 RNA polymerase promoter. RNA molecules were prepared enzymatically by in vitro transcription using T7 RNA polymerase[41]. Transcription was performed in 50 mM Tris-HCl, pH 7.5, 2 mM spermidine, 1 mM DTT, 0.4 units/Al RNasine (Promega), 5 mM MgCl, 0.5 mM MnCl2, 1 mM NTPs, 0.1 µM of DNA template, and 0.3 units/A1 T7 RNA polymerase (Promega). RNA, RNA-DNA and DNA-RNA nanocubes were assembled as detailed in Afonin et al.[13, 21]. Cognate RNA-DNA hybrids were assembled as described in Afonin et al[19]. For the visualization of assembled nanoparticles, native-PAGE was used[42, 43]. Typically, assembly experiments were analyzed at 10° C. on 7% (29:1) native polyacrylamide gels in the presence of 89 mM Tris-borate, pH 8.3, 2 mM Mg(OAc)$_2$. A Hitachi FMBIO II Multi-View Imager was used to visualize SYBR Gold stained RNA-, RNA-DNA- and DNA-RNA-based nanoparticles.

Dynamic Light Scattering (DLS) experiments. For DLS experiments, 400 µl of sample solutions containing assembled nanoparticles (500 nM final) were used. The samples were measured at 25° C. with a Zetasizer nano (Malvern Instruments Ltd) equipped with a 633 nm laser[44]. Readings with polydispersity index (PDI) below 0.5 were used.

Recombinant human Dicer assay. For dicing experiments, purchased DsiRNA sense strand molecules were 5'-end radiolabeled using T4 Polynucleotide Kinase. Nanocubes with either six DsiRNAs or six RNA-DNA hybrids were prepared as described above (3 µM final). For dicing experiments, samples were incubated for 3 hours at 37° C. with recombinant human turbo dicer enzyme kit (Genlantis) prior to analysis on 2 mM Mg(OAc)$_2$ native 7% PAGE (described above). The electrophoresis was performed for 1.5 hours at 15 W at 10° C. followed by the exposure to a phosphorimaging screen and analysis using phosphorimaging instrument (Storm).

Human blood serum degradation studies. Aliquots of freshly drawn human whole blood serum (blood was allowed to coagulate, then spun down and supernatant was collected) were used. Different radiolabeled constructs (3 µM final) were incubated with 5% (v/v) human blood serum at 37° C. for various time periods. Prior to immediate loading on native-PAGE, degradation time courses were quenched on dry ice and loaded to the gel in reverse order. The electrophoresis was performed as described above.

Fluorescence studies. Re-association of RNA-DNA and DNA-RNA nanocubes with cognate RNA-DNA hybrids in vitro was tracked with FRET measurements using a FluoroMax3 (Jobin-Yvon, Horiba). All fluorescently labeled sequences are shown in FIG. 11 (Fluorescently labeled molecules). For all the experiments, the excitation wavelength was set at 460 nm and the excitation and emission slit widths were set at 2 nm. Alexa 488 labeled constructs were first incubated for two minutes at 37° C. and then Alexa546 labeled constructs were added. Upon excitation at 460 nm, the emissions at 520 nm and 570 nm were recorded simultaneously every 30 seconds to follow the process of re-association through FRET measurements. This was done with naked constructs and constructs individually pre-incubated with L2K in the amounts relevant for transfection conditions (see below).

Transfection of human breast cancer cells. Human breast cancer cell line MDA-MB-231 (with or without eGFP) was grown in D-MEM media (Gibco BRL) supplemented with 10% FBS and penicillin-streptomycin in a 5% CO$_2$ incubator. All transfections were performed using Lipofectamine 2000 (L2K) purchased from Invitrogen. 10× or 50× solutions of nanoparticles were individually pre-incubated at room temperature with L2K. To avoid re-association in media, RNA-DNA or DNA-RNA NPs (nanocubes) and cognate RNA-DNA hybrids were pre-incubated with L2K separately. In vitro fluorescent experiments showed no re-association of these complexes in solution (FIGS. 15a and 16d) thus, the re-association occurred only in cells. Prior to each transfection, the cell media was swapped with OPTI-MEM mixed with prepared 50× of NP/L2K complexes and/or Hybrid/L2K complexes to the final concentration of 1×. The cells were incubated for 4 hours, followed by the media change (D-MEM, 10% FCS, 1% pen-strep).

Endosomal co-localization studies. To confirm the endosomal location of endocytosed fluorescently labeled functional RNA NP (e.g., nanocubes) in cells, co-staining experiments with endosomal markers (EEA1 and Rab7) were performed[19]. Cells were transfected with RNA NPs labeled with six Alexa546 dyes. On the next day, transfected cells were fixed with 4% paraformaldehyde for 20 minutes at room temperature and handled at this temperature thereafter. Samples were washed three times with PBS and then permeabilized with 0.2% Triton X-100 for 20 minutes. Upon washing three times with PBS, samples were blocked for one hour with 1% BSA and then exposed to primary antibodies against the early endosome associated protein EEA1 (Cell signaling) or against the late endosome marker Rab7 (Cell signaling). Upon washing three times with PBS, the samples were stained with a secondary Alexa 488 antibody (Molecular Probes). As a comparison, fluorescently labeled DsiRNAs were used at six fold higher concentrations.

Microscopy. Re-association of RNA-DNA hybrids in cells was assessed through FRET[19]. All measurements were performed using a LSM 710 confocal microscope (Carl Zeiss) with a 63×, 1.4 NA magnification lens. All images were taken with a pinhole adjusted to 1 airy unit. Fluorescently labeled hybrid NPs and cognate hybrids were individually preincubated with L2K and co-transfected into cells. On the next day, the samples were fixed by incubation in 4% paraformaldehyde for 20 minutes at room temperature. Images of the cells were then taken to assess the appearance of FRET within the sample. For Alexa 488 imaging, the 488 nm line of an Argon laser was used as excitation and the emission was collected between 493 and 557 nm. For Alexa 546 imaging, a DPSS 561 laser was used for excitation and emission was collected between 566 and 680 nm. To evaluate the sensitized emission through FRET, images were taken exciting the sample with the 488 nm line and collecting emission between 566 and 680 nm. Because of spectral overlap, the FRET signal was contaminated by donor emission into the acceptor channel and by the excitation of acceptor molecules by the donor excitation wavelength. This bleed-through was assessed through measurements performed with samples transfected with individual dyes and was mathematically removed from the images of FRET.

Flow cytometry experiments. For analysis with flow cytometry experiments, the MDA-MB-231 (with or without eGFP) cells grown in 12-well plates (1.0×10$^5$ cells per well) were lifted with cell dissociation buffer and the level of nanoparticles uptake or expression of eGFP was determined by fluorescence-activated cell sorting (FACS) analysis on a FACScalibur flow cytometer (BD Bioscience)[44]. At least 20,000 events were collected and analyzed using the CellQuest software.

Virus production. 293T cells were transfected with HIV-RFP and VSV-G in the presence of increasing amount of siRNA mixture and functionialized RNA nanocubes. As controls of target siRNA, pcDNA was used. 48 h post-transfection culture supernatants were collected and filtered with 0.45 µm pore-size sterile filters.

Infectivity assay. The day before infection, 2.5×10$^4$ HeLa cells/well were plated in 24-well tissue culture plates. On the day of infection, the culture media (DMEM, 10% FBS) were replaced with new culture media containing Polybrene at the final concentration of 5 µgr/ml. Different dilutions of virus-containing supernatant were added to the plates before their incubation at 37° C. for 48 h. After this incubation stage, the cells were trypsinized and resuspended in PBS containing 2% FBS. The percentages of infected cells were measured by fluorescence-activated cell sorter (FACS) analysis (FAC-SCalibur, Becton Dickinson).

Interferon activation and cell viability assays. Type I IFN activity was measured using THP-1 reporter cells which express secreted alkaline phosphatase (SEAP) in response to type I IFN (Invivogen). THP-1 cells were depleted for cGAS or MAVS by siRNA to assess whether IFN induction was dependent on DNA- or RNA-sensing, respectively. THP-1 cells were cultivated in RPMI 1640 with 10% FBS, 10 mM HEPES, 1 mM pyruvate, penicillin-streptomycin, and normocin (100 µg/mL). THP-1 cells were transfected with control or SMART pool siRNAs (Thermo) at a final concentration of 50 nM with RNAiMax (Invitrogen). After 24 hours, cells were differentiated with 50 ng/ml phorbol 12-myristate 13-acetate (PMA)(Sigma) for 24 hours. Cells were transferred to a 96-well dish and incubated for an additional 24 hours in media lacking PMA prior to transfection of nanocubes. Nucleic acids were transfected using Lipofectamine 2000 reagent according to the manufacturer's protocol (Invitrogen) at a final concentration of 10 nM. Culture supernatants were harvested 24 hours post-transfection and assayed for alkaline phosphatase activity by incubating with the QUANTI-BLUE substrate (Invivogen) and measuring absorbance at 625 nm using a spectrophotometer. The viability of the THP-1 cells was assessed with the CellTiter-Blue assay (Promega, Madison, Wis.) following manufacturer's instructions. Briefly, the CellTiter-Blue reagent was added to the wells at a 1-to-6 ratio and the fluorescence was recorded (560 ex/590 em) upon 1-2 hours incubation at 37° C.

Example 2

Figure 2A:
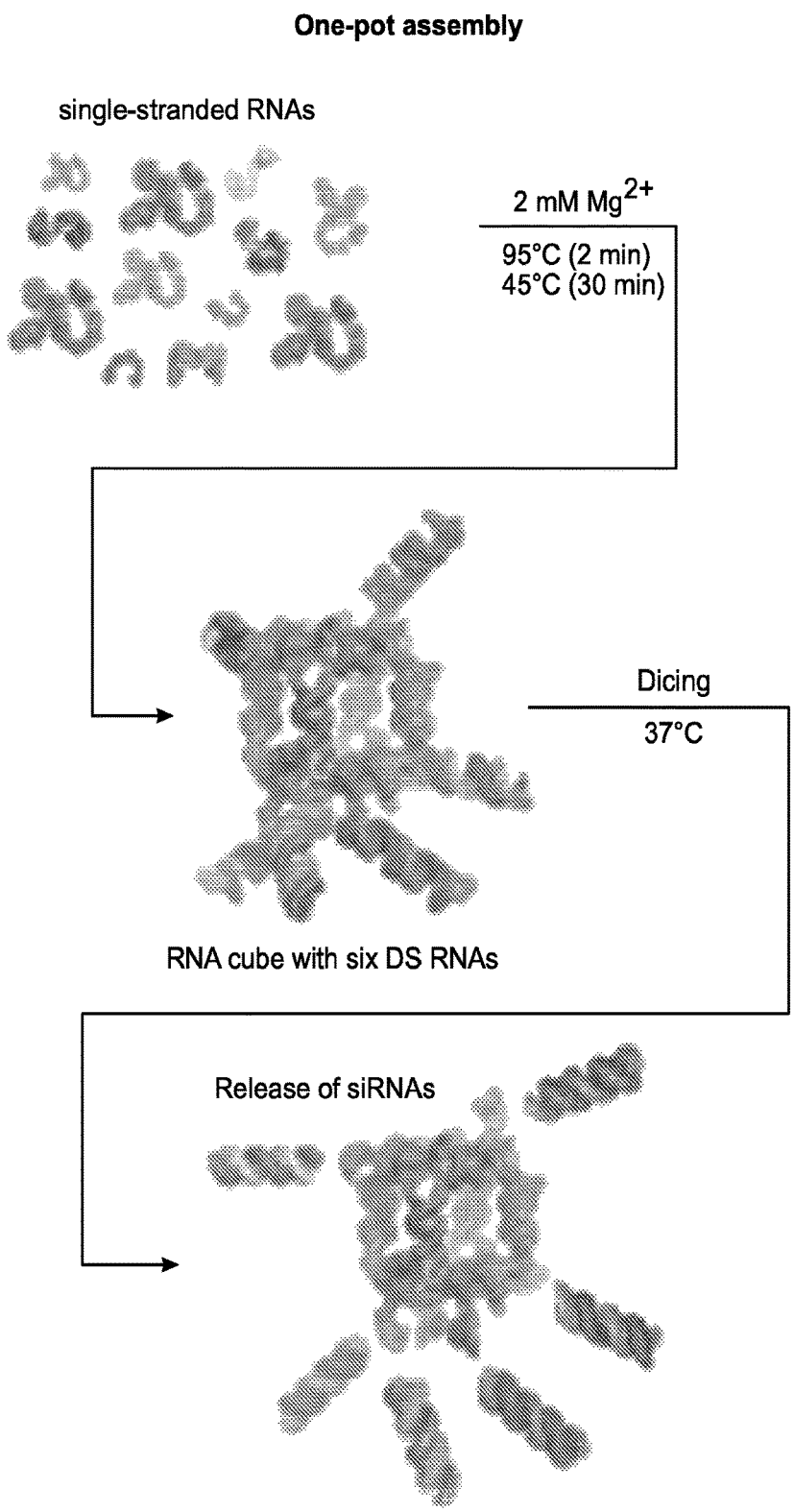
Figure 2B:
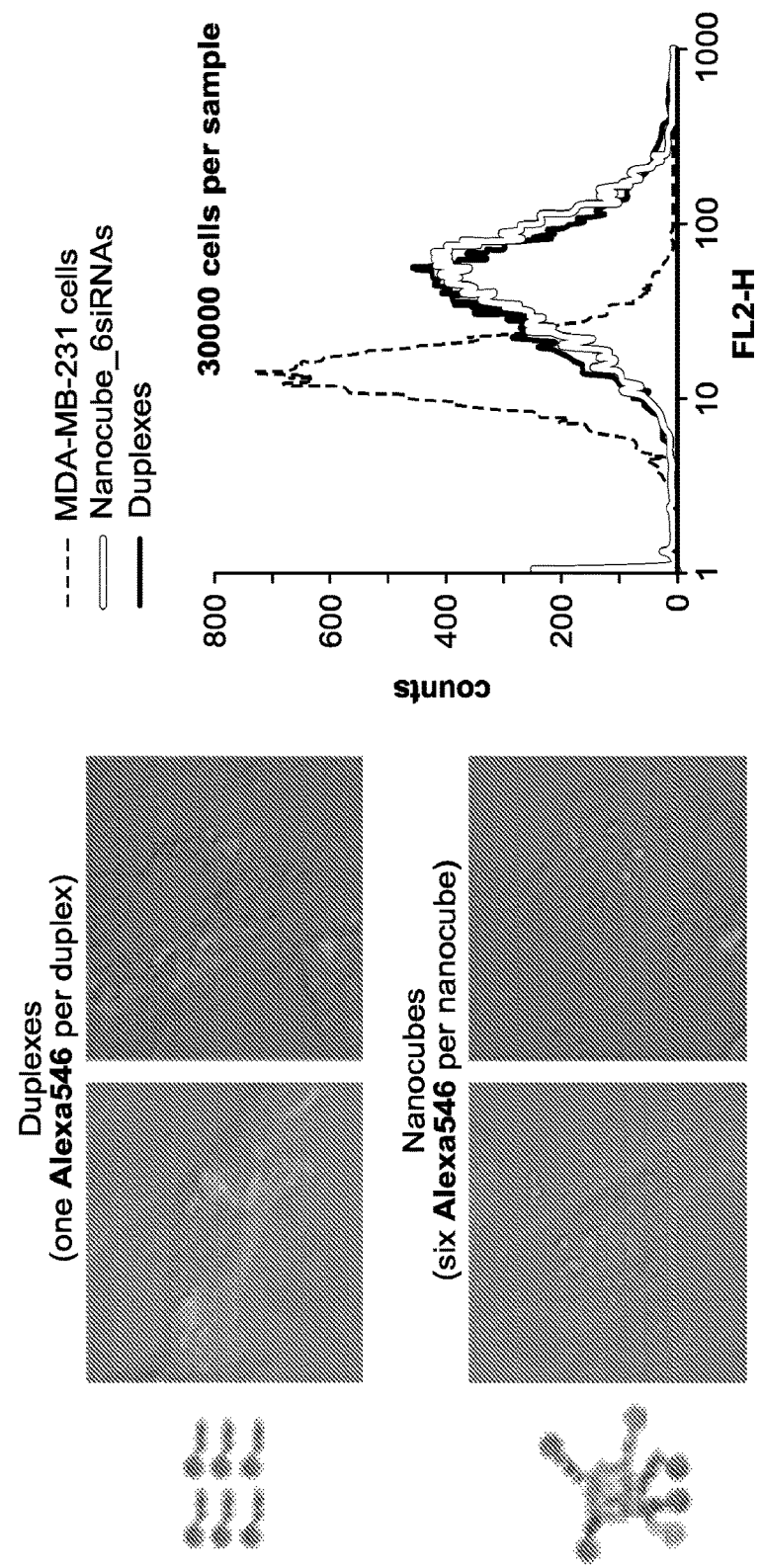
Figure 2D:
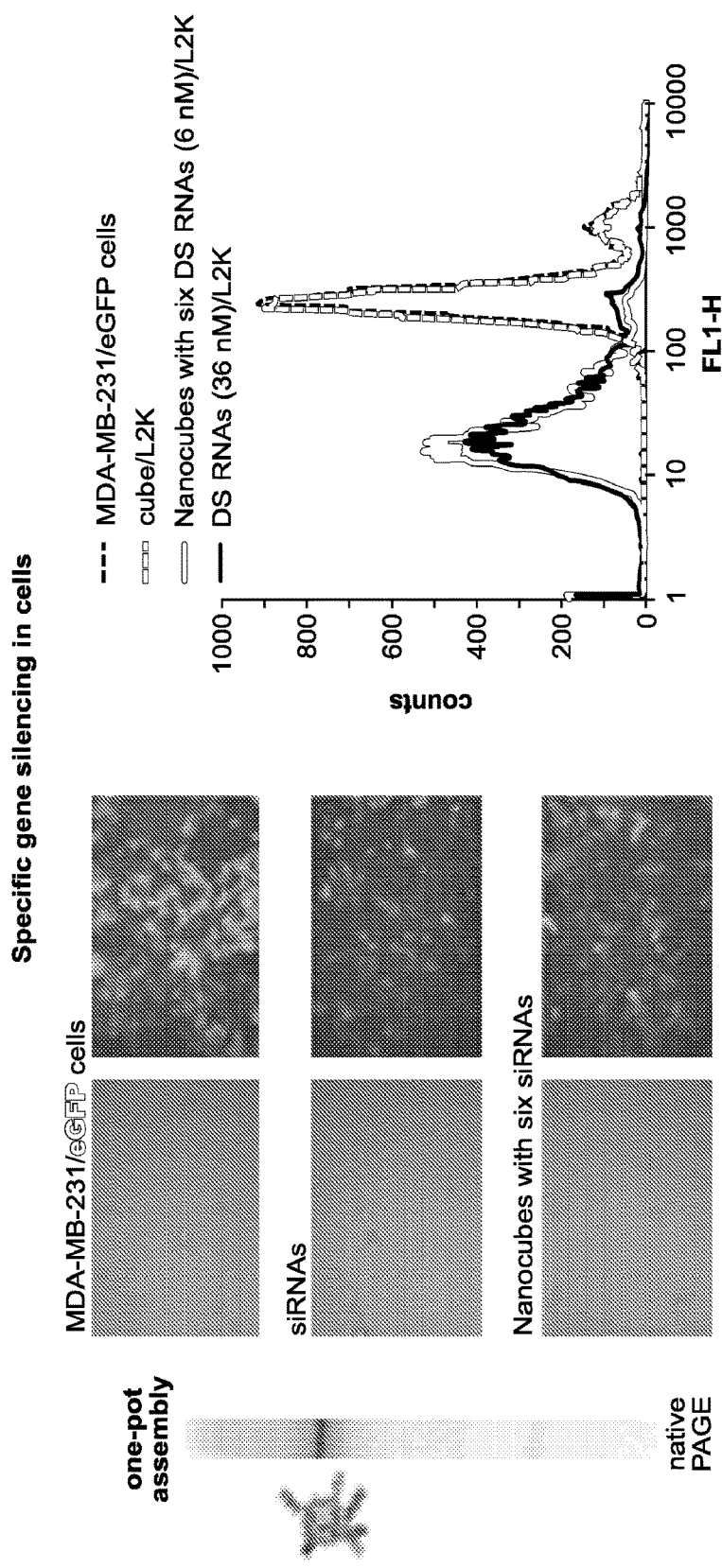
Figure 13B:
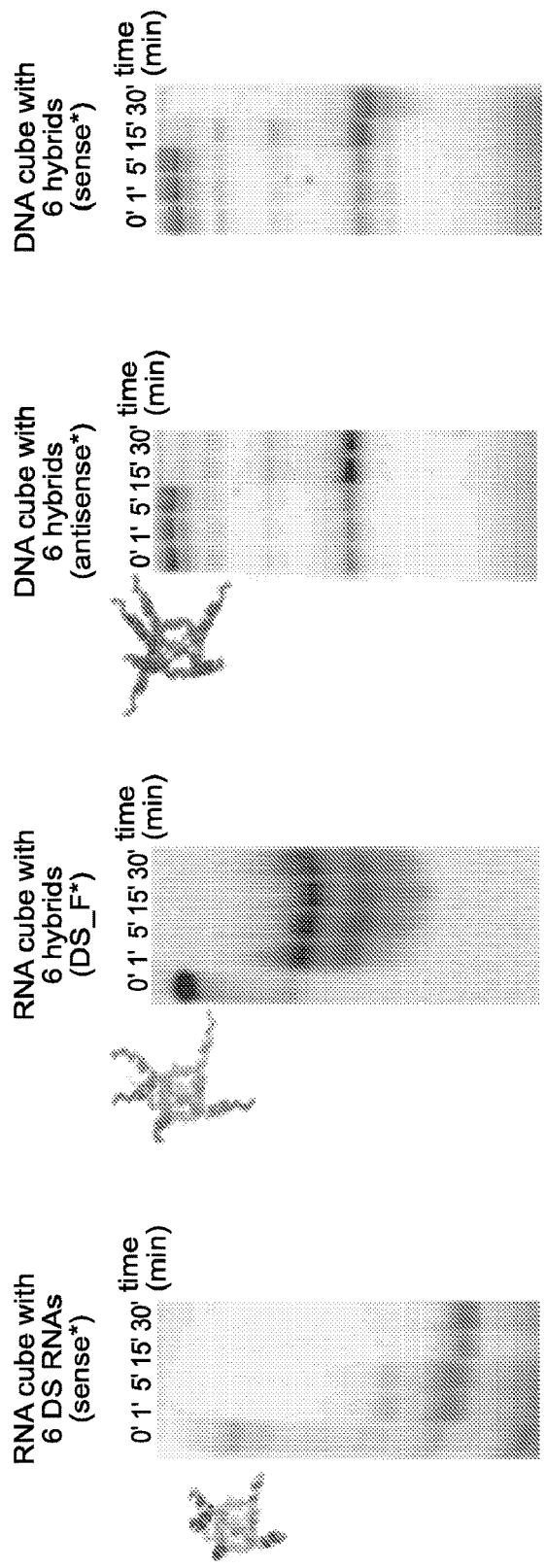
Figure 14:
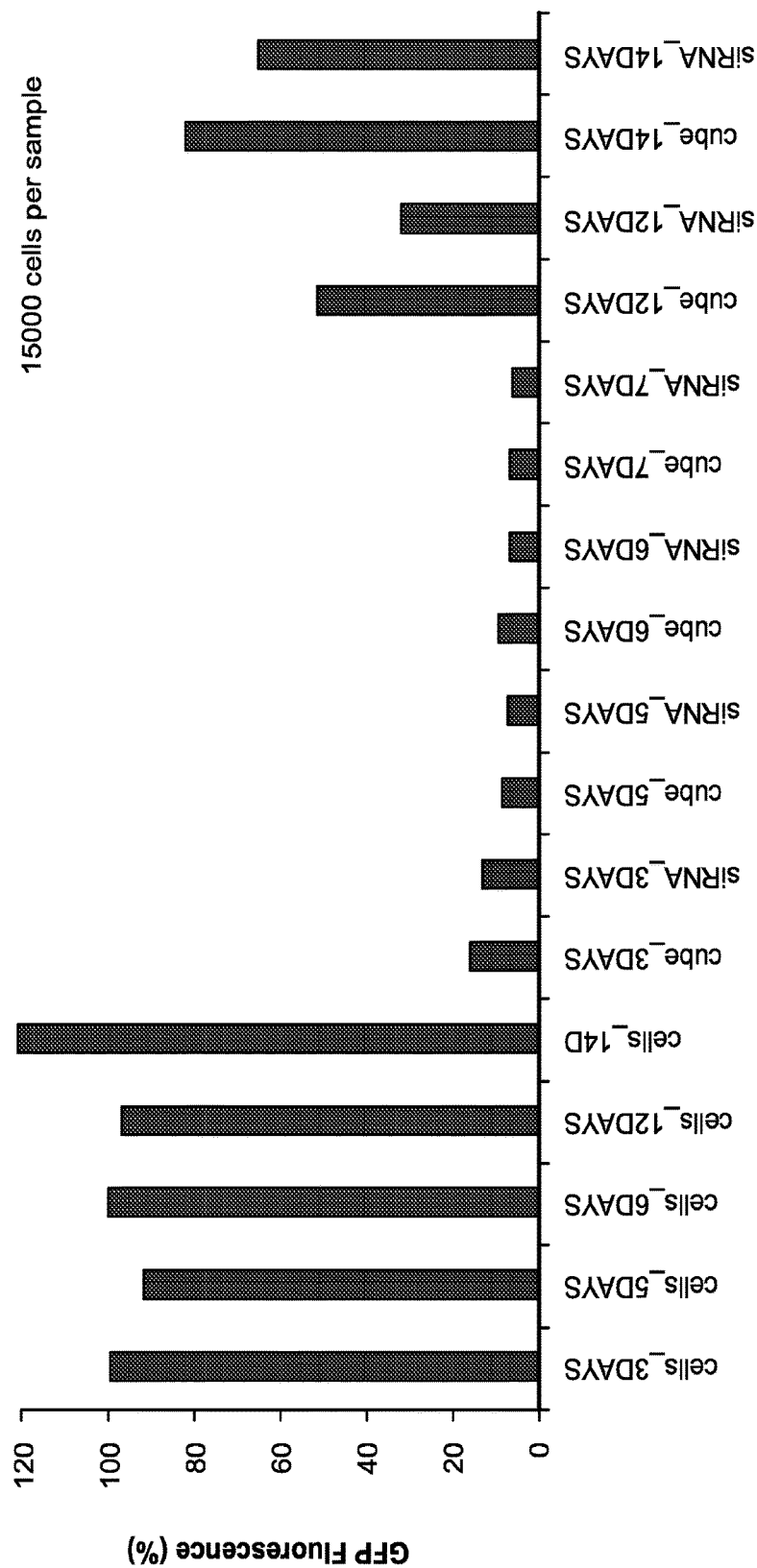
FIG. 14 shows GFP knockdown of GFP-targeting nanocubes was significant and durable in human breast cancer cells (MDA-MB-231/GFP) which stably expressed enhanced GFP (eGFP). Three, five, six, and 12 days after the transfection of cells with nanocubes, eGFP expression was statistically analyzed with flow cytometry experiments. As a control, siRNA duplexes against eGFP were used for all time points.

Construction, Assembly and Knockdown Efficacy of RNA Nanocubes Having DsiRNA Arms Six-stranded RNA nanocubes with three single-stranded uracils at the corner were previously characterized[22] as scaffolds for the controlled delivery of multiple siRNAs. Through 3'-side extensions of individual scaffold strands, RNA nanocubes were functionalized with six Dicer Substrate RNAs[23] or DsiRNAs (FIG. 3a). DsiRNAs were used to promote the release of siRNAs in cells through dicing[13] (FIG. 13a). To study the potential use of RNA scaffolds for simultaneous delivery of multiple siRNAs, nanocubes functionalized with six fluorescently labeled DsiRNAs were transfected using Lipofectamine 2000 into human breast cancer cells (FIGS. 2b and 12), visualized by confocal fluorescence microscopy and analyzed by fluorescence-activated cell sorting (FACS). The results revealed significant intracellular uptake of functionalized nanocubes through endocytosis (FIG. 2c). Intracellular release of siRNAs activating RNAi was assessed in experiments with human breast cancer cells that stably expressed enhanced green fluorescent protein (FIG. 2d). MDA-MB-231/eGFP cells were transfected with nanocubes carrying six DsiRNAs targeting eGFP[23] and the same individual siRNAs at six-fold higher concentrations. After three days, the levels of eGFP expression were analyzed with fluorescence microscopy and FACS. Extensive eGFP silencing was observed, with considerable duration (GFP knockdown remained significant even on the twelfth day post-transfection; FIG. 14). Thus, RNA nanocubes having DsiRNA arms were successfully constructed and possessed robust knockdown efficacy.

Example 3

RNA Nanocubes Having DsiRNA Arms Targeting Multiple Sites in HIV-1 Were Highly Effective At Reducing Infectivity In Vitro To demonstrate the generality and the feasibility of the approach of using functionalized nanocubes as therapeutic moieties, several different HIV-1 genes (ldr, nef, pro, env, gag and rt) were targeted with six different DsiRNAs[24] carried by the RNA nanocubes (FIG. 3). 293T cells were used to produce HIV-1 pseudotyped with VSV-G in the presence of increasing amounts of nanocubes or a mixture of the six DsiRNAs. Equal amounts of virus-containing supernatant were used to infect HeLa cells, and the percentage of infected cells was detected using FACS analysis. As shown in FIG. 3, nanocubes had a negative effect on HIV-1 production that was comparable to a mixture of six DsiRNAs alone. This approach can be used as a part of a combinatorial RNAi (co-RNAi) strategy used for highly effective simultaneous suppression of multiple viral genes, thereby preventing the possibility of mutation-assisted escape from RNAi[25, 26]. Thus, functional nanocubes were successfully constructed that knocked down multiple targeted HIV-1 genes, thereby reducing HIV-1 production.

Example 4

Figure 4A:
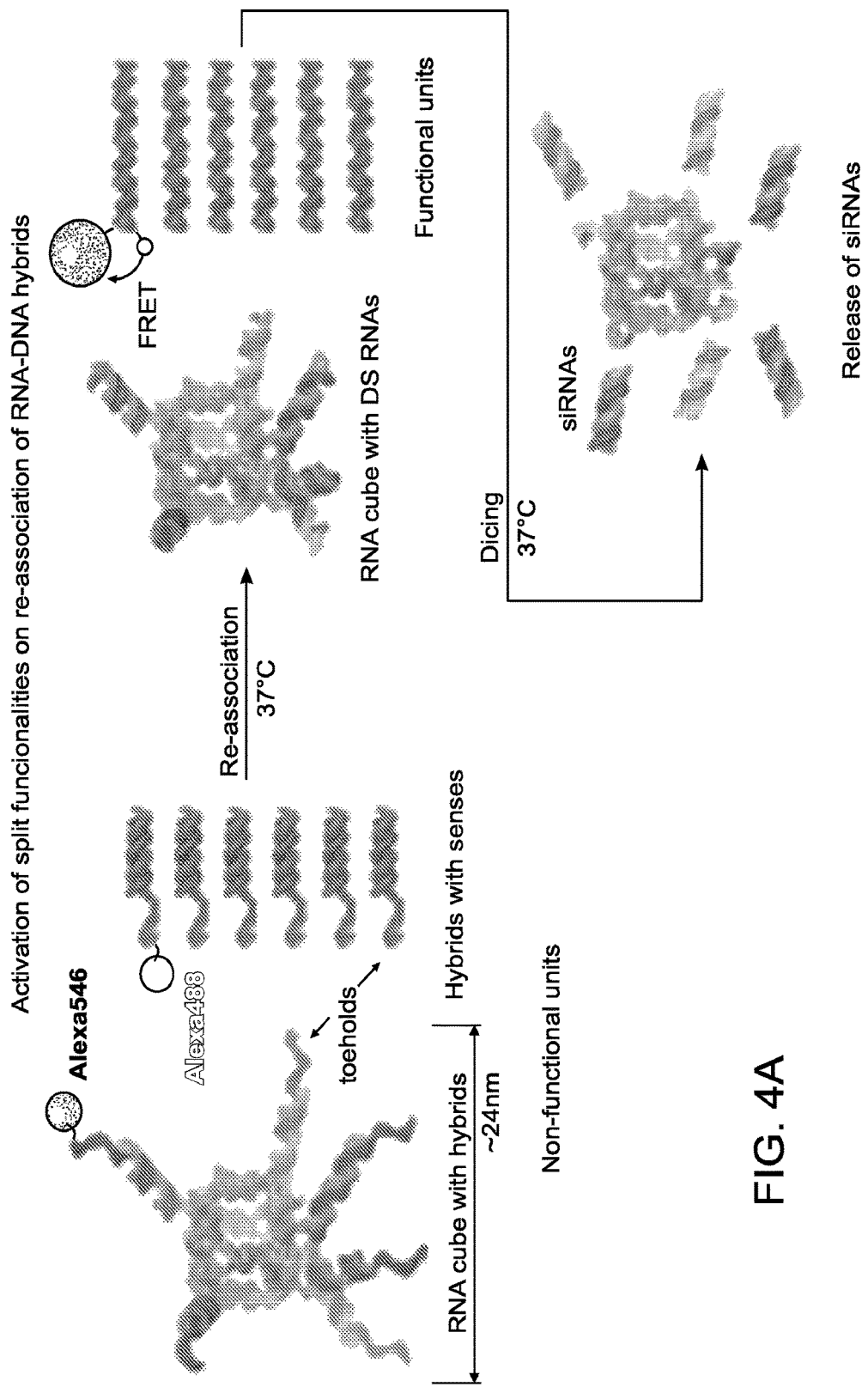
FIGS. 4A to 4D shows a schematic depicting activation of split functionalities during re-association of RNA nanocubes 3'-side decorated with six RNA-DNA (in blue) hybrids (carrying antisense strand of DsiRNA) with six cognate hybrids (carrying DsiRNA sense strands). (a) Schematics of re-association and activation of FRET and RNAi. (b) Assembled RNA cubes were analyzed by total SYBR Gold staining native PAGE and DLS experiments. (c) FRET time traces during re-association of fluorescently labeled cubes and hybrids labeled with Alexa 546 and Alex 488. (d) GFP knockdown assays statistically analyzed with flow cytometry experiments. It is noted that individual hybrids and RNA nanocubes decorated with hybrids, administered independently from one another, caused no decrease in eGFP expression.
Figure 4B:
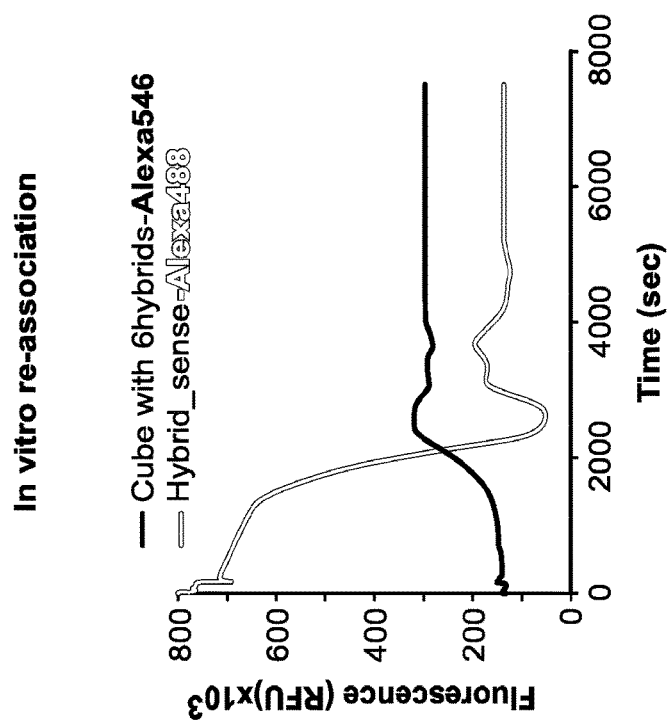
Figure 4C:
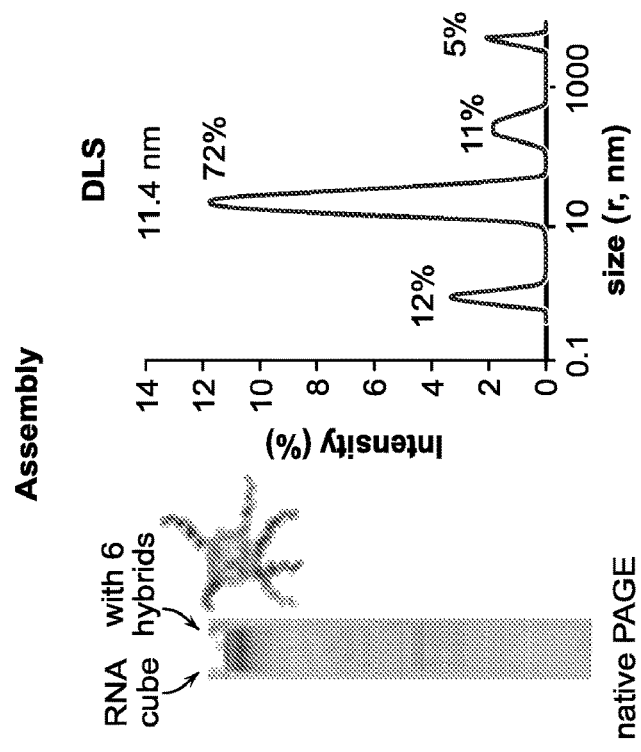
Figure 4D:
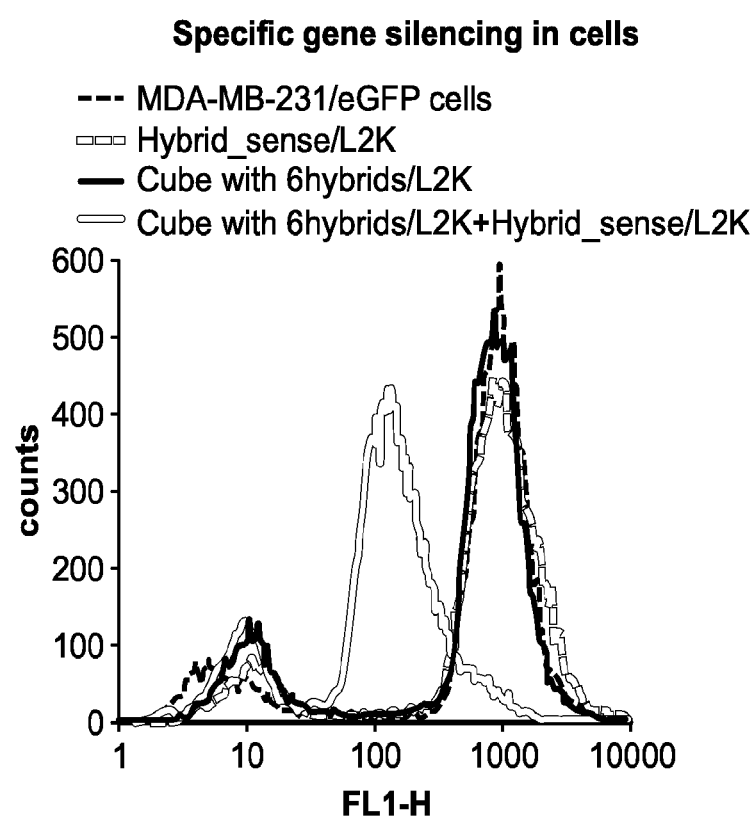

RNA Hybrid Nanocubes ("RNA-DNA Hybrid Nanocubes") Demonstrated Controlled Triggering To examine whether simultaneous delivery and activation of multiple split functionalities (e.g. RNA nanocubes with several DsiRNAs and FRET) could be triggered in a controlled manner, the same RNA nanocubes were decorated with RNA-DNA hybrids containing DNAs fluorescently labeled with Alexa 546 that were complementary to the antisense strands of DsiRNAs (FIG. 4a). The DNAs were designed to have ssDNA toeholds oriented outward from the nanocubes. An inward orientation of toeholds was also tested, but the assembly yields of nanoparticles made in this manner were very low (data not shown). Assemblies were confirmed by native-PAGE and DLS experiments, as shown in FIG. 4b. On their own, these nanoparticles did not activate the RNAi pathway in cells, due to the inability of Dicer to process the RNA-DNA hybrids of the nanocube arms (FIG. 13a). Cognate RNA-DNA hybrids were designed to carry the sense RNA strands of DsiRNAs hybridized to DNAs fluorescently labeled with Alexa 488. The in vitro re-association of RNA-DNA nanoparticles with cognate hybrids was monitored using FRET (FIG. 4c). These experiments demonstrated that DNA duplexes formed that positioned the pair of Alexa dyes within their Förster radius, thereby activating FRET. To confirm the release of active DsiRNAs on the RNA nanocube scaffolds that accompanied the formation of duplex DNA, silencing experiments were carried out using eGFP expressing cells (FIG. 4d). The cells were transfected with RNA-DNA nanocubes alone, the corresponding cognate free RNA-DNA heteroduplexes alone, or were co-transfected with both using individually prepared complexes with Lipofectamine2000 (L2K). As demonstrated in FIG. 4d, eGFP silencing occurred only when RNA-DNA nanocubes and the cognate RNA-DNA hybrids were simultaneously delivered into the cells. Thus, controlled triggering of RNA-DNA hybrid nanocubes was observed.

Example 5

Figure 5A:
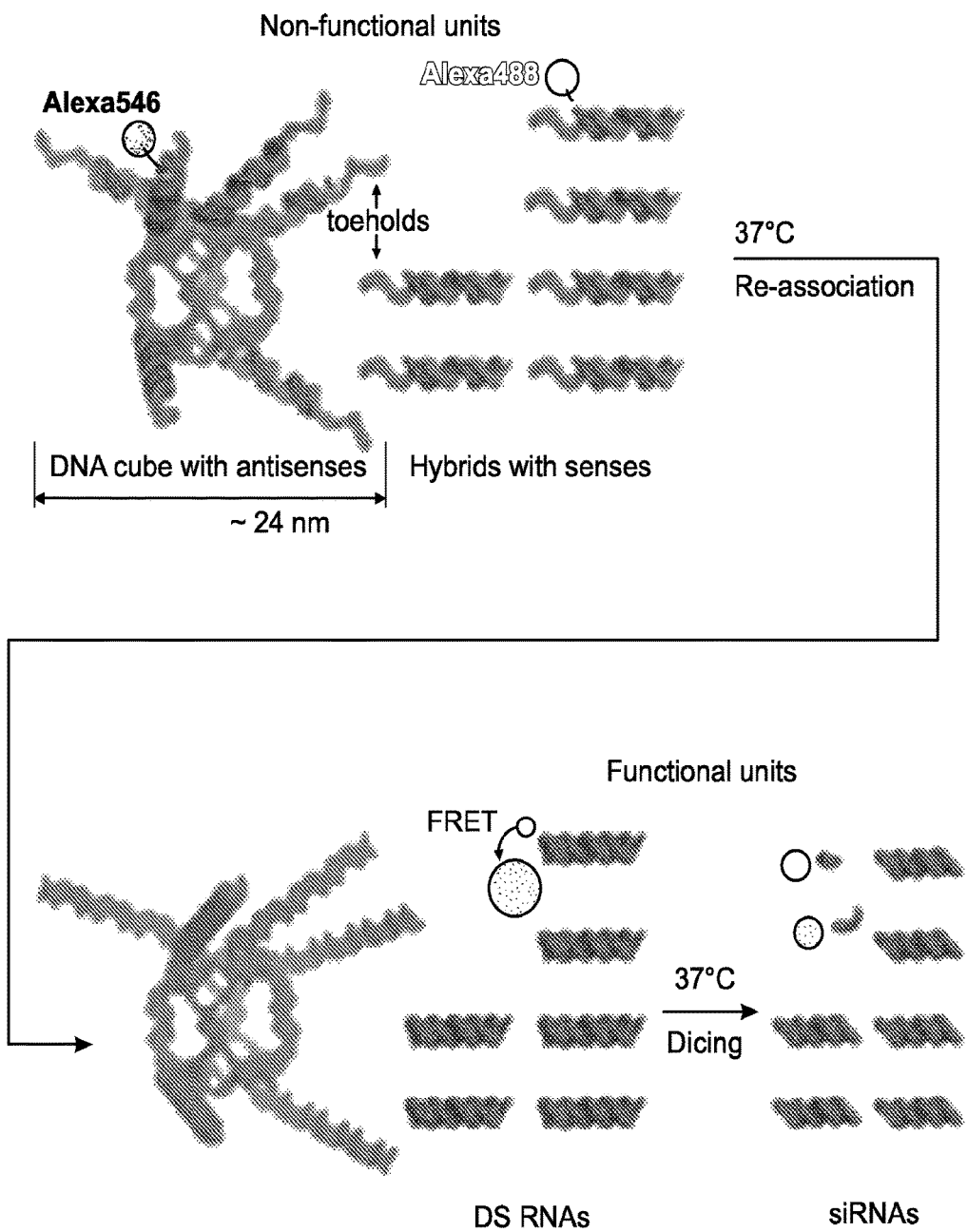
FIGS. 5A to 5E show activation of different split functionalities during re-association of DNA nanocubes (in blue) 3'-side decorated with six RNA-DNA hybrids (carrying six DsiRNA antisense strands, in red) with six cognate hybrids (carrying DsiRNA sense strands). (a) Schematics of re-association and activation of FRET and RNAi. (b) The formation of DNA cubes was confirmed by total SYBR Gold staining native PAGE and DLS experiments. (c) FRET time traces were captured during re-association of fluorescently labeled cubes and hybrids labeled with Alexa 546 and Alexa 488, respectively. (d) FRET experiments: cells were co-transfected with cubes and cognate hybrids labeled with Alexa546 and Alexa488, respectively, and images were taken on the next day. (e) GFP knockdown assays were statistically analyzed in flow cytometry experiments. It is noted that individual hybrids and DNA nanocubes decorated with hybrids, when administered in the absence of the other, caused no decrease in eGFP expression. Image numbers in (d) correspond to: differential interference contrast (DIC) images (1), Alexa488 emission (2), Alexa546 emission (3), bleed-through corrected FRET image (4), 3D chart representation of zoomed fragment indicated by a white box of bleed-through corrected FRET image with the white dot indicating the correspondence (5).
Figure 5B:
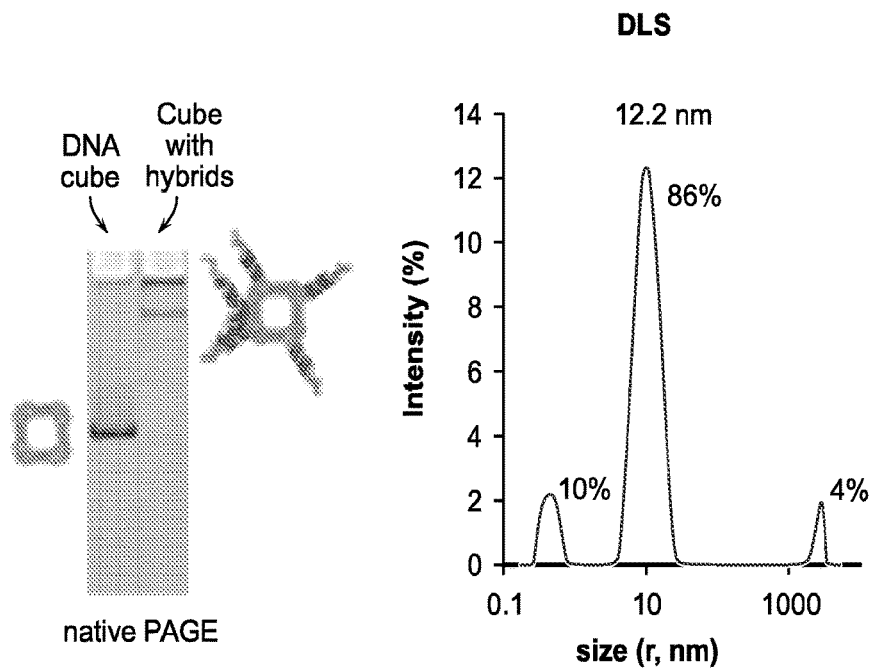
Figure 5C:
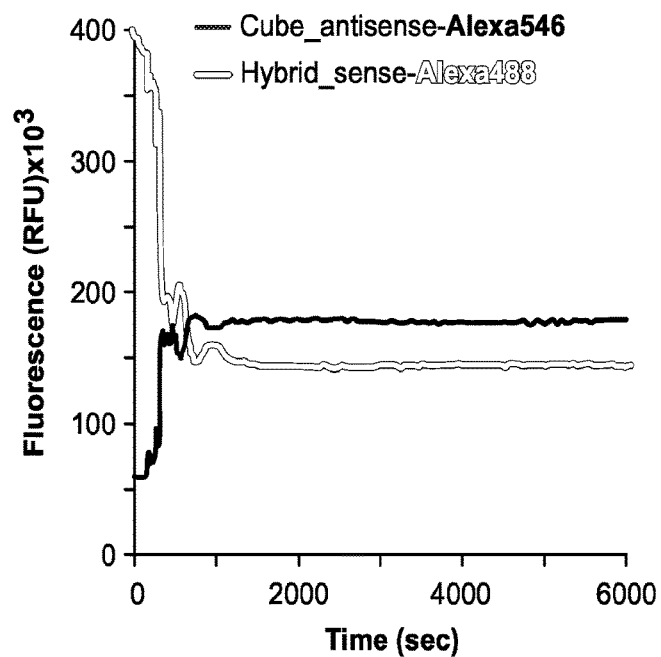
Figure 5D:
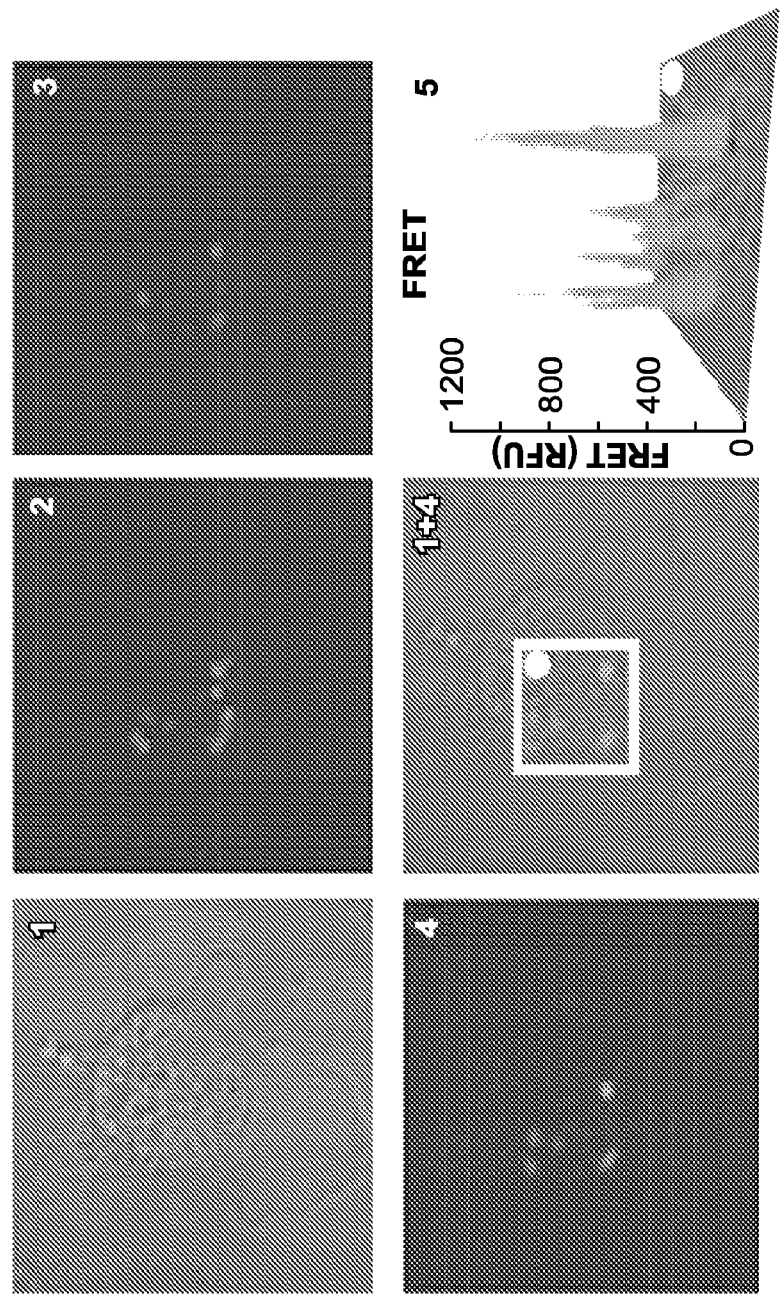
Figure 5E:
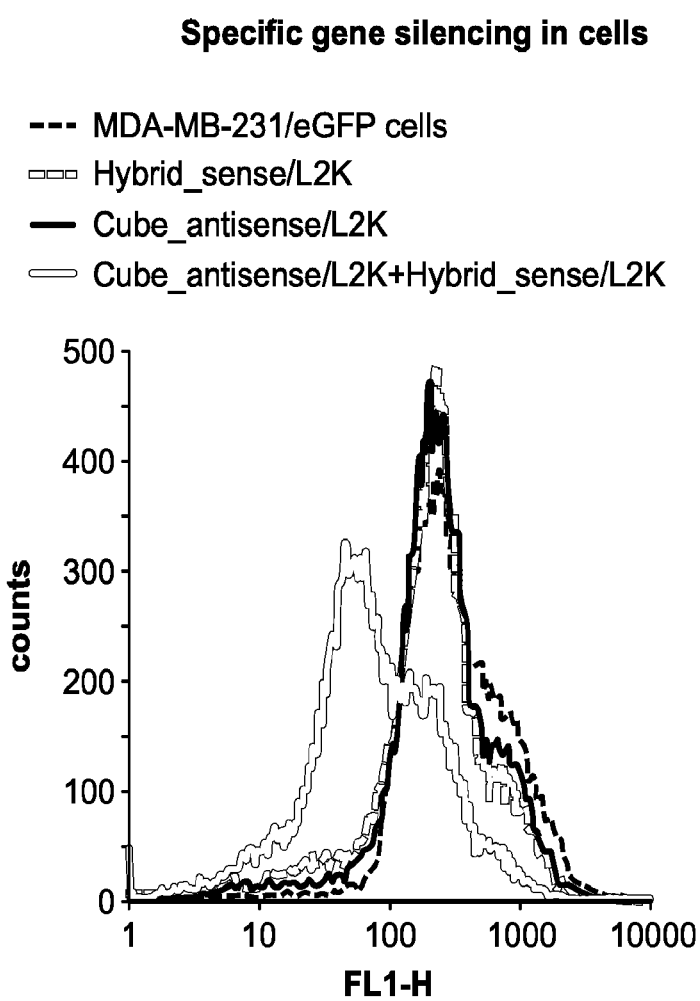
Figure 15B:
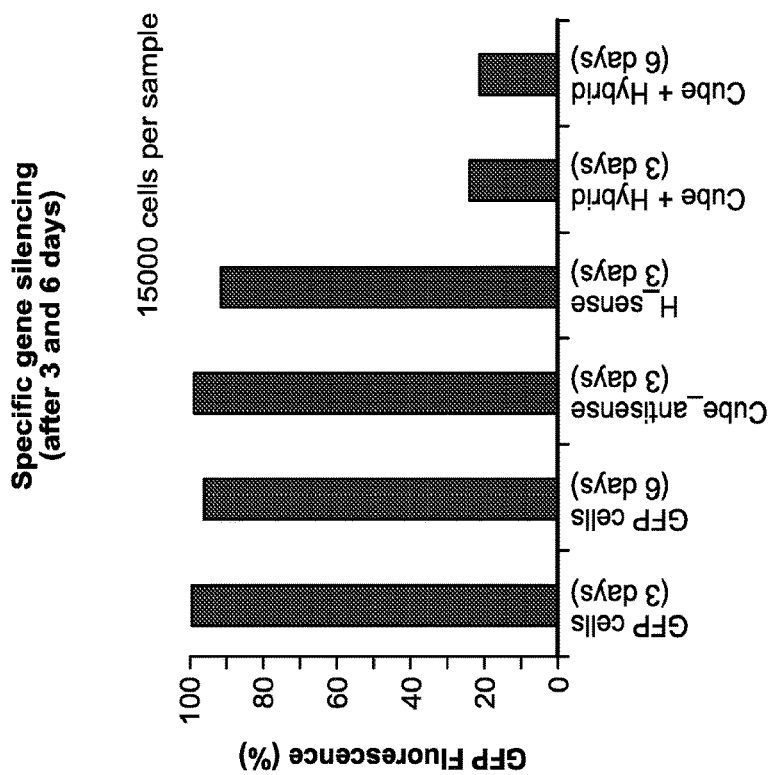
FIGS. 15A and 15B show fluorescent studies, in FIG. 15A of DNA cubes with six hybrids (containing antisense strands) re-associating with cognate hybrids in solution at 37° C. Fluorescently labeled cubes and hybrids individually associated with L2K prior to mixing were followed by fluorescent time tracing. It was noted that L2K formed complexes with hybrid cubes and hybrids, thus preventing their re-association, and the emission signal of Alexa488 (in green) stayed above Alexa546 (in red).
Figure 15A:
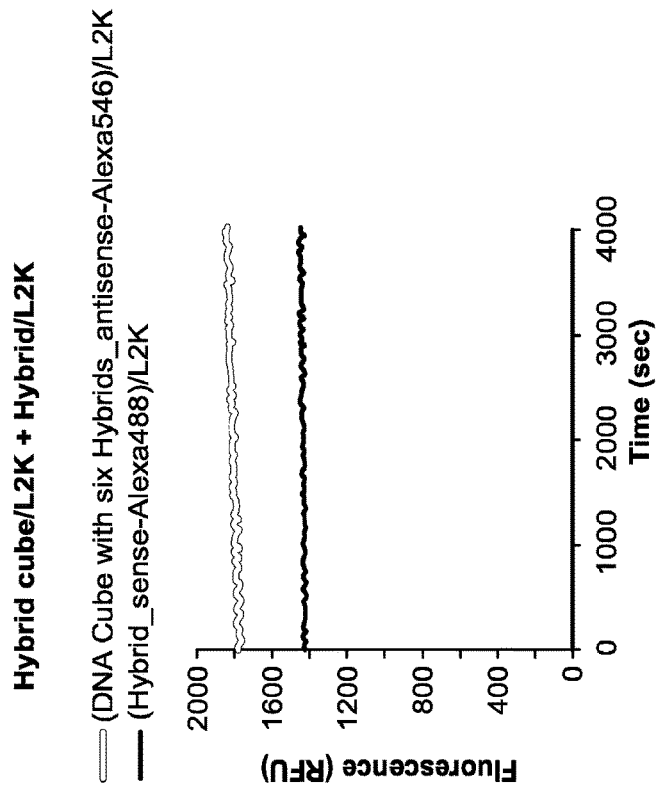
Figure 16B:
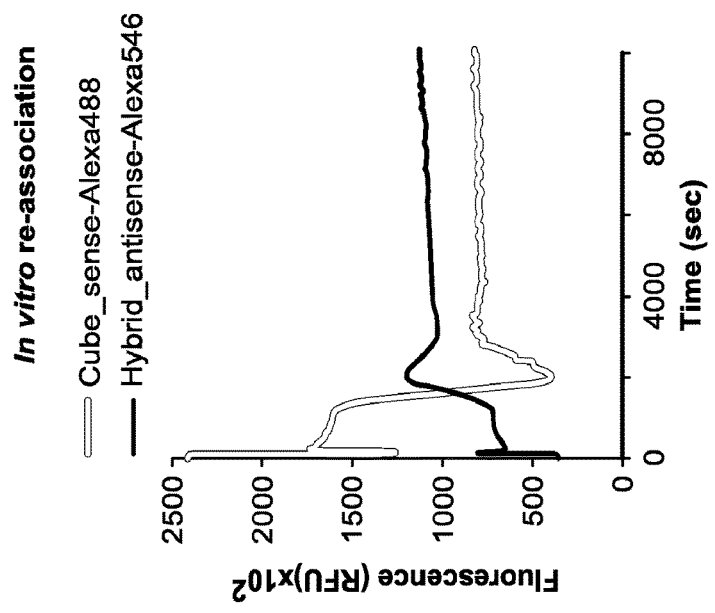
FIGS. 16A to 16D show activation of split functionalities with DNA cubes 5'-side decorated with RNA-DNA hybrids (carrying sense strands of DsiRNA) and six cognate hybrids (carrying antisense strands of DsiRNA).
Figure 16A:
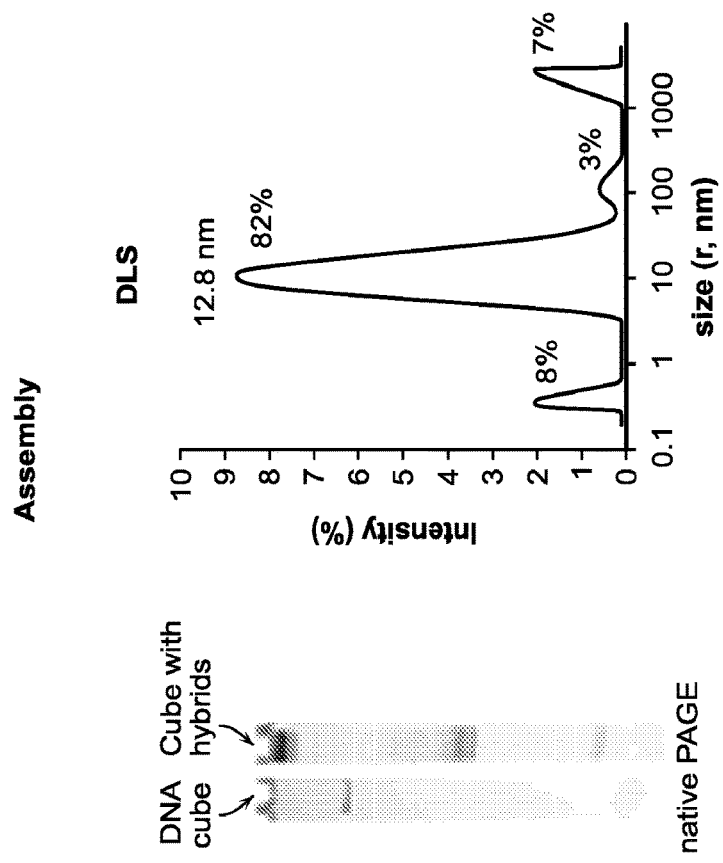
Figure 16C:
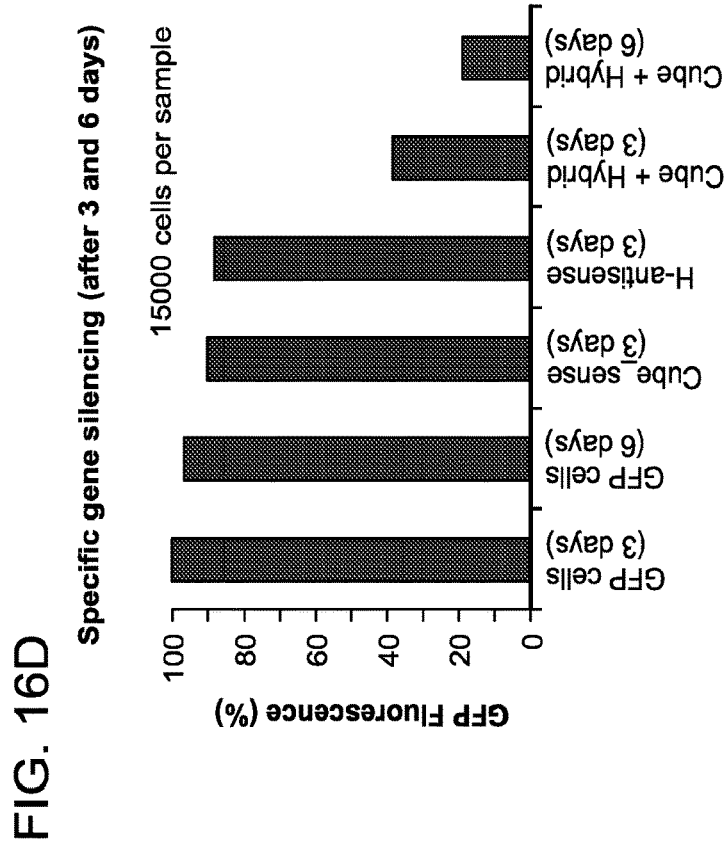
Figure 16D:
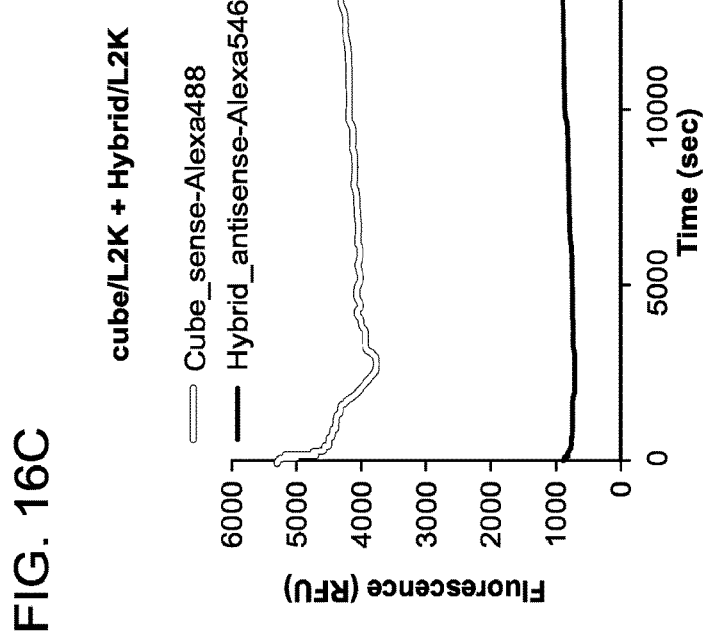

DNA Hybrid Nanocubes ("DNA-RNA Hybrid Nanocubes") Also Demonstrated Controlled Triggering As an alternative approach for simultaneous activation of multiple split functions in cells, it was newly hypothesized that DNA nanocubes could be used as scaffolds for presentation of hybrid arms (FIG. 5a). DNA scaffolds were decorated with six hybrid arms carrying antisense strands of DsiRNAs (thereby forming DNA-RNA hybrid nanocubes). Correct formation of DNA-RNA hybrid nanocubes was verified by native PAGE (FIG. 5b). Re-association of RNA parts of the heteroduplexes was then assessed and confirmed to have resulted in the release of functional DsiRNAs and activated FRET (FIG. 5a). The activation of FRET was confirmed in vitro (FIG. 5c) and in the cultured cells (FIG. 5d), and release of DsiRNAs was also observed through gene silencing experiments (FIGS. 5e and 15). The DNA-RNA hybrid cubes containing sense strands of DsiRNAs with the corresponding cognate RNA-DNA heteroduplexes carrying the antisense RNA strands were also extensively tested for size (native PAGE, FIG. 16a), assembly (DLS, FIG. 16b), re-association in vitro (FIG. 16c), lack of re-association when each modality was independently formulated in lipofectamine 2000 (FIG. 16d) and efficacy and duration of GFP target gene silencing when DNA-RNA nanocubes and cognate RNA-DNA hybrid molecules were either exclusively administered or were co-administered (FIG. 16e).

Example 6

DNA Hybrid Nanocubes Exhibited Reduced Activation of Interferons

Figure 17A:
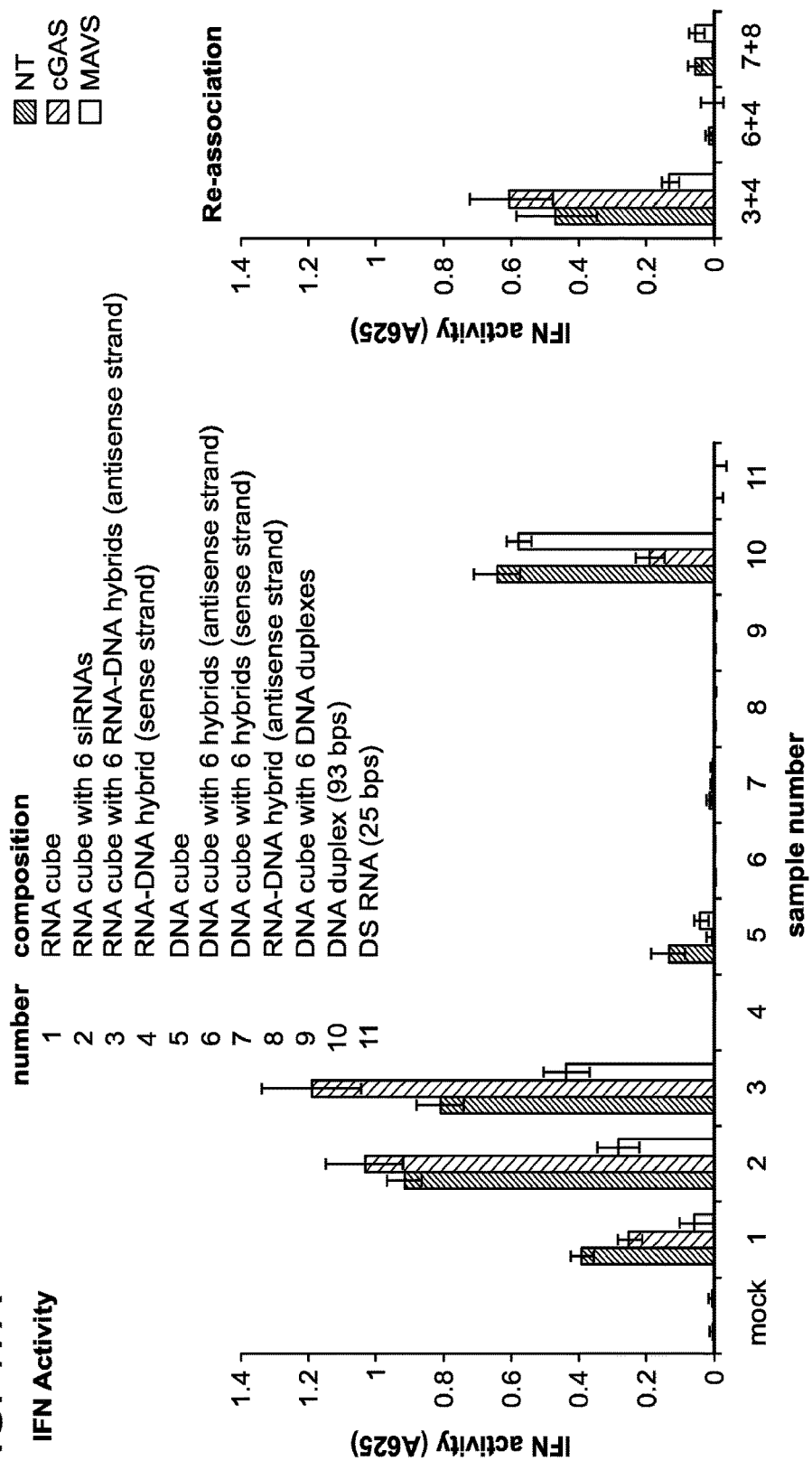
FIGS. 17A and 17B show IFN-activity experiments.
Figure 17B:
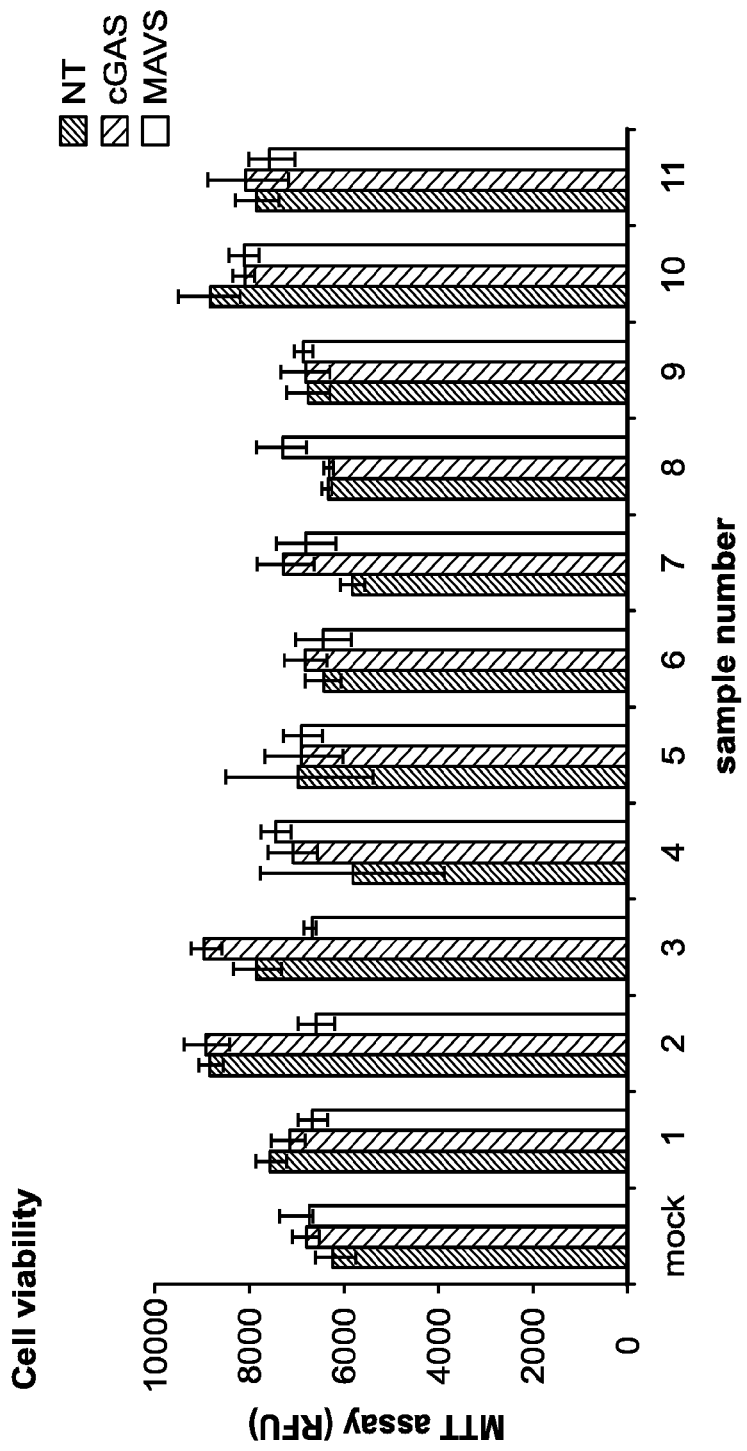

The type I interferon (IFN) response was examined for RNA-RNA nanocubes, RNA-DNA hybrid nanocubes and DNA-RNA hybrid nanocubes (FIG. 17a). RNA-containing cubes were potent stimulators of type I IFN, whereas DNA-containing cubes were relatively inert for production of a type I IFN response. Importantly, triggering of type I IFN was not related to any inherent toxicity of the nanocubes, based upon cell viability assays (FIG. 17b). RNA nanocube-induced stimulation of IFN activity required the adaptor protein MAVS, suggesting that signaling occurred through the canonical RNA-sensing pathways involving RIG-I and MDA5. Although DNA-containing cubes failed to trigger measurable type I IFN responses, as expected, a long dsDNA (93 bps) control molecule was able to induce a type I IFN response via cGAS, a DNA-binding receptor in the type I IFN signaling pathway[27]. These data indicated that the large DNA cubes identified and characterized herein were likely not recognized by cGAS. Furthermore, combining RNA or DNA cubes containing RNA-DNA hybrid arms with RNA-DNA hybrids carrying DNA complementary to the DNA present on the nanocube did not result in measureable DNA-dependent type I IFN-induction. These results (absence of measureable DNA-dependent type I IFN-induction) were not unexpected, in view of the fact that re-association resulted in only 39 bps DNA duplexes, and the level of IFN induction is directly proportional to the number of base pairs of the dsDNA[28]. Consistent with this, it was previously described that re-association of RNA-DNA hybrids yielding short dsDNA molecules was less efficient at stimulating type I IFN, as compared to those hybrids that released long dsDNA molecules[20]. Together, these data showed that DNA-RNA nanocubes were likely less immunogenic than both RNA-RNA and RNA-DNA nanocubes. Thus, DNA nanocubes having hybrid arms were identified as likely better suited for therapeutic purposes, as possessing reduced potential for inducing the side effects of cytokine release in a subject.

The above studies built and characterized three different nanocube-based strategies for activation of RNAi, two of which were entirely newly identified herein (RNA-DNA hybrid nanocubes and DNA-RNA nanocubes). The use of RNA nanocubes as scaffolds for multiple DsiRNAs was observed to be effective and is identified as guaranteeing a simple and straightforward, precisely programmable control over composition of RNAi agents so constructed. Indeed, triggerable control over RNAi knockdown was observed to be achieved with RNA-DNA hybrid nanocubes of the invention.

The application of DNA nanocubes carrying multiple split functionalities (DNA-RNA hybrid nanocubes) further appeared to possess additional advantages (as summarized in FIG. 18). These nanocubes were more resistant to human blood serum nucleases and had lower immunogenicity as compared to their RNA-based counterparts. The intracellular fluorescent tracking of hybrid re-association in the nanocubes was also more practical, because fluorescent dyes and any other additional functionality attached to the DNAs would not interfere with RNAi, which in DNA-RNA hybrid nanocubes is mediated by the DsiRNA released from the nanoparticle (as opposed to relying upon Dicer cleavage, as is required for RNAi functionality of the arms of RNA-DNA nanocubes). Furthermore, the essence of this novel technique likely takes advantage of multiple existing three-dimensional shapes characterized as being formed by DNA molecules[29-37].

Further discussion of these Examples 1-6 can be found Afonin et al., Triggering of RNA Interference with RNA-RNA, RNA-DNA, and DNA-RNA Nanoparticles, ACS Nano, Vol. 9, No. 1, pp. 251-259, published online December 18, 2014 and Afonin K A., Multifunctional RNA nanoparticles, Nano Lett., Vol. 14, No. 10, pp. 5662-71, Oct. 8, 2014, each of which are incorporate herein by reference in their entireties.

Equivalents

Those skilled in the art will recognize, or be able to ascertain using no more than routine experimentation, many equivalents to the specific embodiments of the invention described herein. Such equivalents are intended to be encompassed by the following claims.

Incorporation by Reference

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

The following specific references, also incorporated by reference, are indicated above by corresponding reference number.

1. Fire, A. et al. Potent and specific genetic interference by double-stranded RNA in *Caenorhabditis elegans*. *Nature* 391, 806-811 (1998).
2. Elbashir, S. M., Lendeckel, W. & Tuschl, T. RNA interference is mediated by 21- and 22-nucleotide RNAs. *Genes & development* 15, 188-200 (2001).
3. Chen, J. & Xie, J. Progress on RNAi-based molecular medicines. *International journal of nanomedicine* 7, 3971-3980 (2012).

4. Pecot, C. V., Calin, G. A., Coleman, R. L., Lopez-Berestein, G. & Sood, A. K. RNA interference in the clinic: challenges and future directions. *Nat Rev Cancer* 11, 59-67 (2011).
5. Guo, P. The emerging field of RNA nanotechnology. *Nat Nanotechnol* 5, 833-842 (2010).
6. Bramsen, J. B. & Kjems, J. Development of Therapeutic-Grade Small Interfering RNAs by Chemical Engineering. *Front Genet* 3 (2012).
7. Afonin, K. A. et al. In Silico Design and Enzymatic Synthesis of Functional RNA Nanoparticles. *Accounts of Chemical Research* dx.doi.org/10.1021/ar400329z (2014).
8. Shukla, G. C. et al. A Boost for the Emerging Field of RNA Nanotechnology. *ACS nano* 5, 3405-3418 (2011).
9. Afonin, K. A., Lindsay, B. & Shapiro, B. A. Engineered RNA Nanodesigns for Applications in RNA Nanotechnology. *RNA Nanotechnology* 1, 1-15 (2013).
10. Shu, Y. et al. Stable RNA nanoparticles as potential new generation drugs for cancer therapy. *Advanced drug delivery reviews* 66C, 74-89 (2014).
11. Chworos, A. et al. Building programmable jigsaw puzzles with RNA. *Science* 306, 2068-2072 (2004).
12. Jaeger, L. & Chworos, A. The architectonics of programmable RNA and DNA nanostructures. *Current opinion in structural biology* 16, 531-543 (2006).
13. Afonin, K. A. et al. Design and self-assembly of siRNA-functionalized RNA nanoparticles for use in automated nanomedicine. *Nat Protoc* 6, 2022-2034 (2011).
14. Binzel, D. W., Khisamutdinov, E. F. & Guo, P. Entropy-Driven One-Step Formation of Phi29 pRNA 3WJ from Three RNA Fragments. *Biochemistry* 53, 2221-2231 (2014).
15. Khisamutdinov, E. F., Jasinski, D. L. & Guo, P. RNA as a Boiling-Resistant Anionic Polymer Material To Build Robust Structures with Defined Shape and Stoichiometry. *ACS nano* (2014).
16. Dibrov, S. M., McLean, J., Parsons, J. & Hermann, T. Self-assembling RNA square. *Proc Natl Acad Sci USA* 108, 6405-6408 (2011).
17. Ohno, H. et al. Synthetic RNA-protein complex shaped like an equilateral triangle. *Nat Nanotechnol* 6, 116-120 (2011).
18. Shu, D., Khisamutdinov, E. F., Zhang, L. & Guo, P. Programmable folding of fusion RNA in vivo and in vitro driven by pRNA 3WJ motif of phi29 DNA packaging motor. *Nucleic acids research* 42, e10 (2014).
19. Afonin, K. A. et al. Activation of different split functionalities on re-association of RNA-DNA hybrids. *Nat Nanotechnol* 8, 296-304 (2013).
20. Afonin, K. A. et al. Co-transcriptional production of RNA-DNA hybrids for simultaneous release of multiple split functionalities. *Nucleic acids research* 42, 2085-2097 (2014).
21. Afonin, K. A. et al. In vitro assembly of cubic RNA-based scaffolds designed in silico. *Nat Nanotechnol* 5, 676-682 (2010).
22. Afonin, K. A. et al. Computational and Experimental Characterization of RNA Cubic Nanoscaffolds. *Methods* (2014).
23. Rose, S. D. et al. Functional polarity is introduced by Dicer processing of short substrate RNAs. *Nucleic acids research* 33, 4140-4156 (2005).
24. Low, J. T. et al. SHAPE-directed discovery of potent shRNA inhibitors of HIV-1. *Mol Ther* 20, 820-828 (2012).
25. Grimm, D. & Kay, M. A. Combinatorial RNAi: a winning strategy for the race against evolving targets? *Mol Ther* 15, 878-888 (2007).
26. Berkhout, B. & Sanders, R. W. Molecular strategies to design an escape-proof antiviral therapy. *Antiviral Res* 92, 7-14 (2011).
27. Sun, L., Wu, J., Du, F., Chen, X. & Chen, Z. J. Cyclic GMP-AMP synthase is a cytosolic DNA sensor that activates the type I interferon pathway. *Science* 339, 786-791 (2013).
28. Stetson, D. B. & Medzhitov, R. Recognition of cytosolic DNA activates an IRF3-dependent innate immune response. *Immunity* 24, 93-103 (2006).
29. Chen, J. H. & Seeman, N. C. Synthesis from DNA of a molecule with the connectivity of a cube. *Nature* 350, 631-633 (1991).
30. Lee, H. et al. Molecularly self-assembled nucleic acid nanoparticles for targeted in vivo siRNA delivery. *Nat Nanotechnol* 7, 389-393 (2012).
31. Andersen, E. S. et al. Self-assembly of a nanoscale DNA box with a controllable lid. *Nature* 459, 73-76 (2009).
32. Kuzyk, A. et al. DNA-based self-assembly of chiral plasmonic nanostructures with tailored optical response. *Nature* 483, 311-314 (2012).
33. Rothemund, P. W. Folding DNA to create nanoscale shapes and patterns. *Nature* 440, 297-302 (2006).
34. Douglas, S. M. et al. Self-assembly of DNA into nanoscale three-dimensional shapes. *Nature* 459, 414-418 (2009).
35. He, Y. et al. Hierarchical self-assembly of DNA into symmetric supramolecular polyhedra. *Nature* 452, 198-201 (2008).
36. Goodman, R. P. et al. Reconfigurable, braced, three-dimensional DNA nanostructures. *Nat Nanotechnol* 3, 93-96 (2008).
37. Seeman, N. C. Nanomaterials based on DNA. *Annual review of biochemistry* 79, 65-87 (2010).
38. Martinez, H. M., Maizel, J. V., Jr. & Shapiro, B. A. RNA2D3D: a program for generating, viewing, and comparing 3-dimensional models of RNA. *Journal of biomolecular structure & dynamics* 25, 669-683 (2008).
39. Parisien, M. & Major, F. The MC-Fold and MC-Sym pipeline infers RNA structure from sequence data. *Nature* 452, 51-55 (2008).
40. Popenda, M. et al. Automated 3D structure composition for large RNAs. *Nucleic acids research* 40, e112 (2012).
41. Afonin, K. A. et al. Co-transcriptional Assembly of Chemically Modified RNA Nanoparticles Functionalized with siRNAs. *Nano letters* 12, 5192-5195 (2012).
42. Afonin, K. A., Cieply, D. J. & Leontis, N. B. Specific RNA self-assembly with minimal paranemic motifs. *Journal of the American Chemical Society* 130, 93-102 (2008).
43. Afonin, K. A. & Leontis, N. B. Generating new specific RNA interaction interfaces using C-loops. *Journal of the American Chemical Society* 128, 16131-16137 (2006).
44. Kim, T. et al. In Silico, In Vitro, and In Vivo Studies Indicate the Potential Use of Bolaamphiphiles for Therapeutic siRNAs Delivery. *Mol Ther Nucleic Acids* 2, e80 (2013).
45. Afonin et al., Triggering of RNA Interference with RNA-RNA, RNA-DNA, and DNA-RNA Nanoparticles, ACS Nano, Vol. 9, No. 1, pp. 251-259, published online Dec. 18, 2014.
46. Afonin K. A., Multifunctional RNA nanoparticles, Nano Lett., Vol. 14, No. 10, pp. 5662-71, Oct. 8, 2014.

What is claimed is:

1. A DNA nanoparticle that is capable of becoming activated for RNAi activity, comprising:
a six-stranded DNA oligonucleotide nanocube with three single-stranded thymines at each corner of the nanocube, the DNA oligonucleotides being capable of self-assembling to form the DNA oligonucleotide nanocube, wherein one to six of the DNA oligonucleotides of the DNA oligonucleotide nanocube comprises only one single strand R/DNA arm covalently attached thereto;
one to six cognate single strand R/DNA molecule(s), each of the cognate single strand R/DNA molecule(s) being capable of annealing at least one of the one to six R/DNA single strand arm(s) to form R/DNA hybrid arm(s);
wherein the DNA oligonucleotide nanocube becomes activated for RNAi activity upon association with free R/DNA hybrid molecule(s) that present strand(s) capable of annealing to corresponding DNA and RNA strand(s) of the R/DNA hybrid arm(s) to form RNA/RNA or DNA/DNA hybrid arm(s) and free RNA/RNA or DNA/DNA hybrid molecule(s).

2. The DNA nanoparticle of claim 1, wherein each DNA oligonucleotide of the DNA oligonucleotide nanocube comprises only one covalently attached single strand R/DNA arm.

3. The DNA nanoparticle of claim 1, wherein each of said six DNA oligonucleotides comprises the following sequence structure: 5'-$N_6$-TTT-$N_{10}$-TTT-$N_{10}$-TTT-$N_{10}$-TTT-$N_4$-3' (SEQ ID NO: 1), wherein each N is a deoxyribonucleotide.

4. The DNA nanoparticle of claim 2, wherein the single strand R/DNA arms are covalently attached at the 3' ends of the DNA oligonucleotides of the DNA oligonucleotide nanocube.

5. The DNA nanoparticle of claim 1, wherein the single strand R/DNA arm(s) are capable of annealing to a sense or antisense strand of a split RNAi agent.

6. The DNA nanoparticle of claim 5, wherein said split RNAi agent is a siRNA or DsiRNA.

7. A RNA nanoparticle that is capable of becoming activated for RNAi activity, comprising:
a six-stranded RNA oligonucleotide nanocube with three single-stranded uracils at each corner of the nanocube, the RNA oligonucleotides being capable of self-assembling to form the RNA oligonucleotide nanocube, wherein one to six of the RNA oligonucleotides of the RNA oligonucleotide nanocube each comprises only one single strand R/DNA arm covalently attached thereto;
one to six cognate single strand R/DNA molecule(s), each of the cognate single strand R/DNA molecule(s) being capable of annealing to at least one of the one to six R/DNA single strand arm(s) to form R/DNA hybrid arm(s);
wherein the RNA oligonucleotide nanocube becomes activated for RNAi activity upon association with free R/DNA hybrid molecule(s) that present strand(s) capable of annealing to corresponding DNA and RNA strand(s) of the R/DNA hybrid arm(s) to form RNA/RNA or DNA/DNA hybrid arm(s) and free RNA/RNA or DNA/DNA hybrid molecule(s).

8. The RNA nanoparticle of claim 7, wherein each single strand RNA molecule of the RNA oligonucleotide nanocube comprises only one covalently attached single strand R/DNA arm.

9. The RNA nanoparticle of claim 7, wherein each of said six single strand RNA molecules comprises the following sequence structure: 5'-$N_6$-UUU-$N_{10}$-UUU-$N_{10}$-UUU-$N_{10}$-UUU-$N_4$-3' (SEQ ID NO: 2), wherein each N is a ribonucleotide.

10. The RNA nanoparticle of claim 7, wherein the single strand R/DNA arm(s) is/are covalently attached at the 3' end(s) of the RNA molecule(s) of the RNA oligonucleotide nanocube.

11. The RNA nanoparticle of claim 7, wherein the single strand R/DNA arm(s) are capable of annealing to a sense or antisense strand of a split RNAi agent.

12. The RNA nanoparticle of claim 11, wherein said split RNAi agent is a siRNA or DsiRNA.

13. A pharmaceutical composition for triggering RNA interference comprising a DNA nanoparticle of claim 1 and a pharmaceutical excipient, wherein the DNA nanoparticle is in an inactive state until combined with a free R/DNA hybrid molecule that presents strands capable of annealing to corresponding DNA and RNA strands of the R/DNA hybrid arms to from RNA/RNA or DNA/DNA hybrid arms and free RNA/RNA or DNA/DNA hybrid molecules.

14. A pharmaceutical composition for triggering RNA interference comprising a RNA nanoparticle of claim 7 and a pharmaceutical excipient, wherein the RNA nanoparticle is in an inactive state until combined with a free R/DNA hybrid molecule that presents strands capable of annealing to corresponding DNA and RNA strands of the R/DNA hybrid arms to form RNA/RNA or DNA/DNA hybrid arms and free RNA/RNA or DNA/DNA hybrid molecules.

15. A method for treating a subject having a disease or disorder treatable with one or more RNAi agents, comprising administering a composition of claim 13.

16. A method for treating a subject having a disease or disorder treatable with one or more RNAi agents, comprising administering a composition of claim 14.

17. The DNA nanoparticle of claim 1, wherein the activation of the DNA nanoparticle for RNAi activity causes immune modulation.

18. The RNA nanoparticle of claim 7, wherein the activation of the RNA nanoparticle for RNAi activity causes immune modulation.

* * * * *